(12) United States Patent
Eid et al.

(10) Patent No.: US 8,906,831 B2
(45) Date of Patent: Dec. 9, 2014

(54) SINGLE MOLECULE LOADING METHODS AND COMPOSITIONS

(75) Inventors: John Eid, San Francisco, CA (US); Stephen Turner, Menlo Park, CA (US); Ravi Dalal, Menlo Park, CA (US); Benjamin Flusberg, Palo Alto, CA (US); Jonas Korlach, Newark, CA (US); Steven Lin, Palo Alto, CA (US); Adrian Fehr, Los Altos, CA (US); Fred Christians, Los Altos Hills, CA (US); Robin Emig, Belmont, CA (US); Jeremy Gray, San Francisco, CA (US); Robert Sebra, San Francisco, CA (US); Lei Sun, San Jose, CA (US); Stephen Dudek, San Francisco, CA (US)

(73) Assignee: Pacific Biosciences of California, Inc., Menlo Park, CA (US)

(*) Notice: Subject to any disclaimer, the term of this patent is extended or adjusted under 35 U.S.C. 154(b) by 915 days.

(21) Appl. No.: 12/384,097

(22) Filed: Mar. 30, 2009

(65) Prior Publication Data

US 2010/0009872 A1 Jan. 14, 2010

Related U.S. Application Data

(60) Provisional application No. 61/072,641, filed on Mar. 31, 2008, provisional application No. 61/139,316, filed on Dec. 19, 2008.

(51) Int. Cl.
*C12Q 1/48* (2006.01)
*C12N 11/14* (2006.01)
(Continued)

(52) U.S. Cl.
CPC .... *G01N 33/54313* (2013.01); *G01N 33/54366* (2013.01); *C12N 2310/50* (2013.01); *C40B 40/06* (2013.01); *C12Q 1/6869* (2013.01); *C12Q 2535/122* (2013.01); *C12N 2310/51* (2013.01)
USPC .................. 506/16; 506/3; 506/37; 536/22.1; 702/20

(58) Field of Classification Search
CPC ............... C12N 11/14; C12N 2310/00; C12N 2310/50; C12N 2310/51; C40B 60/08; C40B 40/06; C40B 20/02; C12Q 1/6869; C12Q 2535/101; C12Q 2535/122
See application file for complete search history.

(56) References Cited

U.S. PATENT DOCUMENTS 5,350,686 A 9/1994 Jhingan
6,917,726 B2 7/2005 Levene et al.
(Continued)

FOREIGN PATENT DOCUMENTS

WO WO 2007/075987 A2 5/2007
WO WO 2007/075873 A2 7/2007
(Continued)

OTHER PUBLICATIONS

Oliphant et al., Biotechniques, 2002, 32:S56-S61.*

(Continued)

*Primary Examiner* — Christopher M Babic
*Assistant Examiner* — Jeremy C Flinders
(74) *Attorney, Agent, or Firm* — Robert H. Reamey

(57) ABSTRACT

Methods for non-random loading of single analyte molecules into array structures are provided. The methods allow for distribution of a population of target molecules into a plurality of size confined regions such as wells. Sizing moieties are linked to individual target molecules. The sizing moieties are of sufficient size, relative to the size-confined reaction or observation regions, such that only a selected number of sizing moieties will fit into the size confined regions. The confined regions and the sizing moieties or target molecules comprise a selected charge that allow for controlling the loading of the sizing moities.

15 Claims, 35 Drawing Sheets

(51) Int. Cl.
*G01N 33/543* (2006.01)
*C40B 20/02* (2006.01)
*C40B 60/08* (2006.01)
*C40B 40/06* (2006.01)
*C12Q 1/68* (2006.01)

(56) References Cited

U.S. PATENT DOCUMENTS

| | | |
|---|---|---|
| 7,033,764 B2 | 4/2006 | Korlach et al. |
| 7,052,847 B2 | 5/2006 | Korlach et al. |
| 7,056,661 B2 | 6/2006 | Korlach et al. |
| 7,056,676 B2 | 6/2006 | Korlach et al. |
| 2003/0044781 A1 | 3/2003 | Korlach et al. |
| 2005/0106758 A1 | 5/2005 | Fukumoto et al. |
| 2006/0061754 A1 | 3/2006 | Turner et al. |
| 2007/0161017 A1 | 7/2007 | Eid et al. |
| 2007/0238679 A1 | 10/2007 | Rank et al. |
| 2008/0220537 A1 | 9/2008 | Foquet |
| 2008/0241866 A1 | 10/2008 | Korlach et al. |
| 2008/0241892 A1 | 10/2008 | Roitman et al. |
| 2009/0118129 A1 | 5/2009 | Turner |
| 2010/0261158 A1* | 10/2010 | Nordman et al. .......... 435/6 |

FOREIGN PATENT DOCUMENTS

WO WO 2008/121374 A2 10/2008
WO WO 2008/140758 A1 11/2008

OTHER PUBLICATIONS

Marblestone et al., Protein Science, 2006, 15(1):182-18.*
Tolbert et al., Angew. Chem. Int. Ed., 2002, 41:2171-2174.*
Grego et al., Langmuir, 2005, 21:4971-4975.*
Holmberg et al., Electrophoresis, 2005, 26:501-510.*
Adhikari et al. (2007) "Conditions for subeutectic growth of Ge nanowires by the vapor-liquid-solid mechanism" *Journal of Applied Physics*, 102: 94311-94316.
Andersen et al. (2008) "Assembly and structural analysis of a covalently closed nano-scale DNA cage" *Nucleic Acids Research*, 36(4): 1113-1119.
Cerofolini, et al. (2005) "Strategies for nanoelectronics." *Microelectonic Engineering*, 81: 405-419.
Chen, et al. (2004) "Critical point energy as a function of electric field determined by electroreflectance of surface-intrinsic-$n^+$ type doped GaAs", *Applied Physics Letters*, 84(18):4017-4019.
Cohen and Moerner (2005) "Method for trapping and manipulating nanoscale objects in solution." *Applied Physics Letters*, 86: 093109-1-093109-3.
Eid et al. (2008) "Real-Time DNA Sequencing from Single Polymerase Molecules" *Science*, 323(5910): 133-138.
Foquet et al. (2008) "Improved fabrication of zero-mode waveguides for single-molecule detection" *Journal of Applied Physics*, 103: 034301-1-034301-9.
Korlach et al. (2008) "Selective aluminum passivation for targeted immobilization of single DNA polymerase molecules in zero-mode waveguide nanostructures" *Proceedings of the National Academy of Sciences, U.S.A.*, 105(4): 1176-1181.
Levene et al. (2003) "Zero Mode Waveguides for single Molecule Analysis at High Concentrations," *Science*, 299(5607): 682-686.
Leyden et al., (1977) "Tailoring surfaces with silanes." *Symposium on Silylated Surfaces*, Gordon & Breach 1980; Arkles, Chemtech 7: 766-778.
Montemagno and Bachand (1999) Constructing nanomechanical devices powered by biomolecular motors.: *Nanotechnology*, 10:225-231.
Park et al. (2006) "Finite-Size, Fully Addressable DNA Tile Lattices Formed by Hierarchical Assembly Procedures" *Angewande Cheme International Edition*, 45: 735-739.
Richter et al., (2000) "In situ and interrupted-growth studies of the self-assembly of octadecyltrichlorosilane monolayers." *Physical Review. E*, 61: 607-615.
Rothemund (2006) "Folding DNA to create nanoscale shapes and patterns." *Nature*, 440: 297-302.
Rothemund et al. (2004) "Algorithmic Seff-Assembly of DNA Sierpinski Triangles", *PLoS Biology*, 2(12)e424: 2041-2053.
Svoboda and Block (1994) "Biological Applications of Optical Forces" *Annual Review of Biophysics and Bimolecular Structure*, 23: 247-285.
Weizmann et al. (2008) "A polycatenated DNA scaffold for the one-step assembly of hierarchical nanostructures" *Proceedings of the National Academy of Sciences, U.S.A.*, 105(14): 5289-5294.
Woodruff et al. (2007) "Vertically Oriented Germanium Nanowires Grown from Gold Colloids on Silicon Substrates and Subsequent Gold Removal" *Nano Letters*, 7(6):1637-1642.
Zhang et al. (2006) "Periodic Square-Like Gold Nanoparticle Arrays Templated by Self-Assembled 2D DNA Nanogrids on a Surface" *Nano Letters* 6(2): 248-251.
Zhang et al. (2008) Conformational flexibility facilitates self-assembly of complex DNA nanostructures *Proceedings of the National Academy of Sciences, U.S.A.*, 105(31): 10665-10669.
Zimmermann et al. (2007) "Self-Assembly of a DNA Dodecahedron from 20 Trisoligonucleotides with $C_{3h}$ Linkers" *Angewandte Chemie International Edition*, 47: 3626-3630.
Gorris et al., "Optical-Fiber Bundles," Febs Journ (2007) 274(21):5462-5470.
International Search Report and Written Opinion dated Nov. 3, 2009 for related case PCT/US2009/001970.
Supplemental EP Search Report dated Apr. 27, 2011 for related case EP 09755181.6.
Second Office Action dated Aug. 10, 2012 for related case EP 09755181.6.
First Office Action dated Feb. 8, 2012 for related case EP 09755181.6.
International Search Report and Written Opinion dated Feb. 8, 2012 for related case PCT/US2011/000747.
International Preliminary Report on Patentability dated Nov. 1, 2012 for related case PCT/US2011/000747.
First Office Action dated Apr. 1, 2014 for related case AU 2009251881.

* cited by examiner

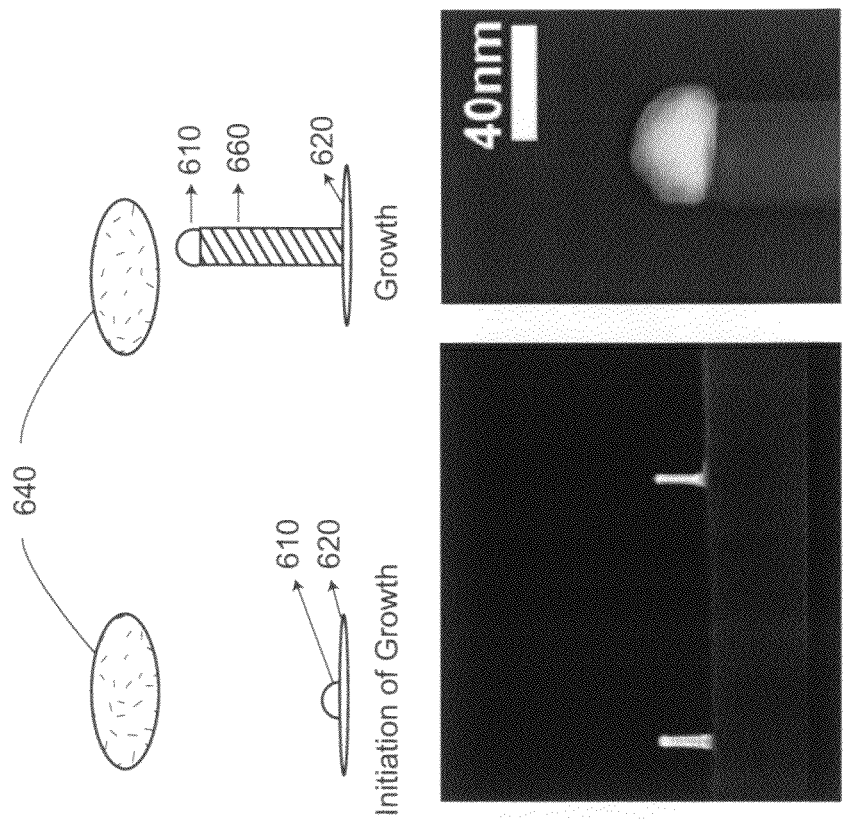
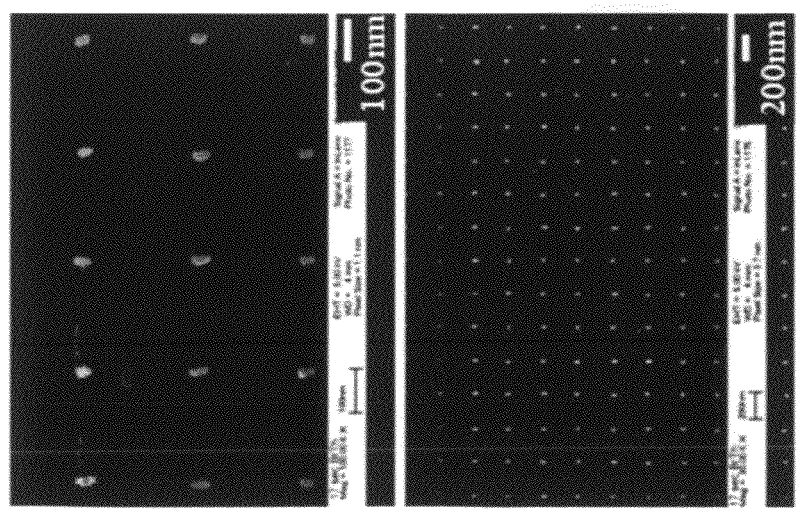
Fig. 6A
Fig. 6B

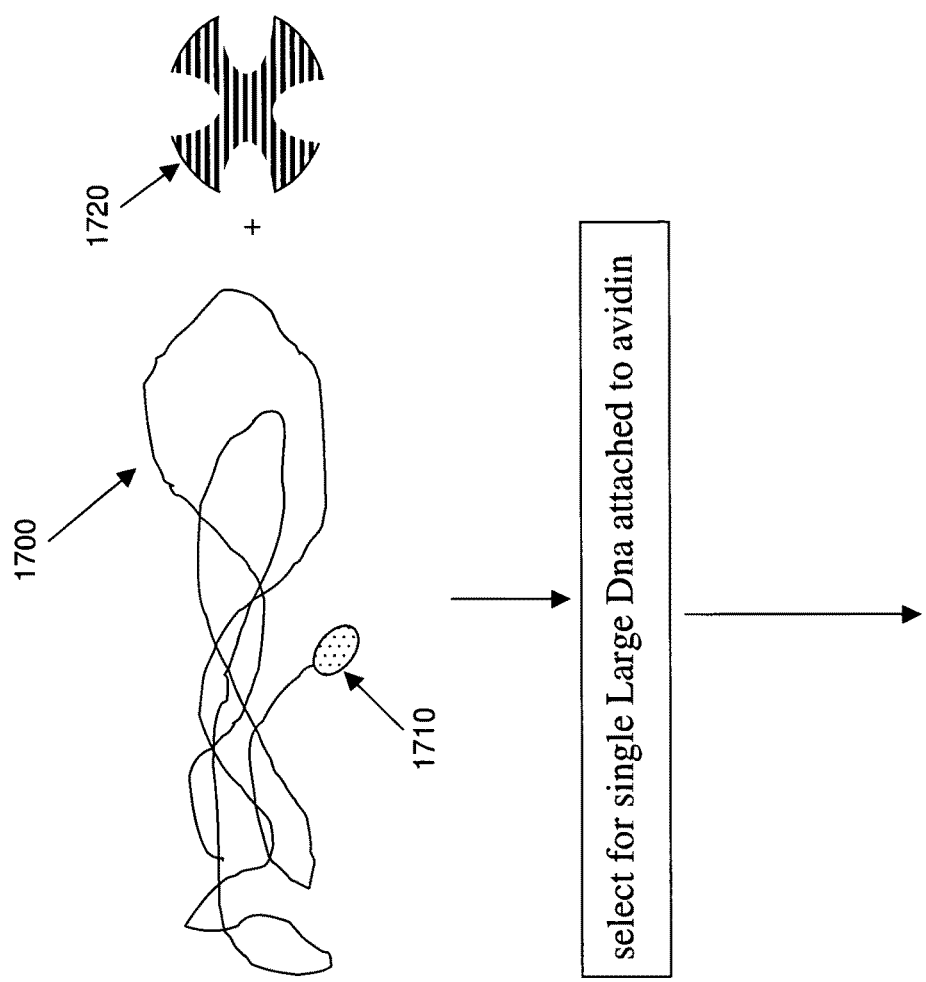

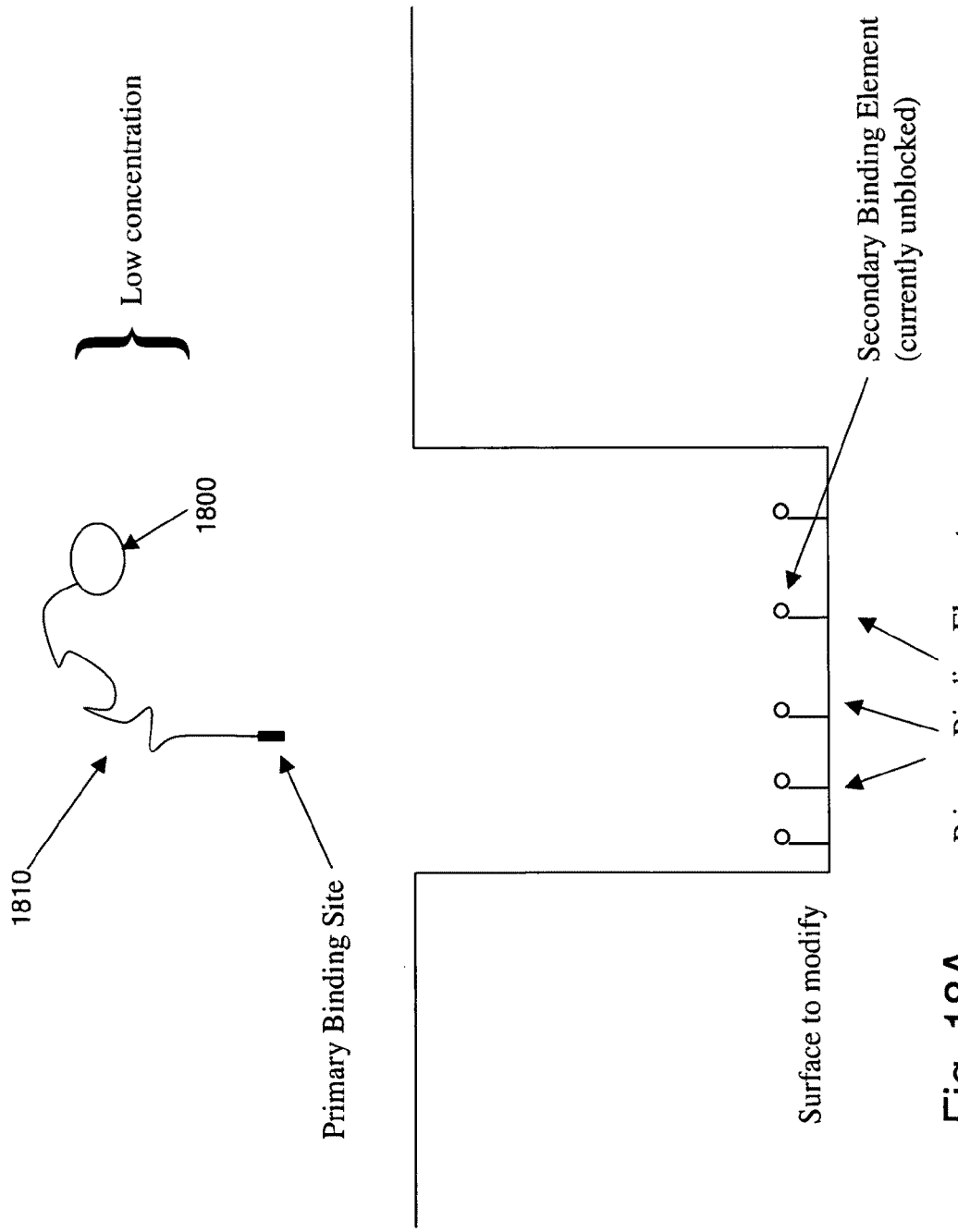

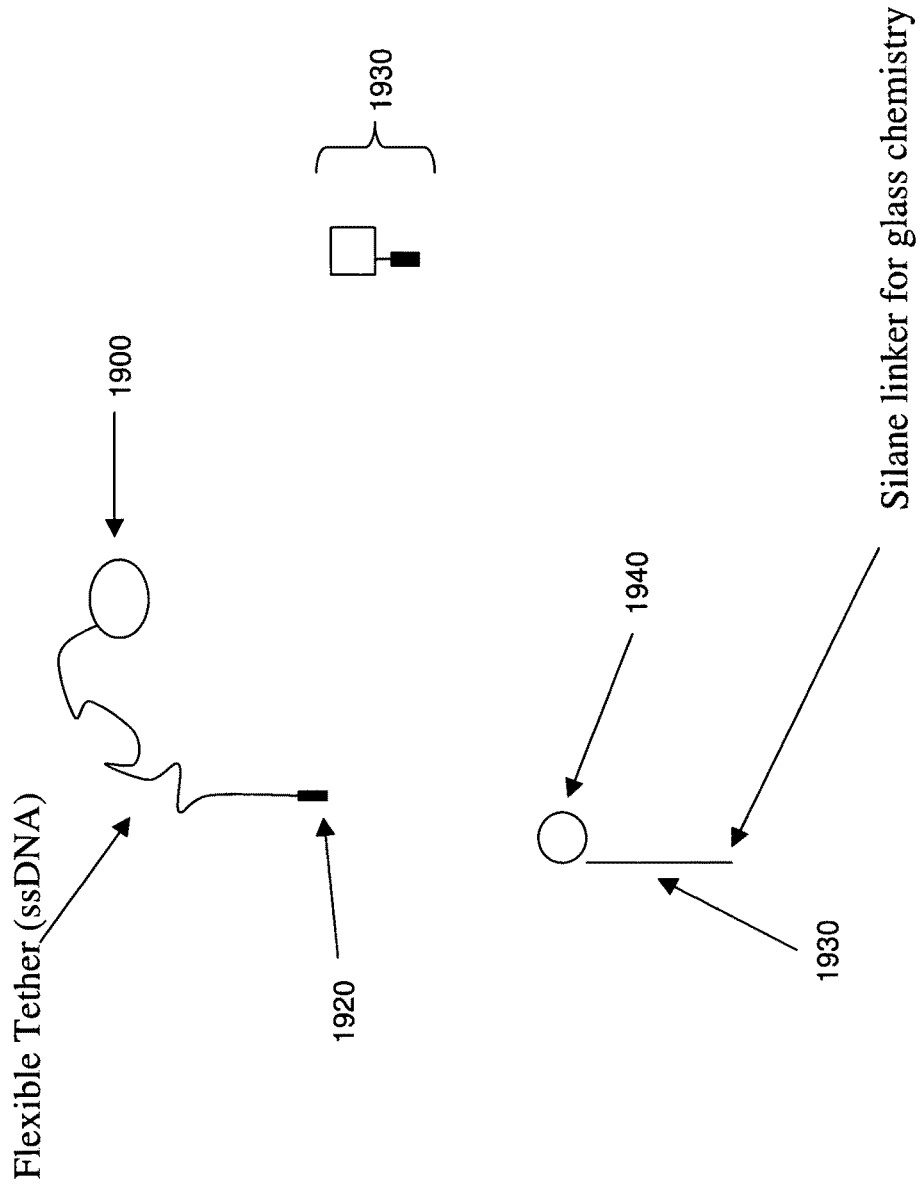

SINGLE MOLECULE LOADING METHODS AND COMPOSITIONS

CROSS REFERENCE TO RELATED APPLICATIONS

This application claims priority to and benefit of: Eid et al., SINGLE MOLECULE LOADING METHODS AND COMPOSITIONS, U.S. Ser. No. 61/072,641, filed Mar. 31, 2008; and Eid et al., SINGLE MOLECULE LOADING METHODS AND COMPOSITIONS, U.S. Ser. No. 61/139,316, filed Dec. 19, 2008. The full disclosures of each of these prior applications are incorporated by reference herein in their entirety.

FIELD OF THE INVENTION

The invention is in the field of single-molecule analyses, such as single molecule DNA sequencing. Methods and compositions that provide non-random distributions of analyte molecules (e.g., enzymes, nucleic acids or other analytes) for single molecule analysis (e.g., single molecule sequencing) are provided.

BACKGROUND OF THE INVENTION

A variety of techniques in molecular biology and molecular medicine now rely on analysis of single biological molecules. Such techniques include DNA and RNA sequencing, polymorphism detection, the detection of proteins of interest, the detection of protein-nucleic acid complexes, and many others. The high sensitivity, high throughput and low reagent costs involved in single molecule analysis make this type of analysis an increasingly attractive approach for a variety of detection and analysis problems in molecular medicine, from low cost genomics to high sensitivity marker analysis.

For example, single molecule DNA sequencing is useful for the analysis of large sets of related DNAs, such as those that occur in a genome. In certain of these methods, a polymerase reaction is isolated within an array of extremely small (typically optically confined) observation volumes that each permit observation of the enzymatic action of individual polymerases in each reaction/observation volume of the array, while the polymerase copies a template nucleic acid. Nucleotide incorporation events are individually detected, ultimately providing the sequence of the template molecule. This approach dramatically increases throughput of sequencing systems, and also dramatically reduces reagent consumption costs—to the point where personalized genomics is increasingly feasible.

The small observation volumes used for single molecule nucleic acid sequencing and other analysis methods are typically provided by immobilizing or otherwise localizing the polymerase (or other) enzyme within an optical confinement reaction/observation region, such as an array of extremely smalls wells as in an array of Zero Mode Waveguides (ZMWs), and delivering a template, primers, etc., to the reaction region. For a description of ZMW arrays and their application to single molecule analyses, and particularly to nucleic acid sequencing, see, e.g., "Selective aluminum passivation for targeted immobilization of single DNA polymerase molecules in zero-mode waveguide nanostructures" (2008) Korlach et al. *Proceedings of the National Academy of Sciences U.S.A.* 105(4): 1176-1181; "Improved fabrication of zero-mode waveguides for single-molecule detection" (2008) Foquet et al. *Journal of Applied Physics* 103, 034301; "Zero-Mode Waveguides for Single-Molecule Analysis at High Concentrations" Levene et al. *Science* 299:682-686; published U.S. patent application No. 2003/0044781; Eid et al. (2008) "Real-Time DNA Sequencing from Single Polymerase Molecules" *Science* DOI: 10.1126/science.322.5905.1263b; and U.S. Pat. No. 6,917,726, each of which is incorporated herein by reference in its entirety for all purposes.

One difficulty in performing single molecule analyses occurs in loading the reaction/observation region of single molecule analysis devices with the molecules of interest (e.g., template or other analyte and/or enzyme). Loading two or more molecules of interest into a ZMW or other small observation volume tends to complicate any analysis of signals observed from double (or more than double)-loaded region. This is because two (or more) sets of signals may simultaneously be observed from the ZMW or other observation volume, meaning that the signals from the ZMW would have to be deconvoluted before data from the observation region could be used. More typically, data from double(+) loaded ZMWs can be recognized by various data analysis methods, and data from mis-loaded ZMWs or other relevant observation volumes is simply discarded.

To reduce the incidence of multiple molecule loading events in the relevant reaction/observation volume(s) of the array, it is typical in the art to substantially "under-load" the array with the analyte molecules of interest. Random distribution of molecules into the array results in one or fewer molecules being loaded into most reaction/observation volumes when fewer than 37% of all observation volumes are loaded. This type of loading is referred to as "Poisson-limited" analyte loading, meaning that few enough molecules are added to the array so that a Poisson-style random statistical distribution of the analytes into the array results in one or fewer analytes per observation volume in most cases. In the ZMW context, state of the art yields for single-molecule occupancies of approximately 30% have been obtained for a range of ZMW diameters (e.g., 70-100 nm). See, Foquet (2008), above. For this degree of loading, about 60% of the ZMWs in a typical ZMW array are not loaded (e.g., have no analyte molecules).

While such random distribution methods are effective in ensuring that, in most cases, not more than a single template or enzyme (or other analyte) molecule is loaded in each observation/reaction volume in an array such as a ZMW array, it would be desirable to develop methods and compositions for increasing the template and enzyme loading density of such arrays. Higher loading densities would permit the simultaneous analysis of more analyte molecules in the array, increasing the throughput of such systems, while simultaneously decreasing analysis costs. The present invention provides these and other features that will be apparent upon complete review of the following.

SUMMARY OF THE INVENTION

The invention provides methods and compositions for controlling loading of single analyte molecules, such as nucleic acid templates, into reaction/observation volumes (such as the wells of a ZMW). These methods and compositions are useful for increasing the throughput and efficiency of single molecule analysis systems. Basic approaches that are provided include: creating a single binding site for an analyte in the reaction or observation volume; removing excess binding sites via catalytic or secondary binding methods; adjusting the size or charge of the analyte; packaging or binding the analyte molecules within (or on) a particle (e.g., within a viral capsid), where a single such particle fits into the relevant observation volume (due to size or charge of the particle and/or observation volume); using non-diffusion limited loading; controllably loading the analyte (e.g., using microfluidic or optical or electrical control); sizing or selecting charges in the observation volumes (e.g., the sizes of ZMWs in an array) to control which analytes will fit (spatially or electrostatically) into which array wells or well regions, iterative loading of analyte, e.g., by masking active sites between loading cycles, enriching the activity of the analytes that are loaded, using self-assembling nucleic acids to sterically control loading, using ribosome display to control loading and provide a base for analyte screening, adjusting the size of the reaction/observation volume; and many others. The methods and compositions provide for the possibility of completely loading single molecule array reaction sites (instead of about 30% of such sites as occurs in the prior art using random "Poisson limited" loading methods) with single analytes, and also provides for control over size, charge and/or location features for both array wells and analyte locations.

Accordingly, the invention provides methods of distributing a population of target molecules into a plurality of size confined reaction or observation regions. Target molecules can optionally comprise nucleic acids, proteins, and/or enzyme-substrate complexes. The methods include providing a structure (e.g., a ZMW, planar substrate, small well array, or the like) comprising the size-confined reaction or observation regions and providing the population of target molecules to be distributed. The methods include adjusting the size of the confined reaction or observation regions by adding at least one sizing moiety to individual reaction or observation regions, such that a selected number of target molecules will fit into the resulting size-adjusted regions. Alternately, the size of individual target molecules of the population can be adjusted by linking at least one sizing moiety to individual target molecules, creating a population of sizing moiety-linked target molecules (e.g., particles linked to an analyte of interest). The sizing moieties are of sufficient size, relative to the size-confined reaction or observation regions, so that only a selected number of sizing moieties, e.g., less than 10 moieties, less than 5 moieties, or, e.g., about one moiety, will fit into the size confined regions. The sizing moieties can fit partly or fully into the region; the relevant determinant is delivery of the target molecule portion to the region. The methods thus include loading the target molecules into the regions, whereby a selected number of target molecules can fit into each region, thus distributing the population of target molecules into the plurality of size confined regions. The methods optionally include selecting the sizing moiety or configuring the reaction region, so that a single sizing moiety will fit into the reaction region. Optionally, the sizing moieties or target molecules can comprise a selected charge, which can be used to electrostatically control loading.

The size-confined regions can individually comprise or be present within an individual well of an array, or in a size-delimited substrate, e.g., a selected portion of a planar or other substrate. For example, the size-confined regions can be present in an optically confined region, e.g., a reaction or observation region of a ZMW. Preferably, the population of target molecules is distributed into size-confined regions (e.g., wells) of an array such that at least 38% of the size-confined regions (e.g., wells) of the array are occupied by only one target molecule. For example, the population of target molecules can be distributed into wells of the array such that at least 50%, or at least 75% or more of the wells of the array are occupied by only one target molecule. Optionally, the methods include selecting the sizing moiety or configuring the reaction region, in such a manner that a single sizing moiety will fit into the size-confined reaction region.

A sizing moiety is a moiety of a selected size that can be used to regulate entry of linked target molecules into a size-confined region. Typically, the sizing moieties can comprise one or more particles, e.g., beads, metal particles, or nanoparticles, or one or more polymers (e.g., one or more PEG, cross-linked polymers, dendritic polymers, hyperbranched polymers, starred polymers, dendrimers, dendrons, nucleic acids, DNA origami, polypeptides, or the like). In addition, sizing moieties can comprise a polysaccharide, polyethylene glycol (PEG), poly(lactic acid), poly(glycolic) acid, hyaluronic acid, a ribosome, a ribosome polypeptide, or a type 1 collagen protein. In certain embodiments, sizing moieties can comprise viral capsids, e.g., viral capsids that include at least one recombinant or modified coat protein that comprises polymerase activity.

The methods provided by the invention can be used to distribute polymerases to size-confined regions. In such embodiments, the sizing moieties can comprise polymer tails linked to each polymerase, and protease cleavage sites can be located between each polymer tail and polymerase, e.g., to permit the release of the polymerase from the sizing moiety. Optionally, the sizing moieties can be ribosomes that each bind a target polymerase during translation. A target population of polymerases in size-confined regions can optionally constitute a ribosome display library of polymerase variants, such that different polymerase variants are present in different regions. Relatedly, the methods can further comprise screening the polymerases of the ribosome display library for one or more properties of interest. The polymerases of the library can optionally reverse transcribe or sequence a nucleic acid encoding the polymerase. This nucleic acid is at least initially associated with a ribosome that is at least initially associated with the polymerase.

In one embodiment, the sizing moieties expand upon binding to structures in the confined regions to prevent additional sizing moieties from entering into the confined regions. This can occur, e.g., where the sizing moiety is initially approximately spherical, and flattens upon entry into or binding within or proximal to the sizing region. Desirably, the sizing moieties and confined regions are sized such that a single sizing moiety can fit into each of the plurality of confined regions, thereby providing for delivery of a single target molecule into the size delimited region. As noted, individual sizing moieties can fit fully or only partially into each of the plurality of confined regions to provide the target molecule (e.g., nucleic acid or protein), into the region. In one convenient embodiment, the sizing moiety linked target molecules are flowed into the reaction/observation regions.

Sizing moieties can optionally form a size-exclusion matrix that prevents more than a single target molecule from entering an analysis or fixation region of the size-confined reaction or observation region. The fixation region can comprise, e.g., functionalized silicon, gold or aluminum; the functionalized region can comprise, e.g., one or more binding partners; and the sizing moieties or analytes can comprise, e.g., one or more cognate binding partners. In one useful embodiment, the sizing moieties can be removed from the size confined reaction or observation region subsequent to loading of the single target molecule.

Individual sizing moieties can be covalently or non-covalently linked to walls of the confined regions or to individual target molecules. For example, the target molecules to which the sizing moieties are linked can be polymerase enzyme molecules that comprise a reactive or binding moiety, such as a SNAP tag, that permits attachment of the sizing moiety. Individual sizing moieties optionally can be cleaved from the individual target molecules or walls after the loading step by exposing an individual sizing moiety-target molecule complex to, e.g., a change in pH, a change in salt conditions, addition of a competition moiety, light, heat, a protease, an endonuclease, an exonuclease, and/or an electromagnetic field.

The methods of distributing a population of target molecules into a plurality of size-confined regions can also include attaching a sizing moiety that is linked to a target molecule within or proximal to the reaction/observation region to fix the location of the target molecule within or proximal to the region. The methods can optionally further include attaching at least one target molecule within or proximal to the confined region and cleaving at least one sizing moiety from the target molecule to release the target molecule from the sizing moiety. The method can also include loading a second population of sizing moiety linked target molecules into the confined regions, e.g., with the second population including target molecules that are different from the first target molecules (e.g., where the first target molecules are attached within the regions). For example, the first target molecules delivered and optionally attached within the confined regions can be polymerase molecules, while the second population of target molecules can include nucleic acid templates to be copied by the polymerase molecules in the regions (e.g., where the confined regions are each individually comprised within a zero mode waveguide). The plurality of confined reaction or observation regions can optionally be formatted into an array comprising additional reaction or observation regions, and a secondary loading step can load additional sizing moiety-linked target molecules into the additional confined reaction or observation regions.

A plurality of size confined reaction or observation regions can optionally include a subset of regions that are pre-loaded with a single polymerase molecule, a subset of regions members that lack polymerase molecules, and sizing moiety-linked target molecules that comprise one or more template nucleic acids. In such embodiments, the methods can include initiating copying or transcription of the template nucleic acid by the polymerase, followed by loading of additional polymerase protein molecules into at least some of the members that lacked polymerase, resulting in secondarily loaded confined observation or reaction regions comprising secondary polymerase proteins. A secondary loading step can then be performed in which additional sizing moiety linked template nucleic acids are loaded into the secondarily loaded regions.

In a related aspect, the invention comprises methods of distributing a population of nucleic acid or other analyte molecules into a plurality of wells in a small well array. The methods include providing a small well array that comprises the plurality of wells and providing a population of particles that bind or package a population of analyte molecules. In these methods, the plurality of wells in the array are individually configured to receive a single particle from the population of particles, such that delivering the population of particles into the plurality of wells distributes the population of analyte molecules to the plurality of wells.

In one example, the invention provides methods of distributing a population of analyte molecules (e.g., nucleic acids, polymerase molecules, etc.) to a plurality of wells in a zero-mode waveguide (ZMW). The methods include providing a zero-mode waveguide that comprises a plurality of wells, providing a population of particles that can bind or package a population of analyte molecules, and delivering the population of particles to which the nucleic acids are bound or packaged into wells of the ZMW. Optionally, the plurality of wells can be individually configured to each receive a single particle. Optionally, the particles can be sized such that a single particle can fit in each of the plurality of wells.

In the embodiments, particles used to distribute nucleic acids or other analytes to the wells in a size delimited region, ZMW, or other array can optionally comprise viral capsids, e.g., capsids derived from a lambda phage, a phi29 phage, a T7 phage, a T4 phage, a virus of the Myoviridae family, a virus of the Siphoviridae family, a virus of the Podoviridae family, or a capsid that comprises at least one recombinant coat protein that comprises polymerase activity. Particles can optionally comprise a self-assembled DNA structure. For example, self-assembled DNA structures used in the methods can optionally comprise long DNAs, DNAs comprising a large radius of gyration, plasmids, circular DNAs, DNA origami structures, DNA grids, DNA grids comprising a gold particles, DNA dodecahedrons, Sierpinski triangles, DNA octahedrons, or polycatenated DNA scaffolds. In certain embodiments, the DNA structure can comprise a single polymerase binding site and/or can be covalently bound to a single polymerase molecule. Alternatively, the particles can individually comprise one or more nanostructure, bead, polymer, polysaccharide, polyethylene glycol (PEG), poly(lactic acid), poly(glycolic) acid, hyaluronic acid, type 1 collagen, ribosome, ribosome polypeptide, or polypeptide. Such particles can be cleaved from the nucleic acid molecules after delivery by exposing individual particle-nucleic acid complexes to any one or more of the conditions described previously.

Delivering a population of particles into the wells of a ZMW can optionally comprise packaging the population of nucleic acids into particles that comprise the viral capsids and distributing the resulting packaged nucleic acids into the plurality of wells in the ZMW. Optionally, the particles can be directionally oriented, e.g., by selectively attaching the particles to the wells of the zero-mode waveguide. Delivering the population of particles to e.g., to the wells of a ZMW or a small well array, can include distributing the particles such that at, e.g., least 38% of the wells, at least 50% or the wells, at least 75% of the wells, or, most preferably, at least 95% or more of the wells of the ZMW or small well array are occupied by one particle. The methods can further include sequencing the nucleic acid molecules by performing a sequencing reaction in the wells of the ZMW or small well array.

Compositions provided by the invention include analysis devices comprising an array of analytes that are arranged in the array by one or more phase determining features in such a manner that single molecules of the analyte are present in each of at least 40% of the analysis regions of the array. The analyte molecules can optionally be, e.g., at least 20 nm, at least 30 nm, at least 40 nm, or, preferably, at least 50 nm apart on the array. The phase determining features that arrange the analyte molecules can optionally include an arrangement of wells in the array, an arrangement of ZMWs in the array, a mask that permits access by the analyte to the analysis regions, an arrangement of particles in the array, the particles comprising binding moieties that bind to the analyte, and/or an arrangement of binding sites located at least 50 nm apart in the array, which binding sites are configured to bind individual analyte molecules.

Other compositions that are provided by the invention include a zero-mode waveguide (ZMW) or other small well array that comprises a plurality of wells, and a population of particles that bind or package a population of analyte that has been distributed into the plurality of wells. Optionally, the wells of the ZMW or other array (or an observation/reaction region in the ZMWs) can be configured to receive only one particle. Optionally, at least 38% of the wells, at 50% of the wells, at least 75% of the wells, or, most preferably, 95% or more of the wells of the ZMW or small well arrays of the invention can be occupied by one particle. The particles in the wells can optionally comprise one or more bead, nanostructure, or polypeptide, or viral capsid recited above.

The invention also provides methods of producing a non-random distribution of single analyte molecules in analysis regions of an array, e.g., analysis regions within wells of a small well array. These methods include selectively distributing the analyte molecules into the analysis regions, such that at least 38% of the regions are occupied by one analyte molecule, fewer than 5% of the analysis regions (and, preferably, fewer than 1%, or even fewer than 0.1%) are occupied by more than one analyte molecule, and fewer than 62% of the analysis regions are occupied by fewer than one analyte molecule. The non-random distribution of nucleic acid molecules in the analysis regions can optionally be a non-Poisson distribution. In one useful embodiment, these methods can be used to distribute nucleic acid and/or polymerase molecules to target wells of a zero-mode waveguide (ZMW). The nucleic acid molecules in the target wells can optionally be sequenced.

The arrays to which the analyte molecules are distributed can optionally comprise one or more phase determining features that result in a patterned distribution of the analyte molecules in the analysis regions of the arrays. For example, one such phase determining feature can include spacing the analyte molecules with a regular or selected spacing of at least 50 nm on center. Optionally, the arrays used in these methods can be configured to comprise a subpopulation of decoy wells, which selectively receive small nucleic acids, in addition to the target wells Non-random analyte molecule distribution to analysis regions in an array can optionally include configuring selected analysis regions of the array to receive, at most, one particle, and delivering a population of particles that comprise, bind, or package the analyte molecules into the target regions, in a manner such that at least 38% of the regions are occupied by the particles. The population of particles can optionally be delivered to the analysis regions of the array such that at least 50%, at least 75%, or, most desirably, at least 95% or more of the analysis regions are occupied by the particles. The particles used to deliver the analytes can optionally comprise any one or more of the moieties described above or any viral capsids described herein, including viral capsids comprising one or more recombinant or modified coat proteins that comprise polymerase activity. Such a coat protein can optionally comprise a viral coat protein sequence fused to a polymerase, with the resulting fusion protein being bound to a nucleic acid template packaged by the fusion protein.

Producing a non-random distribution of single analyte molecules in analysis regions of an array can also comprise configuring or providing selected analysis regions of the array to receive, at most, about 1 particle per region and delivering said particles to said analysis regions. The particles can comprise reactive group A, and the analysis regions can comprise reactive group B at a low density. Delivering particles to the analysis regions permits a single reactive group A to bind a single reactive group B in an individual analysis region. Unreacted A and B groups can be quenched, and the particles can be released, leaving approximately a single analyte binding site in the individual analysis regions, e.g., a binding site formed from the A or the B group, or both, or from release of the particle. Single analyte molecules can then be bound to the single analyte binding sites in the array. Optionally, analyte molecules can be loaded onto the onto the analysis regions of the array in a high concentration, thereby binding more than 70% of the available binding sites in the array, and any unbound analyte molecules can be washed from the array. Alternatively or additionally, an analyte molecule can optionally be part of an analyte complex that comprises a polymerase molecule and a template molecule, wherein the polymerase or the template comprises a cognate binding element that binds to the single analyte binding site.

Selectively distributing analyte molecules to an array to produce a non-random distribution of particles can optionally comprise distributing a population of bi-functional particles, each comprising an analysis region binding moiety, an analyte binding moiety, and a masking domain, into the array. The bi-functional particles can bind within the analysis binding regions, releasing the masking domain from the bound particles. The analyte molecules can then bind to the analyte binding moieties. The masking domain present on each bi-functional particle can optionally be a large nucleic acid that inhibits binding of more than a single particle in the analysis region. The analysis region binding moiety optionally includes a first tag and the analyte binding moiety comprises a different second tag, where the masking domain is released by photoactivation or enzymatic cleavage. Optionally, the analyte molecule is a polymerase comprising a third tag complementary to the second tag.

Producing a non-random distribution of analyte molecules in analysis regions of an array or ZMW can optionally include distributing a nucleic acid mask into individual analysis regions that comprise oligonucleotide positioning features that position the nucleic acid mask within the individual analysis regions. An individual analysis region can be exposed through a small hole in a selected region of the mask, the oligonucleotide positioning features can hybridize to the mask, and a single analyte molecule can bind the analysis region through the small hole in the mask. Optionally, the mask can be removed or degraded subsequent to binding of the analyte molecule.

Optionally, the non-random distribution of analyte molecules in the analysis regions can be produced by providing a population of nucleic acid particles individually comprising a single binding moiety and providing a population of adaptors that can individually bind to the binding moiety and to an individual the analysis region. Desirably, the nucleic acid particles are large enough relative to the analysis regions to effectively inhibit binding of more than one particle to one analysis region. Binding the population of nucleic acid particles and the adaptors to the analysis regions can be followed by the cleavage of the nucleic acid particles, which cleavage exposes individual single adaptors bound to within the analysis regions. Analyte molecules can then be advantageously bound to single adaptors.

Optionally, individual nanostructures comprising a binding site for the analyte molecule can be fabricated in or distributed into the analysis region in such a manner that binding of more than a single analyte molecule to the nanostructure is sterically inhibited. For example, a nanostructure can optionally be a nanoparticle that is small enough to inhibit binding of more than a single analyte molecule comprising a polymerase to the nanoparticle. The nanostructure can optionally be deposited electrochemically, and growth of the nanostructure can be terminated while the nanostructure is small enough to sterically inhibit binding of more than a single analyte molecule to the nanoparticle.

Fabricating nanostructures in analysis regions can optionally comprise forming a monolayer of small nanoparticles in individual analysis regions and coalescing the small nanoparticles in the individual regions into larger nanoparticles in the regions, such that at least one larger nanoparticle is formed in at least one individual region. Optionally, an array of small wells comprising the analysis regions can be provided, and a micelle comprising a nanostructure of interest, which micelle is sized such that it centers the nanostructure within the well, can be distributed to each of the small wells. Alternately, fabricating the nanostructure in the region can include dispersing particles in a photopolymerizable monomer, delivering the resulting monomer-particle solution to the region, photopolymerizing the monomer in the region, and fixing the particle in the region.

Optionally, a nanostructure that is less than about 100 nm in at least one dimension can be suspended in a negative tone photoresist. The photoresist can be spun onto a substrate, and depressions can be formed in the photoresist via lithography. The depressions can leave photoresist pillars that are less than about 200 nm in at least one cross-sectional dimension, and the depressions can then be clad with a cladding material. Optionally, the cladding material can be aluminum, and the nanostructures can comprise gold functionalized with one ore more binding sites that bind to the analyte molecule. In other embodiments in which photoresist pillars are formed during the fabrication of the nanostructures, the photoresist pillars can optionally be removed in a manner that deposits the nanostructures suspended in the photoresist onto the substrate within wells that comprise walls of the cladding material.

Fabricating the nanostructure in the analysis region can also or alternately optionally include suspending a nanostructure that is less than about 100 nm in at least one dimension in a negative tone photoresist, distributing the suspended nanostructure into one or more wells in a small well array, cross linking the photoresist in the wells, removing the resist from regions between the wells, and removing the resist in the wells. The wells can optionally be of a sufficiently small diameter such that the cross linking illumination light displays quantum confinement in a region at the bottom of the wells, limiting said cross linking to a region at or near the bottom of the wells. Cross linking the photo resist to the wells can then include exposing the wells to cross linking illumination light from the bottom of the wells.

Optionally, single nanostructure islands or nanostructure dots that bind a single analyte molecule can be deposited into single analysis regions of an array. The analysis regions of the array can optionally comprise regions proximal to the dots or islands, or they can comprise ZMWs that are formed around the dots or islands. Optionally, an island or dot can comprise Au—S'$(CH_2)_x(C_2H_4O)_y$-biotin, the analyte molecule can comprises avidin-polymerase, and the analyte can be bound to the island or dot through the binding of the Avidin moiety to the biotin moiety. Fabricating a nanostructure island or dot can include cleaning a fused silica or synthetic quartz wafer, applying a resist adhesion promoter to the wafer, spin coating the wafer with a positive tone chemically amplified resist, baking the positive tone chemically amplified resist, performing e-beam lithography on the wafer to form a pattern in the resist, baking the resist after lithography, developing the resist, performing photoresist descum, depositing metal to form dots or islands, and deresisting the wafer.

A nanostructure island or dot is can optionally be fabricated in place using, e.g., electron beam lithography, nanoimprint pattern formation, high-aspect physical vapor deposition or chemical vapor deposition. For example, a substrate comprising a base material, a cladding material, an aspect buffer control layer, and a resist can be provided, an array of wells, the wells extending through the resist, cladding material and aspect buffer control layer to the base layer can be formed, and a masking film over the array can be formed to produce a mask that partially extends across the tops of the wells of the array, restricting access to a small diameter region in the bottom of each of the wells. Nanostructures in the small diameter regions can be deposited, and the mask can subsequently be removed, thereby providing an array of wells that each comprise a single nanostructure that is configured to attach a single analyte molecule in the well's analysis region. In other embodiments, a substrate comprising a base material, a cladding material, an aspect buffer control layer, and a resist can be provided, and an array of wells that extending through the resist, cladding material and aspect buffer control layer to the base layer can be formed. A masking film can then be deposited over the array, thereby producing a mask that partially extends across the tops of the wells of the array, restricting access to a small diameter region in the bottom of each of the wells. Subsequently, nanostructures can be deposited in the small diameter regions, and the walls of the wells can be removed to provide an array of nanostructure configured to attach a single analyte molecule in an analysis region of the array.

Alternatively, forming or depositing a nanostructure island or nanostructure dot that binds a single analyte molecule in an analysis regions of the array can include permitting an imperfect self-assembled monolayer (SAM) to form in wells of a small well array or on the surface of a substrate. An island can then be formed through a selected region of the SAM via atomic layer deposition. Other methods to form a nanostructure in an analysis region include forming a multi-film stack on a substrate, forming a well array through multiple layers of the multi-film stack, depositing a spacer film over the well array, planarizing the multi-film stack to remove at least one layer of the multi-film stack between wells, and removing portions of the spacer film within the wells, thereby producing nanostructures within the wells of the array. Optionally, a multi-film stack can be formed on a substrate, an array of structures can be formed through multiple layers of the multi-film stack, and a spacer film can be deposited over the array. The multi-film stack can then be planarized to remove at least one layer of the multi-film stack, and the spacer film can be etched to produce nanostructures on the substrate.

Methods to produce a non-random distribution of single analyte molecules in analysis regions of an array can optionally include fabricating a nanostructure array, wherein the analyte molecules are subsequently bound to the nanostructures, and subsequently forming the analysis regions to encompass the nanostructures of the array. Fabricating the nanostructure array can optionally include forming an array of metal nanostructures on a substrate. For example, a cladding material can be applied to the array, the cladding can be spin coated with a resist layer, and regions of the resist proximal to the metal nanostructures can be removed. The cladding in these regions can then be etched to expose the metal nanostructures, thereby forming an array of small wells in the cladding.

In other embodiments, single analyte molecules can be distributed to analysis regions in a non-random manner by fabricating a small well array, wherein the floor of the wells comprises a substrate material and walls of the wells comprise a cladding material that is different from the substrate material. The wells can then be coated with an analyte binding material, cladding material can be etched to increase the diameter of the wells, leaving the analyte binding material approximately in the center and on the bottom of individual wells in a patch of analyte binding material that is sufficiently small in size to inhibit binding of more than one analyte molecule to the patch of binding material. Analyte molecules can then be bound to the patch of analyte binding material in the wells.

Alternatively, a solvent comprising a low concentration of an analyte binding moiety that binds to the analyte and to analysis regions can be deposited into an analysis region. The solvent can be evaporated to deposit the analyte binding moiety in the analysis region, and the analyte can then be bound to the analyte moiety in the analysis region to produce a non-random distribution of analyte molecules. In one useful example, the analysis region can be a zero mode waveguide (ZMW) and evaporation of the solvent can deposit the analyte binding moiety in approximately the center of the ZMW.

Other methods of selectively distributing analyte molecules can optionally include applying a coating in a solvent to the analysis regions, evaporating the solvent while rotating the array, thereby leaving a portion in the center of the analysis region that is free of the coating. A single analyte molecule can then be bound to the center of the analysis region Desirably, the uncoated center portion is small enough that binding of more than 1 selected analyte molecule to the center region is sterically inhibited.

Single analyte molecule can optionally be controllably transported into each of the analysis regions to produce a non-random distribution of analyte molecules in analysis regions. For example, this can include fluidly coupling a plurality of analysis regions of the array to at least one source of the analyte through at least one microscale channel and controlling the flow between the source and the analysis region with a control module that gates or regulates flow from the source to the analysis region. A control module can optionally be operably connected to a sensor configured to sense flow of an analyte molecules from the channel into the analysis region. Optionally, the analyte can be optically labeled, the sensor can comprise an optical sensor, and the controller can controls a valve between the source and the analysis region. Optionally, the sensor can comprise a conductivity sensor that detects passage of an analyte molecule past the sensor, and each analyte molecule can be coupled to a dielectric nanoparticle. Single analyte molecules can optionally be transported into individual analysis regions using a gradient optical force, or an electrical trap. Controllably transporting an analyte molecule into an analysis region can optionally preventing the binding of additional analyte molecules in the analysis regions.

Optionally, selectively distributing single analyte molecules into analysis regions can include controllably transporting single that comprise a binding site for the analyte molecule into each of the analysis regions. Steric inhibition can thereby prevent the binding of more than 1 analyte molecule to the particle. Alternately, the particle can comprise a single analyte molecule binding site. A single particle can be controllably transported into an analysis region via, e.g., a fluidic control, an optical gradient, and/or an electrical trap. An array of optical traps with a trap to trap spacing that matches spacing between analysis regions can optionally be used to controllably transport single to analysis regions. A plurality of single particles can optionally be transported in parallel to a plurality of analysis regions.

Single analyte molecules can optionally be randomly distributed into the analysis regions, such that fewer than 60% of the analysis regions of the array are occupied by an analyte molecule. Regions comprising the analyte molecules can be detected and masked, and additional analyte molecules can be added to additional analysis regions that are not masked, such that more than 62% of the analysis regions are occupied by an analyte molecule. For example, following detection and masking, further analyte molecules can be added to further analysis regions that are not masked, such that more than at least about 75% of the analysis regions are occupied by an analyte molecule.

Selectively distributing analyte molecules can optionally include providing an analyte molecule of interest comprising a detectable label and a photoactivatable binding group, transporting the analyte molecule into an analysis region, photoactivating the binding group, permitting the resulting photoactivated binding group to bind within the analysis region, detecting immobilized analyte molecules in the analysis region by detecting the label, and reducing illumination to the analysis region once binding of the analyte molecule is detected. This embodiment can also be used to deliver plurality of analyte molecules of interest in parallel to a plurality of the analysis regions. Optionally, an additional analyte molecule of interest that comprises the detectable label and photoactivatable binding group can be delivered and bound to an additional analysis region. Optionally, this embodiment can be used to first bind analyte binding moieties to analysis regions. Analyte molecules can then optionally be bound to the moieties. A binding group can optionally comprise, e.g., an unnatural amino acid, a reactive group, a protein ligand, biotin, avidin, or a functionalized particle or bead. Illumination light is carried to the analysis region through a waveguide or directed to the waveguide using a laser, micromirror, or optical train.

Selectively distributing the analyte molecules can optionally comprise randomly distributing labeled analyte molecules to the analyte regions in the array, such that less than 38% of the regions are occupied by one or fewer labeled analyte molecules, and less than 5% of the analysis regions are occupied by more than 1 labeled analyte molecules. The analyte regions of the array that are occupied by the labeled analyte molecules can be identified by detecting the label, and additional analyte molecules can be selectively loaded into unlabelled (e.g., unoccupied) analysis regions of the array. Selectively loading the additional analyte molecules into the unoccupied regions can optionally comprise individually addressing the unlabeled analyte regions with a microfluidic module that selectively controls flow of analyte molecules into the unoccupied analyte regions. Optionally, selectively loading the additional analyte molecules into the unoccupied regions can comprise masking labeled analyte regions and flowing analyte molecules into the unlabeled analysis regions.

Selectively distributing analyte molecules can optionally comprise providing the analysis binding regions of the array such that the analysis regions of the array individually comprise a plurality of analyte binding moieties, binding, e.g., within or proximal to the analysis regions of the array, a population of catalyst molecules or complexes that individually comprise at least one analysis region or proximal region binding domain and at least one catalyst domain, permitting the catalyst to degrade at least one of the plurality of analyte binding moieties, and binding analyte molecules to the array, wherein analyte binding moieties in the analysis regions bind to the analyte molecules. Binding of the catalyst to the analysis region through the analysis region binding domain can optionally protect at least one analyte binding moiety in the analysis region from degradation by the catalyst domain, e.g., due to an inability of the catalysis domain to reach the at least one analyte binding moiety. Optionally, the population of catalyst molecules can exist in an inactive configuration when initially bound to the analysis or proximal regions of the array, and permitting the catalyst to degrade the analyte binding moieties can comprise activating the catalyst molecules. The catalyst molecule can optionally be released from the analysis or proximal region prior to binding of the analyte molecule.

Optionally, the analysis regions can comprise single stranded oligonucleotides comprising terminal benzyl guanine moieties, the catalysis molecule can comprise an exonuclease tethered through a linker to a complementary nucleic acid that is hybridized to at least one of the single stranded oligonucleotides, and the exonuclease can cleave unhybridized oligonucleotides from the analysis region. Optionally, the catalyst molecule can comprise a linker between the catalyst domain and the binding domain and a release site configured to controllably release the catalyst domain after binding of the molecule. For example, the linker can be a flexible linker comprising polyethylene glycol, polyglycine, polyserine, DNA, a polypeptide, or a combination thereof; the catalyst domain can comprise a protease, trypsin, an esterase, a nuclease, an exonuclease, or an endonuclease; and the release site, when present, can comprise a peptide recognition site, a short nucleic acid sequence, a DNA endonuclease recognition sequence, or an ester.

Selectively distributing the analyte molecules can comprise providing the analysis binding regions of the array such that the analysis regions of the array individually comprise a plurality of analyte binding moieties and binding a population of catalyst molecules or complexes that individually comprise at least one analysis region binding domain and at least one catalyst domain to the analysis regions of the array. The catalyst can then degrade at least one of the plurality of analyte binding moieties, such that binding of the catalyst to the analysis region through the analysis region binding domain protects at least one analyte binding moiety in the analysis region from degradation by the catalyst domain. The catalyst molecules or complexes can then be released from the analysis regions, and analyte molecules can be bound to the array through the analyte binding moieties in the analysis regions.

Alternatively, selectively distributing the analyte molecules can comprise binding a plurality of copies of a first at least partially single stranded nucleic acid in the analysis region or forming a plurality of copies of a first at least partially single stranded nucleic acid in the analysis region. A complex comprising the analyte, a single-stranded nuclease and a second at least partially single stranded nucleic acid that is at least partially complementary to the first nucleic acid can be provided to the analysis region, the first and second nucleic acids can be permitted to hybridize, and the nuclease can be permitted to digest unhybridized copies of the first nucleic acid, thereby fixing a single molecule of the analyte in the analysis region. Optionally, a plurality of copies of a first polypeptide binding partner can be bound in the analysis region, providing a complex comprising the analyte, and a complementary polypeptide binding partner and a protease can be provided to the analysis region. The first and second binding partners can be permitted to bind, and the protease can digest unbound copies of the first binding partner, thereby fixing a single molecule of the analyte in the analysis region.

A polyfunctional moiety can optionally be bound to the analyte to produce a polyfunctional moiety/analyte complex that permits the complex to be bound to an analysis region that comprises a plurality of cognate functional groups that bind to multiple sites on the polyfunctional moiety. The polyfunctional moiety can optionally comprise, e.g., a dendrimer or a dendron, comprising multiple terminal groups, each terminal group comprising a single functional moiety, wherein each of the functional groups binds to individual cognate groups in the analysis region, wherein the terminal groups for a single dendrimer or dendron bind to a majority of cognate groups present in the analysis region.

An array of analyte molecules or analyte binding molecules can optionally be formed and the molecules can then be transferred or copied into an array of small wells comprising the analysis regions.

Analyte molecules can optionally be activity enriched before distributing them into the analysis regions. For example, the analyte molecules can be or comprise polymerase molecules. Activity enrichment of the polymerase can include binding polymerase molecules to a template nucleic acid, separating unbound polymerase molecules from the template-bound polymerases, thereby removing polymerase molecules that lack template binding activity from polymerase molecules that comprise template binding activity. The template bound polymerase molecules that can copy the template can also dissociate from the template, thereby forming released active polymerase molecules. (Polymerase molecules that lack template copying activity remain bound to the template.) Alternately, activity enrichment of the polymerase molecules can include removing polymerase molecules that lack template binding activity from polymerase molecules that comprise template binding activity, as described above, and permitting template bound polymerase molecules to copy the template. Based upon production of an at least partial copy of the template, the active polymerase molecules can be separated from inactive molecules.

In another aspect, the invention provides compositions which include a zero-mode waveguide (ZMW) or small well array that comprises a plurality of wells and a population of template nucleic acid molecules that is distributed into the plurality of wells such that at least 38% of the wells are occupied by only one template nucleic acid molecule. Optionally, 38% of the wells, or, preferably, 50% or more of the wells of the ZMW can be occupied by particles that bind or package the template nucleic acid molecules. The particles in the composition can optionally comprise one or more of the moieties described above, and can optionally be covalently or non-covalently attached to the polymerase, nucleic acid, or both, via a cleavable linker that can be selectively cleaved by exposure to, e.g., a change in pH, a change in salt conditions, addition of a competition moiety, light, heat, a protease, an endonuclease, an exonuclease, or an electromagnetic field. The particles that can optionally comprise viral capsids, e.g., as described above. The ZMW of the composition can comprise a subpopulation of decoy wells that are configured to selectively receive a population of contaminating nucleic acids smaller in size than the template nucleic acid molecules.

In addition, the invention provides methods of distributing a population of heterogeneously sized nucleic acid or other analyte molecules to an array of wells. The methods include providing the array of wells, e.g., an array that comprises a population of small wells and a population of large wells, wherein the small wells are smaller in diameter or depth than the large wells. The methods include providing a population of heterogeneously sized e.g., nucleic acid molecules that includes a subpopulation of short molecules and a subpopulation of long molecules. The methods also include distributing the population of analyte (e.g., nucleic acid) molecules to the array, such that the subpopulation of short molecules is preferentially delivered into the small wells and the subpopulation of long molecules is preferentially delivered into the large wells.

Optionally, the wells can be ZMWs and the array can comprise an array of ZMWs. Optionally, the small wells can be decoy wells that preferentially accept small contaminants, e.g., small nucleic acids from the population and the large wells can be target wells that preferentially accept large target analytes such as large nucleic acids. The array used in the methods can optionally be configured to retain short molecules in the small wells and long molecules in the large wells. The short molecules can optionally comprise contaminant molecules and the long molecules can optionally comprise target molecules. The methods can optionally include sequencing the long template molecules, e.g., by performing sequencing reactions in the large wells.

Distributing the population of nucleic acid molecules into an array of wells can optionally comprise flowing the nucleic acids onto the array. Optionally, distributing the population of nucleic acid molecules into an array of heterogeneously sized wells can comprise first flowing the nucleic acids over the large wells, which retain the long molecules, and subsequently over the small wells, which retain the short molecules. The large and small wells can optionally be arranged in a selected pattern on the array, thereby determining which portions of the array preferentially comprise the long and short molecules.

Methods of distributing a population of heterogeneously sized nucleic acid molecules to an array of wells can optionally comprise separating the long and short nucleic acid molecules prior to their distribution to the wells. Optionally, the population of long molecules can be delivered to the array first, followed by delivery of the short nucleic acid molecules. The methods can further comprise sequencing the nucleic acid molecules in the wells and assembling the resulting sequences into contigs. Assembling the contigs can include first assembling sequences of long nucleic acid molecules and then assembling sequences of said short nucleic acid molecules.

Other compositions provided by the invention include a zero-mode waveguide (ZMW) that comprises a plurality of wells. The wells of the ZMW of the compositions comprise a population of target wells and a population of decoy wells, which are smaller than the target wells. The decoy wells can optionally be configured to preferentially receive short template nucleic acids and the target wells can optionally be configured to preferentially receive long nucleic acids. The decoy or target wells can be preferentially located in one region of the ZMW. Optionally, the decoy and target wells can be distributed into several regions of the ZMW. The target and decoy wells can occupy substantially non-overlapping regions of the ZMW. Optionally, the target and decoy wells can occupy substantially overlapping regions of the ZMW.

The invention also provides a particle bound to a polymerase-template complex. Any of the features noted above can apply to this embodiment, e.g., the particle can be a magnetic bead. For example, the magnetic bead can include an affinity moiety such as a Ni-NTA moiety bound to the polymerase template complex, e.g., where the polymerase comprises a cognate affinity moiety such as a recombinant polyhistidine sequence. The polymerase can further comprises features that permit cleavage from the bead, such as a recombinant endonuclease site proximal to the polyhistidine sequence.

Combinations of these embodiments are expressly a feature of the invention. Kits comprising the components noted herein are also a feature of the invention.

BRIEF DESCRIPTION OF THE FIGURES

FIG. 19 provides further details regarding example features of the moieties used for catalyst scouring.

DETAILED DESCRIPTION

Figure 1:
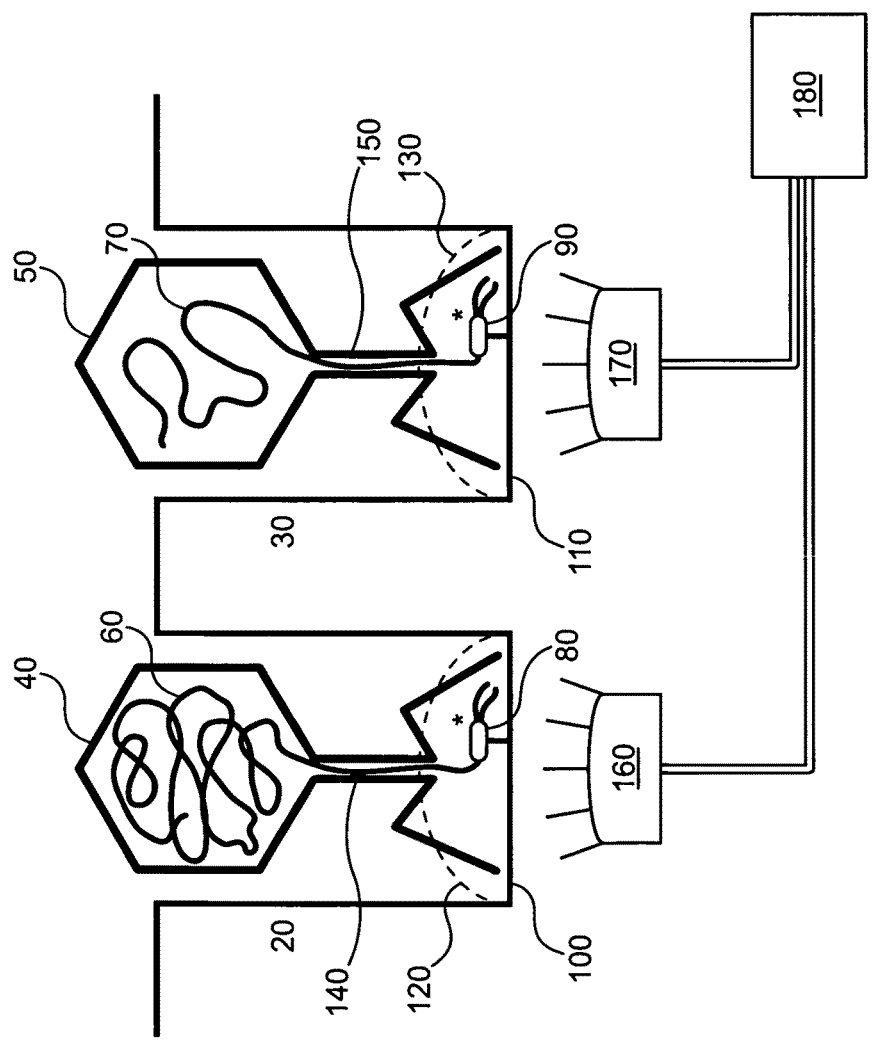
FIG. 1 is a schematic showing packaged capsids in the process of being read by a polymerase in a ZMW.

The invention provides methods and compositions that provide for non-random distribution of target molecules (e.g., analytes such as template nucleic acids and/or relevant enzymes such as polymerases) into small reaction/observation volume arrays, such as ZMW arrays. These methods and compositions can achieve much higher analyte, reagent, and/or reactant loading efficiencies than are typically observed using Poisson-limited random molecule loading methods. General approaches for non-random analyte loading include:

(1) delivering the analyte molecules using a sizing, e.g., particle, delivery system to provide single molecule loading for each molecule type of interest;

(2) creating a single binding site for the analyte in the reaction/observation volume, e.g., by placing or fabricating a nanostructure in the reaction/observation volume, or by selectively forming analyte binding sites in the reaction/observation volume;

(3) reducing the number or availability of binding sites in a reaction or observation region, e.g., by catalyst assisted degradation of the binding sites, or by binding cognate moieties to the binding site, or by molecular blocking of the binding sites;

(4) controllably loading the analyte into the reaction or observation region, e.g., using microfluidic delivery, photoactivation control, optical trapping, electrical trapping, or a combination thereof;

(5) iteratively loading analytes, e.g., by blocking array sites once they are occupied by an analyte, and repeating loading of the analyte to unblocked sites; and, e.g., (6) controlling the size and distribution of observation volumes of the array to limit the quantity, size and location of analyte or other molecules that will fit into the relevant observation volume.

These basic approaches can also be used in combination, e.g., the size and distribution of observation volumes can be selected in conjunction with a particle delivery system to control delivery and retention of particle-bound moieties of interest; binding sites can be used to bind to sizing moieties, iterative loading can be practiced in combination with any of the other approaches, etc.

In the discussions herein, an "analyte" molecule is a molecule analyzed in the system of interest, e.g., a template nucleic acid, primer, enzyme, or the like. For example, in a sequencing reaction, the nucleic acid template is an analyte molecule, as the properties of the template (e.g., its sequence) are under investigation. However, the template is not the only analyte in a sequencing reaction. For example, properties of the sequencing primers are also detected in the system (e.g., primer binding/polymerase initiation activity, as evidenced by a productive sequencing reaction) as are properties of the enzyme (e.g., polymerase activity, also as evidenced by a productive sequencing reaction). For convenience, unless context dictates otherwise, the relevant analyte under consideration can be any moiety active to the analysis, e.g., a substrate, template, primer, enzyme or the like.

Particle/sizing moiety regulated delivery of analytes such as nucleic acids and/or enzymes such as polymerases to small volume arrays such as arrays of ZMWs is accomplished by associating the nucleic acids or enzymes with the particles or other sized (and/or charged) moieties, e.g., by packaging the nucleic acids or enzymes using the particles (e.g., where the particles at issue comprise viral capsids), or by binding or otherwise linking the nucleic acids or enzymes to the particles. Any of a variety of particle types can be used, including viral particles, proteins, protein complexes, beads, metallic particles, large molecules (e.g., PEG) and the like. Each of these approaches is discussed in more detail below.

Array well size and/or distribution can also be controlled to ultimately determine which wells are suitable for receiving which analyte molecules. In one preferred aspect, array wells are sized in a selected pattern to receive variously sized analyte molecules (similarly, array wells can be charged to accept only appropriately charged moieties). For example, wells can be made small enough to receive only a single analyte molecule (or analyte molecule-particle complex), or wells can be sized to preferentially accommodate a single large or small analyte (e.g., a single large or small nucleic acid or enzyme). By controlling the size and placement of such wells, it is possible to control where on the array certain molecules will preferentially be found. Furthermore, by controlling how such arrays are loaded, e.g., by controlling when and where large or small analytes are loaded onto the array, loading densities much higher than Poisson-limited random loading approaches can be achieved.

Non-Random Loading

One preferred aspect of the invention includes the non-random (and non-Poisson limited) delivery of nucleic acids, enzymes and other analytes into the wells or other reaction regions of an array. In general, the analytes (and/or array components) of the invention can be configured so that a single analyte (or other desired number of analytes) is delivered per region. This can be achieved in any of several ways as described herein, including by coupling moieties to the analytes to sterically and/or electrostatically prevent loading of more than one analyte, or, e.g., by incorporating a single binding site for the analyte into the array region, or, e.g., by iterative loading of analytes, or, e.g., by actively controlling loading of the analyte, or, e.g., by temporarily or permanently configuring features of the array to control analyte loading. These and other procedures are discussed in detail herein. The methods herein permit substantially more complete loading of single molecule analytes into arrays than is typical for random loading approaches, in which single molecule distributions of analyte are produced by underloading the array as a whole. As has been noted, random distribution of analytes into the array results in one or fewer analytes being loaded into most reaction/observation volumes only when fewer than about 36% of all observation volumes are loaded. This type of Poisson-limited analyte loading results in few enough molecules being added to the array so that a Poisson-style random statistical distribution of the analyte molecules into the array results in one or fewer analytes per observation volume (in most cases). Prior art yields for single-molecule occupancies of approximately 30% have been obtained for a range of ZMW diameters (e.g., 70-100 nm). See, Foquet (2008), herein. About 60% of the ZMWs in a ZMW array are not loaded (i.e., have no analyte molecules) using such random loading methods.

The various methods of the invention can provide a frequency of as high as 100% loading for the relevant analyte of interest. Such high loading efficiencies are possible, e.g., because the array does not typically accept and/or bind more than one analyte in an analysis region of the array (e.g., by distributing or fabricating one analyte binding particle per well, or one particle per analysis region of a well), or because delivery of the analyte to the well or other array region is controlled. By extending the appropriate incubation times and/or increasing the concentration of particles, more complete loading is achieved. One of skill can, of course, choose to load fewer than 100% of the wells of the array. Typical particle-based arrays of the invention can include greater than 30%, usually greater than 37% (the approximate Poisson random loading limit to achieve maximal single analyte molecule occupancy), typically 38% or more, often as much as 50% or more, and preferably as much as 60%, 70%, 80% or 90% or more of the wells of the array being loaded with a single molecule in an analysis region of each well (or, alternately, simply wells having a single analyte molecule per well). A wide variety of methods, systems and compositions for achieving non-random loading of particles are described herein.

The array feature to be loaded with analyte is dependent on the application at issue and the equipment available. Arrays can include features such as wells, depressions, grooves, waveguides, zero mode waveguides, chambers, microfluidic channels, trenches, magnetized regions, unmagnetized regions, etched structures, machined structures, masked or unmasked analysis regions, masks that permit access by the analyte to any analysis regions, arrangements of particles or other analyte binding sites in the array, arrangements of binding sites, located, e.g., at least 50 nm apart in the array, configured to bind individual analyte molecules, and many other features can be loaded with analyte according to the methods herein. The features can be arranged to provide a physical phase determining feature, e.g., a regular or decipherable pattern of locations into which the analyte is to be loaded. For example, the analyte molecules can be loaded into ZMWs or other features that are located in the array with a regular or selected spacing that places the features, e.g., at least 20 nm apart, at least 30 nm apart, at least 40 nm apart, at least 50 nm apart, at least 60 nm apart, at least 70 nm apart, at least 80 nm apart, at least 90 nm apart; at least 100 nm apart; at least 150 nm apart, at least 200 nm apart, at least 250 nm apart, at least 300 nm apart, at least 350 nm apart, at least 400 nm apart, at least 450 nm apart, or 500 nm or further apart. It should be appreciated that spacing of array features in the array can, of course be further apart, if desired, though this may decrease the density of the features of the array, which may reduce overall throughput of systems that comprise the array features. The phase determining feature can be simple location of the array features, e.g., spacing of the array features on center in a regularly arranged physical array of features, or can be a more complex logically decipherable arrangement, e.g., where the features of the array are arranged in a manner that uses optical masking of signals from the array, and/or data deconvolution algorithms to assign which features contribute to a "logical phase" of the array.

Particle and Other Sizing Moiety Regulated Delivery of Analytes to Arrays

Particles or other sizing moieties can be selected such that a single particle/moiety fits into a single well/observation volume (e.g., ZMW) of a small well array. Sizing methods for sizing array wells to receive the particles or moieties are discussed in more detail below; it is generally possible to control the size of wells to within a few nanometers with respect to diameter and depth; ZMW arrays on the order of 10-200+nm can be achieved using available methods (see, e.g., Foquet et al (2008) "Improved fabrication of zero-mode waveguides for single-molecule detection" *Journal of Applied Physics* 103: 034301; Eid et al. (2008) "Real-Time DNA Sequencing from Single Polymerase Molecules" *Science* DOI 10.1126/science. 322.5905.1263b). Particle/moiety size is a function of the type of particle or other moiety that is used for packaging or binding to the analyte of interest.

Analytes

A variety of analytes can be delivered to reaction/observation regions using the methods and compositions herein. These include enzyme substrates, nucleic acid templates, primers, etc., as well as polypeptides such as enzymes (e.g., polymerases).

A wide variety of nucleic acids can be analytes in the methods herein. These include cloned nucleic acids (DNA or RNA), expressed nucleic acids, genomic nucleic acids, amplified nucleic acids cDNAs, and the like. Details regarding nucleic acids, including isolation, cloning and amplification can be found, e.g., in Berger and Kimmel, *Guide to Molecular Cloning Techniques, Methods in Enzymology volume* 152 Academic Press, Inc., San Diego, Calif. (Berger); Sambrook et al., *Molecular Cloning—A Laboratory Manual* (3rd Ed.), Vol. 1-3, Cold Spring Harbor Laboratory, Cold Spring Harbor, N.Y., 2000 ("Sambrook"); *Current Protocols in Molecular Biology*, F. M. Ausubel et al., eds., Current Protocols, a joint venture between Greene Publishing Associates, Inc. and John Wiley & Sons, Inc; Kaufman et al. (2003) Handbook of Molecular and Cellular Methods in Biology and Medicine Second Edition Ceske (ed) CRC Press (Kaufman); and *The Nucleic Acid Protocols Handbook* Ralph Rapley (ed) (2000) Cold Spring Harbor, Humana Press Inc (Rapley).

Similarly, a wide variety of proteins, e.g., enzymes, can also be delivered using the methods herein. A variety of protein isolation and detection methods are known and can be used to isolate enzymes such as polymerases, e.g., from recombinant cultures of cells expressing the recombinant polymerases of the invention. A variety of protein isolation and detection methods are well known in the art, including, e.g., those set forth in R. Scopes, *Protein Purification*, Springer-Verlag, N.Y. (1982); Deutscher, *Methods in Enzymology Vol.* 182: *Guide to Protein Purification*, Academic Press, Inc. N.Y. (1990); Sandana (1997) *Bioseparation of Proteins*, Academic Press, Inc.; Bollag et al. (1996) *Protein Methods, 2$^{nd}$ Edition* Wiley-Liss, NY; Walker (1996) *The Protein Protocols Handbook* Humana Press, NJ, Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice 3$^{rd}$ Edition* Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, N.J.; and the references cited therein. Additional details regarding protein purification and detection methods can be found in Satinder Ahuja ed., *Handbook of Bioseparations*, Academic Press (2000). Sambrook, Ausubel, Kaufman, and Rapley supply additional useful details.

For a description of polymerases and other enzymes that are active when bound to surfaces, which is useful in single molecule sequencing reactions in which the enzyme is fixed to a surface (e.g., to a particle or to a wall of a reaction/observation region, e.g., in a ZMW), e.g., conducted in a ZMW, see Hanzel et al. ACTIVE SURFACE COUPLED POLYMERASES, WO 2007/075987 and Hanzel et al. PROTEIN ENGINEERING STRATEGIES TO OPTIMIZE ACTIVITY OF SURFACE ATTACHED PROTEINS, WO 2007/075873). For a description of polymerases that can incorporate appropriate labeled nucleotides, useful in the context of sequencing, see, e.g., Hanzel et al. POLYMERASES FOR NUCLEOTIDE ANALOGUE INCORPORATION, WO 2007/076057. For further descriptions of single molecule sequencing applications utilizing ZMWs, see Levene et al. (2003) "Zero Mode Waveguides for single Molecule Analysis at High Concentrations," *Science* 299:682-686; Eid et al. (2008) "Real-Time DNA Sequencing from Single Polymerase Molecules" *Science* DOI: 10.1126/science. 322.5905.1263b; Korlach et al. (2008) "Selective aluminum passivation for targeted immobilization of single DNA polymerase molecules in zero-mode waveguide nanostructures" *Proceedings of the National Academy of Sciences U.S.A.* 105(4): 1176-1181; Foquet et al. (2008) "Improved fabrication of zero-mode waveguides for single-molecule detection" *Journal of Applied Physics* 103, 034301; "Zero-Mode Waveguides for Single-Molecule Analysis at High Concentrations" U.S. Pat. No. 7,033,764, U.S. Pat. No. 7,052, 847, U.S. Pat. No. 7,056,661, and U.S. Pat. No. 7,056,676, the full disclosures of which are incorporated herein by reference in their entirety for all purposes.

Viral Particles

In one particularly preferred aspect, the particle comprises a viral particle (e.g., a capsid, optionally with a tail, capsid display portion, or other structural feature) that packages a nucleic acid analyte (e.g., a DNA). A very wide variety of systems that package target nucleic acids into viral particles are known, including those based upon various bacteriophage. These include, e.g., viruses of the Siphoviridae (e.g., λ-like viruses such as Enterobacteria phage λ; T1-like viruses such as Enterobacteria phage T1; T5-like viruses; e.g., Enterobacteria phage T5; c2-like viruses such as *Lactococcus* phage c2; L5-like viruses, such has *Mycobacterium* phage L5; ψM1-like viruses such as *Methanobacterium* ψM1; φC31-like viruses such as *Streptomyces* phage φC31; N15-like viruses, such as Enterobacteria phage N15); the Myoviridae (including the T4-like viruses such as Enterobacteria phage T4 and Enterobacteria phage T2; P1-like viruses such as Enterobacteria phage P1; P2-like viruses such as Enterobacteria phage P2; Mu-like viruses such as Enterobacteria phage Mu; SPO1-like viruses such as *Bacillus* phage SPO1; φH-like viruses such as *Halobacterium* virus pH;); viruses of the Podoviridae family (e.g., T7-like viruses such as Enterobacteria phage T7; φ29-like viruses such as *Bacillus* phage φ29; P22-like viruses such as Enterobacteria phage P22; N4-like viruses such as Enterobacteria phage N4) and the like. For an introduction to bacteriophage and a description of bacteriophage packaging systems, see, e.g., Abedon (2008) *Bacteriophage Ecology: Population Growth, Evolution, and Impact of Bacterial Viruses* (Advances in Molecular and Cellular Microbiology) Cambridge University Press ISBN-10: 0521858453; *Bacteriophages: Methods and Protocols* (Methods in Molecular Biology) (2008) Clokie and Kropinski (Editors) Humana Press; *Bacteriophage: Genetics and Molecular Biology* (2007) Mcgrath and Van Sinderen (Editors) Caister Academic Pr; ISBN-10: 190445514X; Abedon (2005) *The Bacteriophages* second edition Calendar (Editor) Oxford University Press, USA ISBN-10: 0195148509; Birge (2005) *Bacterial and Bacteriophage Genetics* 5th edition ISBN-10: 0387239197; and Sidhu (2005) *Phage Display In Biotechnology and Drug Discovery* CRC ASIN: B00144GGZE. Additional details regarding viral capsid packaging can be found in Olivera et al. (2005) *J. Mol. Biol.* 353:529 and the references therein and in U.S. Pat. No. 5,741,683.

Other viral packaging systems that operate in eukaryotic cells can also be used, including viral particles formed by the Parvoviridae such as the Parvovirinae (e.g., Dependovirus such as adeno-associated virus, or AAV); nonenveloped icosahedral viruses such as the Adenoviridae (e.g., the Aviadenovirus, the Atadenovirus, the Mastadenovirus, and the Siadenovirus) or the Picornaviridae (e.g., hoof and mouth virus of the Aphthovirus). Even enveloped viruses can be useful, e.g., where the enveloped capsid structure constitutes the relevant particle, or where the capsid components are used in a system that fails to produce a viral envelope (resulting in capsid-packaged nucleic acids). Examples of such systems include the Retroviridae (e.g., the Orthoretrovirinae such as the Lentivirinae, including Bovine immunodeficiency virus (BIV), Equine lentiviruses, Equine infectious anemia virus (EIAV) Feline lentiviruses such as Feline immunodeficiency virus (FIV), Caprine arthritis encephalitis virus (CAEV), Visna/maedi virus, the Primate lentiviruses such as Human immunodeficiency viruses 1 and 2, and Simian immunodeficiency virus). Details regarding viral life cycles and viral structural components can be found, e.g., in Carter and Saunders (2007) *Virology: Principles and Applications* Wiley; 1st edition ISBN-10: 0470023872; Dimmock et al. (2007) *Introduction to Modern Virology* 6th edition Wiley-Blackwell, ISBN-10: 1405136456; Flint et al. (2007) *Principles of Virology* ISBN 10: 1555812597; Wagner et al. (2007) *Basic Virology* 3rd edition Wiley-Blackwell ISBN-10: 1405147156; and Acheson (2006) *Fundamentals of Molecular Virology* John Wiley & Sons, Inc.; ISBN-10: 0471351512.

While the details of such systems differ, there are broad similarities within the context of the invention. In general, it is useful to package an analyte nucleic acid using a host cell that produces viral particle (e.g., capsid, tail, etc.) proteins. To accomplish analyte (e.g., DNA or RNA) packaging, it is often useful to incorporate a cis-active packaging site into the analyte. Nucleic acids that include such cis-active packaging sites are packaged by the host cell (or in an in vitro a host cell extract that comprises the relevant capsid or other structural proteins). The addition of a packaging site onto a nucleic acid analyte can be accomplished through standard cloning methods such as those taught in Berger and Kimmel, *Guide to Molecular Cloning Techniques, Methods in Enzymology volume* 152 Academic Press, Inc., San Diego, Calif. (Berger); Sambrook et al., *Molecular Cloning—A Laboratory Manual* (3rd Ed.), Vol. 1-3, Cold Spring Harbor Laboratory, Cold Spring Harbor, N.Y., 2000 ("Sambrook"); *Current Protocols in Molecular Biology*, F. M. Ausubel et al., eds., Current Protocols, a joint venture between Greene Publishing Associates, Inc. and John Wiley & Sons, Inc (supplemented through the current date); Kaufman et al. (2003) Handbook of Molecular and Cellular Methods in Biology and Medicine Second Edition Ceske (ed) CRC Press (Kaufman); and *The Nucleic Acid Protocols Handbook* Ralph Rapley (ed) (2000) Cold Spring Harbor, Humana Press Inc (Rapley).

Packaging sites can also be linked to a nucleic acid analyte by any of a variety of in vitro nucleic acid coupling methods, including ligation with a ligase (including in a ligase chain reaction), or template amplification using primers that comprise the packaging sites, e.g., using a polymerase (e.g., as occurs in PCR). Details regarding ligation and polymerization can be found in Sambrook and Ausubel, as well as in Kaufman, Berger, and Rapley, supra, as well as in *PCR Protocols A Guide to Methods and Applications* (Innis et al. eds) Academic Press Inc. San Diego, Calif. (1990) (Innis); Chen et al. (ed) *PCR Cloning Protocols, Second Edition* (Methods in Molecular Biology, volume 192) Humana Press; and in Viljoen et al. (2005) *Molecular Diagnostic PCR Handbook* Springer, ISBN 1402034032. Further details regarding Rolling Circle Amplification can be found in Demidov (2002) "Rolling-circle amplification in DNA diagnostics: the power of simplicity," *Expert Rev. Mol. Diagn.* 2(6): 89-94; Demidov| and Broude (eds) (2005) *DNA Amplification: Current Technologies and Applications.* Horizon Bioscience, Wymondham, UK; and Bakht et al. (2005) "Ligation-mediated rolling-circle amplification-based approaches to single nucleotide polymorphism detection" *Expert Review of Molecular Diagnostics*, 5(1) 111-116. In general, such linkage methods have an advantage in that they do not require subcloning to link the packaging site of interest to the nucleic acid of interest. The packaging sites for hundreds of viruses are known.

Packaging sites can also be linked to non-standard nucleic acid molecules or even to non-nucleic acid molecules; so long as the non-standard molecules includes a packaging site and does not prevent capsid formation it can be packaged within a viral capsid. Linkage chemistries for linking nucleic acids to non-standard nucleic acids and other molecules are generally available.

The host cell or host cell extract that provides the viral capsid proteins to the analyte nucleic acid can encode viral packaging components in trans, using any of a variety of generally well-understood methods. For example, the host cell can include plasmid or chromosomally integrated genes that encode the relevant packaging components (e.g., capsid and/or tail proteins; sometimes in conjunction with a polymerase or other protein used in the viral life-cycle). Typically, these plasmids or integrated genes lack a cis-active packaging site, to prevent self-packaging of the viral genes (or transcripts thereof) themselves. Similarly, co-infection approaches can be used, in which helper viruses are used to co-infect the host (packaging) cell; these helper viruses produce viral components (optionally in conjunction with the plasmid/chromosomally integrated viral capsid genes). Such helper viruses can, themselves, be packaging deficient, or can form a different virus when packaged than the packaged analyte nucleic acid (e.g., as occurs in the case of AAV and adenovirus). In this case, the helper virus can be separated from the packaged analytes using standard separation methods, such as centrifugation or chromatography. For further details regarding viral packaging methods and compositions, see, e.g., Abedon (2008) *Bacteriophage Ecology: Population Growth, Evolution, and Impact of Bacterial Viruses* (Advances in Molecular and Cellular Microbiology) Cambridge University Press ISBN-10: 0521858453; *Bacteriophages: Methods and Protocols* (Methods in Molecular Biology) (2008) Clokie and Kropinski (Editors) Humana Press; *Bacteriophage: Genetics and Molecular Biology* (2007) Mcgrath and Van Sinderen (Editors) Caister Academic Pr; ISBN-10: 190445514X; Abedon (2005) *The Bacteriophages* second edition Calendar (Editor) Oxford University Press, USA ISBN-10: 0195148509; Carter and Saunders (2007) *Virology: Principles and Applications* Wiley; 1st edition ISBN-10: 0470023872; Dimmock et al. (2007) *Introduction to Modern Virology* 6th edition Wiley-Blackwell, ISBN-10: 1405136456; Flint et al. (2007) *Principles of Virology* ISBN 10: 1555812597; Wagner et al. (2007) *Basic Virology* 3rd edition Wiley-Blackwell ISBN-10: 1405147156; Acheson (2006) *Fundamentals of Molecular Virology* John Wiley & Sons, Inc.; ISBN-10: 047135151 Birge (2005) *Bacterial and Bacteriophage Genetics* 5th edition ISBN-10: 0387239197; and Sidhu (2005) *Phage Display In Biotechnology and Drug Discovery* CRC ASIN: B00144GGZE.

In one useful configuration, the gene sequence for a polymerase can be spliced into the gene for a phage coat protein. When this gene is expressed, the result is a viral particle containing a single polymerase fused to the virus' coat protein. In this case, the DNA to be sequenced is bound to the polymerase that is fused to the coat protein. The entire viral particle with the fused polymerase/DNA can be loaded into the ZMW or other relevant array structure. As in other embodiments, the size of the viral particle sterically hinders more than one from entering the array structure (e.g., ZMW). Once the exposed polymerase attaches to the bottom of the array in the ZMW or other structure, the capsid and coat protein can be removed using appropriate chemistry. Further details regarding phage display of proteins (which can be adapted to display of polymerases) and coat proteins can be found, e.g., in Smith and Petrenko "Phage display" *Chem. Rev.* (1997) 97, 391-410 and in and Sidhu (2005) *Phage Display In Biotechnology and Drug Discovery* CRC ASIN: B00144GGZE.

One useful feature of virally packaged nucleic acids is that they are precisely sized by the viral particle (e.g., capsid) that they are packaged into. That is, viral capsids have relatively precise dimensions that do not display a large radius of gyration, in contrast to the case for an unpackaged nucleic acid. This is particularly useful for delivering large nucleic acids to wells, because the large radius of gyration of a large nucleic acid in solution may make it difficult to deliver the nucleic acid into a target well. In contrast, a capsid can actually be substantially smaller than the radius of gyration of the nucleic acid that is packaged by the capsid. That is, a nucleic acids packaged inside of a capsid can have a substantially more compact form than the same nucleic acid free in solution (e.g., a DNA can be smaller inside of a capsid than the same DNA is when free in solution). Even when the capsid assembly is larger than the nucleic acid, it still has the advantage of having a precisely defined size and shape. In general, the precise size and shape of a viral particle permits one of skill to size and fit wells of an array (e.g., ZMWs in a ZMW array) to conform to the packaging capsid assembly, eliminating the possibility of multiple capsids entering the well.

These features permit a target array to be incubated with higher concentrations of the viral particles than of free nucleic acids, and for longer periods of time, permitting more complete (dense) loading of the array. Loading densities higher than 37% (the typical approximate Poisson random loading limit) can be achieved, e.g., about 40%, 50%, 60%, 70%, 80%, 90%, 95%, 99% or more of the wells of the array can be loaded with a single DNA molecule, e.g., packaged within the capsid.

Non-Viral Particles and Other Sizing Moieties

Sizing moieties such as particles can include either biological or non-biological particle materials (or both). Thus, viral components are included within the definition of particles for purposes of the present invention as discussed above. In general, particles or other sizing moieties to be delivered to the arrays of the invention can be formed of any discrete material that can be coupled/associated, at least temporarily, to or with an analyte (e.g., a DNA, or an enzyme such as a polymerase) of interest, for delivery to the array of interest. In addition to viral particles, examples of useful particles include a variety of polymer and ceramic beads, self-assembling structures such as nucleic acid origami (discussed in more detail herein), as well as metal, glass, teflon, or silica particles. PEG or other large polymers can also be used to provide an appropriate particle/sizing moiety. For example, polymers, proteins, nucleic acids, polymer beads, silica beads, ceramic beads, glass beads, magnetic beads, metallic beads, and organic resin beads can be used to provide particles in the context of the invention. The particles can have essentially any shape, e.g., spherical, helical, spheroid, rod shaped, cone shaped, disk shaped, cubic, polyhedral or a combination thereof. Optionally, they are configured to fit individually into the relevant well (e.g., ZMW) of the relevant array; the shape of the relevant particle can also be used to orient the particle in the relevant well, e.g., by shaping the walls of the well to conform to the particle. Particles can optionally be coupled to any of a variety of reagents that facilitate surface attachment of the analyte, e.g., affinity matrix materials, or the like, e.g., nucleic acid synthesis/coupling reagents, peptide synthesis/coupling reagents, polymer synthesis reagents, nucleic acids, nucleotides, nucleobases, nucleosides, peptides, amino acids, various monomers, biological sample materials, synthetic molecules, or combinations thereof. In addition to delivering the analyte of interest, particles optionally serve a variety of other purposes within the arrays of interest, including acting as "blank" or other control particles, calibration particles, sample delivery particles, reagent particles, test particles, etc.

Particles and other sizing moieties are sized to fit, optionally individually, into the array reaction/observation site (e.g., reaction/observation portion of a ZMW or other well). Accordingly, particles will range in size, depending on the application, e.g., from about 1-500 nm in least one cross-sectional dimension. Typical sizes in ZMW applications will range from about 5-100 nm in at least one dimension, e.g., about 25 to about 75 nm. In one useful embodiment, useful particles are about 50 nm in at least one dimension.

Mono-disperse particle populations can be bound to an analyte of interest, e.g., an enzyme such as a polymerase, a substrate such as a nucleic acid, or even an enzyme-substrate (e.g., a polymerase-template complex). By sizing the particles to match the relevant array feature (e.g., well, ZMW, reaction or observation region, or the like), the analyte will be delivered to the relevant array feature in the desired number (e.g., 1 analyte per region). Analytes or particles can include cleavage features, which permit cleavage of the analyte from the particle, such as restriction sites to permit specific cleavage of a nucleic acid, or a protease site to permit specific cleavage of a protein or protein-nucleic acid complex. The analytes can further include binding elements that permit the analyte to bind to the relevant array feature, e.g., an avidin or biotin site that can bind a corresponding feature on the array. Examples of appropriate binding partners for linking analytes and particles, or analytes and array surfaces include antibodies and ligands, avidin and biotin, nickel-NTA and polyhistidine, complementary nucleic acids, and many others.

The particles of the arrays of the invention can be essentially any discreet material which can be moved into the array wells (e.g., ZMWs). Example particles include viral particles as discussed above, as well as self-assembling structures, large nucleic acid or polypeptide complexes (including e.g., ribosomes), polymeric, ceramic or metallic particles, beads, and the like. For example, polymer beads (e.g., polystyrene, polypropylene, latex, nylon and many others), silica or silicon beads, ceramic beads, glass beads, magnetic beads, metallic beads and organic compound beads can be used. An enormous variety of particles are commercially available, e.g., those typically used for chromatography (see, e.g., Catalogs from Sigma-Aldrich (Saint Louis, Mo.), Supelco Analytical (Bellefonte, Pa.; sold, e.g., through Sigma-Aldrich), as well as those commonly used for affinity purification (e.g., the various magnetic Dynabeads™, which commonly include coupled reagents) supplied e.g., by Invitrogen. For a discussion of matrix materials see also, e.g., Hagel et al. (2007) *Handbook of Process Chromatography, Second Edition: Development, Manufacturing, Validation and Economics*, Academic Press; 2nd edition ISBN-10: 0123740231; Miller (2004) *Chromatography: Concepts and Contrasts* Wiley-Interscience; 2nd edition ISBN-10: 0471472077; Satinder Ahuja (2002) *Chromatography and Separation Science (SST) (Separation Science and Technology* Academic Press, ISBN-10: 0120449811; Weiss (1995) *Ion Chromatography* VCH Publishers Inc.; Baker (1995) *Capillary Electrophoresis* John Wiley and Sons; Marcel Dekker and Scott (1995) *Techniques and Practices of Chromatography* Marcel Dekker, Inc.

Steric Exclusion Using a Large Polymer Construct Attached to a Polymerase

Analytes such as enzymes, e.g., polymerases, can be modified site-specifically to introduce one or more reactive groups onto the enzyme protein. These groups can be introduced through kits such as SNAP™ tagging chemistry or through site-specific peptide residues, to yield a specific reactive group for covalent coupling. Through these coupling chemistries, high molecular weight polymer chains, such as poly (ethylene glycol) PEG chains or other particles/moieties can be introduced onto enzymes to size the enzyme to a ZMW (or other array reaction region) to preventing loading of multiple enzyme molecules into a single reaction site. The coupled polymers can be linear (and can be located at multiple or single locations on the enzyme), cross-linked, branched, hyperbranched, starred, or dendritic (including dendrimers or dendrons) or the like. Further, these attached chemistries can also include less inert chemistries such as poly(lactic acid) or poly(glycolic acid) to provide an ability to deliver the protein first with the polymeric addition, but to introduce the ability to use light or pH to remove parts of the polymer, if desired. High molecular weight biopolymers such as hyaluronic acid and collagen type I, are also useful to regulate the size of the enzyme, or other analyte, such that only a selected number of enzyme molecules (e.g., 1 molecule) can be delivered into each ZMW or other array feature of interest.

Using Ribosomes as Particles: Ribosome Display and Other Bulky Polymerase Attachments to Super-Poisson-Load ZMWs As noted, in typical random loading methods, if there is more than one analyte binding site per ZMW, the concentration of the analyte applied to the array can be adjusted to statistically limit most wells to 1 or 0 polymerases (a process described by Poisson statistics), but this ultimately leaves most wells empty and the array under-utilized. Ideally, a ZMW or other single analyte molecule reaction array, e.g., for single-molecule sequencing, will contain a single active analyte (e.g., polymerase) in every array site (e.g., every ZMW of a ZMW array). As described above, one solution to achieve such "super-Poisson" loading of an analyte is to attach a particle or polymer to the polymerase so that only one analyte can fit in each ZMW.

In one preferred embodiment, the particle is a ribosome, which is sized to block loading of more than one polymerase per ZMW or other relevant array structure or region. The dimensions of a typical ribosome are about 25 nm (250 A), which is close to the diameter of a typical ZMW (e.g., about 10-100 nm), making the ribosome well suited to this purpose. As in other particle embodiments herein, the size of the ZMW or other array structure can also be optimized with respect to size or shape to better fit the structure to the ribosome. This approach also allows the use of ribosome display strategies for protein selection and enrichment (e.g., an alternative to phage/yeast display), providing a screening platform for selecting polymerases or other displayed enzymes for screenable activities of interest (e.g., improved processivity, improved ability to incorporate labeled nucleotides, improved residence time, or the like).

In one example, a fusion polymerase or other fusion enzyme of interest is translated in vitro to comprise an N-terminal binding tag (e.g., a biotin, an antibody hapten, an antibody or portion thereof, etc.). For example, the fusion can be an N-terminal biotin-polymerase fusion. A linker can be included in the fusion at the C-terminus to allow an active portion of the protein (e.g., an active polymerase domain) to fold outside of the ribosome exit tunnel (a 15-20 amino acid linker is sufficient to extend the bulk of the fusion protein out of the exit tunnel). The fusion lacks a stop codon; thus, the ribosome stalls at the end of the mRNA during translation, but there is no translation termination—the ribosome stalls on the mRNA with the protein still attached to the ribosome (but appropriately folded) coming out of the exit tunnel. One can use appropriate in vitro extracts to provide the ribosome, or can use, e.g., the available Protein synthesis Using Recombinant Elements (PURE) translation system (Kudlicki et al. (2007) *Cell-Free Protein Expression* ISBN: 978-1-58706-123-3). This yields a binding moiety-polymerase-linker-25 nM ribosome construct, which can be distributed into ZMWs or other array features. In one specific example, the fusion is based on a phi-29 polymerase protein, that includes an N-terminal biotin, and a C-terminal polypeptide linker.

Typically, only one fusion-ribosome conjugate can easily fit into the ZMW, and be immobilized via the biotin or other binding component moiety—either on the walls or bottom of each reaction region. Once a fusion-ribosome conjugate is located in the ZMW or other reaction region, the entry of additional fusion-ribosome conjugates is significantly inhibited. If desired, the ribosome can be released from the fusion protein using puromycin, a small molecule drug that adds to the C-terminus by performing a type of peptidyl transfer. The end result is a fusion protein (e.g., a polymerase) bound in the reaction region; released ribosomes can be washed away using appropriate washing protocols.

The system can also be used to screen polymerase libraries. For example, ribosome display libraries of fusion protein variants could be delivered to the ZMW or other reaction region with the mRNA attached. The fusion protein, e.g., polymerase (e.g., if it has reverse transcriptase activity, or if a reverse transcriptase is added to the reaction region) can be screened for the ability to sequence its own mRNA/cDNA, and/or for any property that is useful, e.g., to single molecule sequencing (improved processivity, increased residence time, reduced branching fraction, improved ability to incorporate labeled nucleotides, etc.). Examples of such desirable features for polymerases and appropriate screens are found, e.g., in Hanzel et al. POLYMERASES FOR NUCLEOTIDE ANALOGUE INCORPORATION, WO 2007/076057; and Rank et al., POLYMERASE ENZYMES AND REAGENTS FOR ENHANCED NUCLEIC ACID SEQUENCING WO2008/051530.

This system can also work on DNA encoding an RNA if ribosome display is performed with each gene in a separate array feature (e.g., array well or other compartment), e.g., in a separate ZMW. In the latter case, the delivered complex would be a pool of polymerases, each one bound at its active site to its own gene, and to its mRNA and a ribosome via a C-terminal extension.

Other bio-molecule particles can similarly be attached to a polymerase or other protein of interest, e.g. an antibody conjugated to a large moiety such as a bead. This variation has the advantage of permitting different sizes of bulky attachments. The attachment could be released after the polymerase is loaded, or where there is an advantage to having a bulky group occupying a large part of the ZMW, it can stay attached during sequencing.

Large DNAs as Sizing Moieties to Deliver Analytes

As described herein, sizing moieties such as particles and large molecules are used in the present invention to increase the percentage of array sites occupied by a single molecule of analyte. That is, by sterically limiting the number of moiety-bound analytes that can fit into an array site such as a ZMW, it is possible to load essentially all of the sites with a single molecule of analyte, preventing duplicate loading of any individual site. In one embodiment, the analyte can be delivered to a ZMW or other reaction region of an array in conjunction with a large DNA. The large DNA sterically prevents entry of additional DNA-bound analytes to the reaction region, making it possible to load up to all of the reaction regions of the array with a single analyte molecule. A large DNA can be bound, for example, to a polymerase analyte, or to a template nucleic acid analyte of interest, or both. The large DNA can also, itself, be a template nucleic acid to be sequenced.

In one example, the analyte is a polymerase that is pre-bound to the large DNA (outside of the ZMWs or other array regions), which can be single-stranded, double-stranded, circular, in a SMRT™-bell configuration, or in any other sufficiently large configuration to provide steric inhibition to entry of additional molecules into a reaction region, such as a ZMW (further details regarding the related use of self-assembling nucleic acid structures for this purpose is also found below). For example, the DNA can be long enough such that, with the radius of gyration of the template, only one polymerase-DNA complex can fit into a ZMW at a time. After all the ZMWs or other array regions are loaded with the polymerase-large DNA complex, the long DNA template can be released, e.g., under low-salt conditions. The desired sequencing template can then be delivered to the polymerase. Alternatively, the long template used for steric hindrance can be the same template that will be sequenced, in which case it is not released.

Alternatively, the polymerases can be synthesizing the long strand of DNA template while they are being loaded into the ZMWs. In this case, the concentration and activity of the polymerase is coordinated with the rate of synthesis such that by the time a second polymerase complex could reach a ZMW, the DNA template is already large enough to sterically hinder loading of this second polymerase complex. In yet another embodiment, one can randomly load the ZMWs with polymerase according to Poisson statistics, and then subsequently start the synthesis reaction. After some time, all the ZMWs that are loaded with a polymerase will have a large DNA template attached that sterically hinders additional polymerases from entering. This procedure can be repeated several times until many or essentially all of the ZMWs are loaded with only one polymerase (e.g., greater than 40%, 50%, 60%, 70%, 80%, 90%, etc.). Further details regarding various iterative loading formats that can be adapted to this embodiment are also found herein.

Steric Exclusion Using Self-Assembled DNA Origami Polymerase Complexes

If the proper nucleic acid components are mixed together, they self-assemble into structures (commonly referred to as "DNA origami") with a selected size and geometry. These self-assembling structures can also be used as sizing moieties for delivery of single analyte molecules (e.g., template nucleic acids and/or polymerases) to size-confined array features/reaction regions (e.g., ZMWs) of an array, relying on the size and shape of the self-assembling molecule to provide steric exclusion to entry of additional particles into a given reaction region.

Self assembling nucleic acid structures (or other self-assembling polymers) can be designed with specific three-dimensional shapes such that only one structure at a time fits into a ZMW or other reaction region. In addition, a self-assembling nucleic acid structure can be designed such that there is only one site on the structure that a polymerase or other analyte can bind to. For example, self-assembling nucleic acids can be designed with only one single-stranded nucleic acid site that is complementary to an oligonucleotide that is linked to the polymerase, e.g., via a biotin linkage. Where the analyte to be delivered is a template nucleic acid to be sequenced, the self-assembling structure can include a region that is complementary to the template nucleic acid. In one variant, the self-assembling nucleic acid can be designed with only one binding site for a small metal nanoparticle that is capable of binding to a single polymerase or other analyte, leading to delivery of one polymerase per reaction site. Various approaches to creating small metal particles that bind to a single analyte are described herein.

Alternatively, one could use the method of "scaffolded DNA origami" (Rothemund (2006) "Folding DNA to create nanoscale shapes and patterns" *Nature* 440:16) to create arbitrary two-dimensional DNA origami shapes. Two such shapes, such as a flat circle and a rectangle that has been stapled together at each side to form a hollow cylinder, can be combined together to form a "cup and coaster" shape. This "cup and coaster" DNA origami is designed to be approximately the same size as a ZMW or other array region of interest. The cup and coaster is also designed to have just one binding site for a polymerase or other analyte, leading to delivery of a single analyte to an array site of interest (e.g., to a ZMW).

A variety of available DNA structures can be adapted to the present invention for delivery of a single analyte, such as a template nucleic acid or polymerase molecule, to an array site of interest. Such self-assembling DNA structures include, e.g., DNA grids (Park et al. (2006) "Finite-Size, Fully Addressable DNA Tile Lattices Formed by Hierarchical Assembly Procedures" *Angew. Chem. Int. Ed.* 45:735-739), DNA Dodecahedrons (Zhang et al. (2008) "Conformational flexibility facilitates self-assembly of complex DNA nanostructures *PNAS* 105(31):10665-10669; Zimmermann et al. (2007) "Self-Assembly of a DNA Dodecahedron from 20 Trisoligonucleotides with C3h Linkers" *Angewandte Chemie International Edition*, doi: 10.1002/anie.200702682), icosahedra and nanocages (Zhang et al. (20080 "Conformational flexibility facilitates self-assembly of complex DNA nanostructures" *PNAS* 105(31)10665-10669), Sierpinski triangles (Rothemund et al. (2004) "Algorithmic Self-Assembly of DNA Sierpinski Triangles", PLoS Biol 2(12): e424), DNA Octahedrons (Andersen et al., (2008) "Assembly and structural analysis of a covalently closed nano-scale DNA cage" *Nucleic Acids Research* 36(4): 1113-1119), DNA grids formed with gold particles (Zhang et al. (2006) "Periodic Square-Like Gold Nanoparticle Arrays Templated by Self-Assembled 2D DNA Nanogrids on a Surface" *Nano Lett.* 6(2): 248-251), and ladder-shaped polycatenanes (Weizmann et al. (2008) "A polycatenated DNA scaffold for the one-step assembly of hierarchical nanostructures" *PNAS* 105(14) 5289-5294). After any of these self assembling structures, in combination with an analyte of interest (e.g., a template or polymerase) are self-assembled and loaded onto the regions of the array (e.g., into ZMWs of the array) at high concentrations, no more than a desired number of complexes (e.g., 1 complex for single molecule reactions such as SMS) will fit into each ZMW or other relevant array region. In principle, all or essentially of the array regions (e.g., ZMWs) can be loaded with a single analyte molecule of interest (polymerase, template, etc.), complexed with the self-assembling nucleic acid (of course, fewer than 100% can also be loaded by this method, e.g., greater than about 40%, 50%, 60%, 70%, 80%, 90%, etc.).

Methods for Super Poisson Loading of ZMWs Using Nucleic Acid Masking

In several embodiments of the invention, it is desirable to have exactly one polymerase or other analyte (e.g., template) per ZMW or other reaction region. After standard (unmasked) surface functionalization methods are used to add groups of interest to a ZMW or other reaction region, there are often multiple attachment sites, and the polymerase, template, complex or other assembly of interest is not large enough to sterically exclude further polymerases, etc., from binding. To reduce the number of attachment sites for an analyte, a self assembling DNA, RNA, PDNA, etc., can be applied as a mask to the reaction regions.

That is, DNA or other nucleic acids (or other biomolecules) are used to mask those portions of a reaction region to be functionalized (to which a group is added to facilitate binding of analytes such as polymerases or sequencing templates). In broad overview, this mask is applied, and then the region is functionalized chemically, leaving a binding group such as biotin only in exposed (unmasked) areas of the reaction region. The binding group is bound to the analyte via an appropriate binding interaction such as biotin/avidin. Additional analytes can be bound to the exposed region, e.g., via a second binding method (e.g., where the binding group is a nucleic acid and the analyte is bound via hybridization).

In some applications, it is undesirable to have large assemblies of masking DNA, etc., in the well during the sequencing run. One alternative is to use a large nucleic acid assembly as a mask to provide exactly one attachment site linked to the surface of a given reaction region, and to then release the assembly, leaving a single attachment site for the polymerase or other analyte of interest.

This overall process is illustrated in FIG. 15. Generally, a ZMW comprising an appropriately functionalized surface (e.g., functionalized with benzyl-guanine) is masked with a large DNA that comprises a complementary tag (e.g., in this example, a SNAP™ tag). This tag is bi-functional, comprising a site for analyte binding (in the illustrated case, by incorporating a protein binding tag). The DNA is optionally attached to the bi-functional tag via a cleavable (e.g., photocleavable) linker (denoted PC1). The mask assembly is flowed into the well, sterically blocking entry of additional similar moieties. The DNA is then released by photo-activation, leaving a single bi-functional tag for protein binding. The bi-functional tag can include a cleavable linker, e.g., a second photo-cleavable linker ("PC2") that is cleaved at a different wavelength than the first cleavable linker. Cleavage of this linker removes the analyte, permitting the assembly to be reused.

Figure 15A:
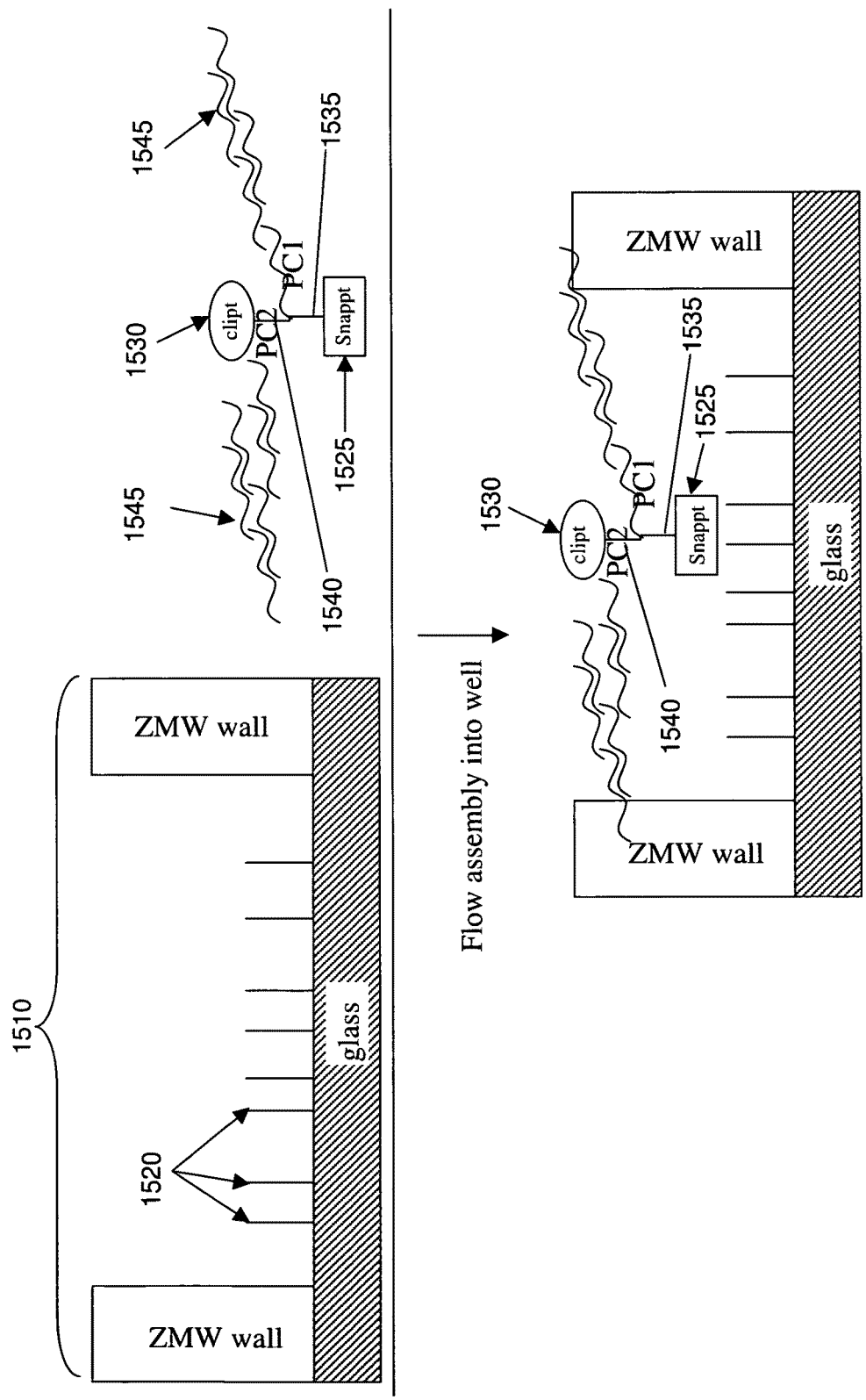
FIG. 15, panels A-C provide a schematic example of a DNA masking process.
Figure 15B:
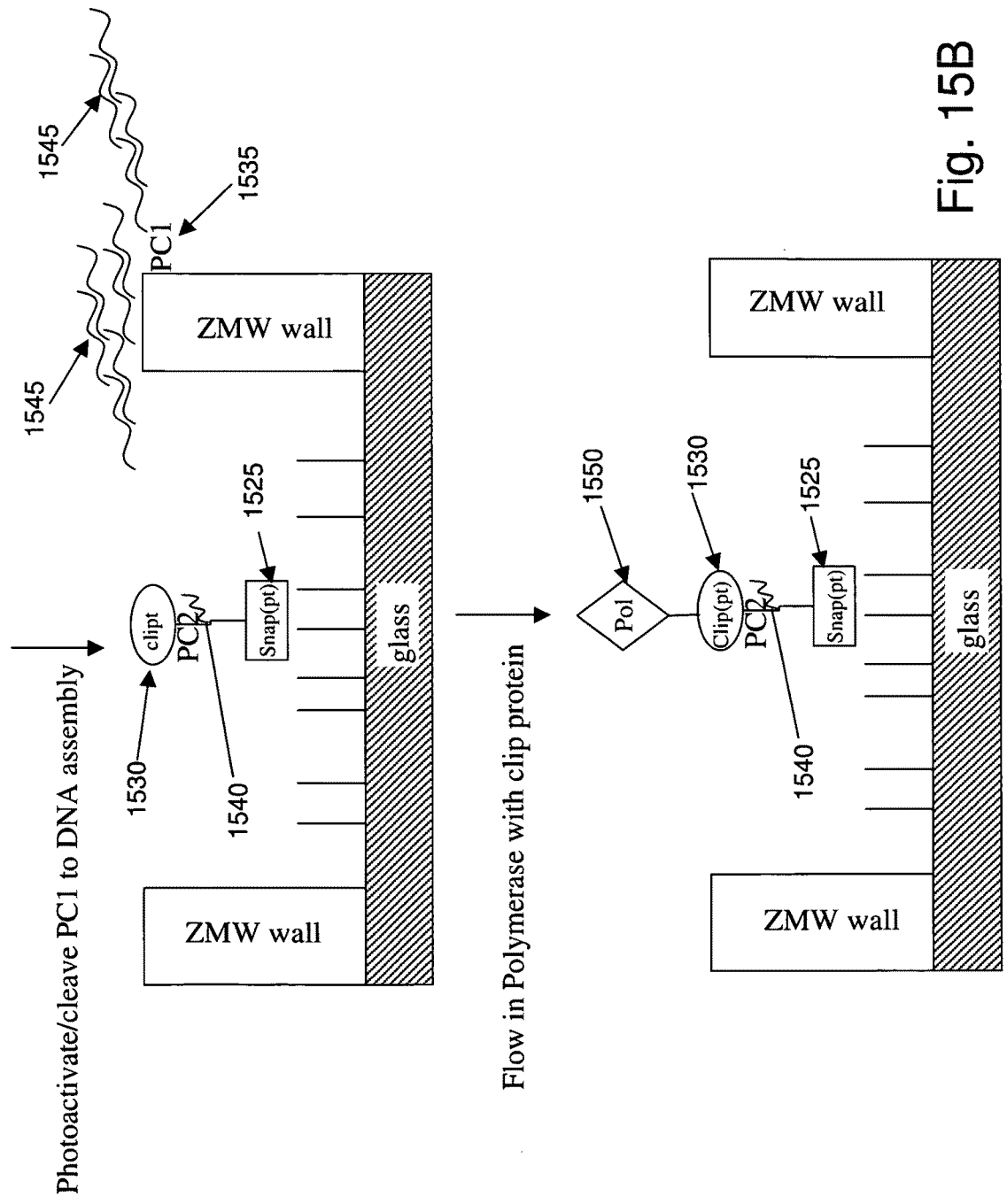
Figure 15C:
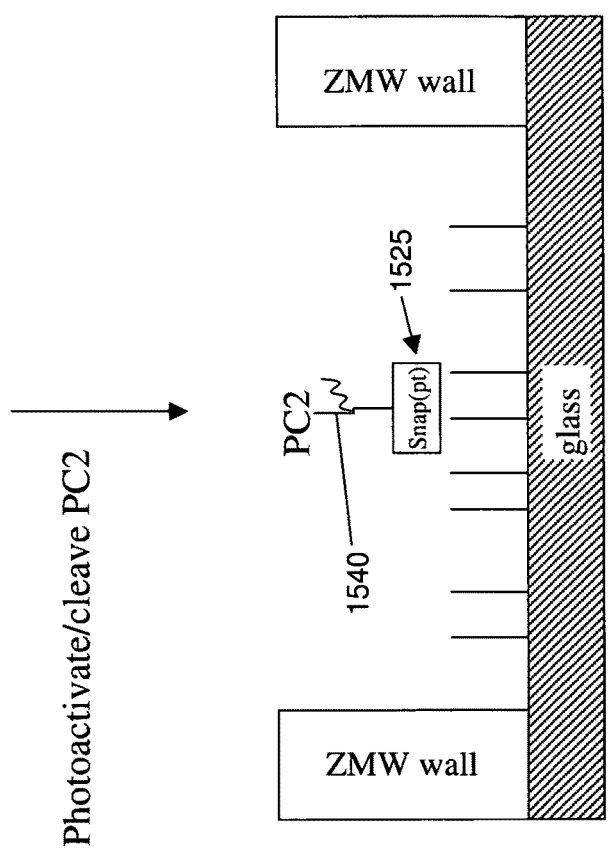

For example, as shown in FIG. 15A, ZMW 1510 has bottom surface 1515 functionalized with benzyl-guanine 1520. SNAP-tag 1525 is linked to Clip-tag 1530 via first photocleavable linker (PC1) 1535 and second photocleavable linker (PC2) 1540. Large DNA mass 1545 is linked to PC1, and the resulting mask assembly is flowed into the ZMW. The assembly is covalently immobilized to the bottom surface of the ZMW after reaction of the Snap-tag with the benzyl-guanine surface. The mask assembly sterically blocks entry of additional similar moieties, resulting in one mask assembly per ZMW. As shown in FIG. 15B, light of a first wavelength suitable for cleavage of first photocleavable linker (PC1) 1535 can be used to free DNA mass 1545 from ZMW 1510. Polymerase 1550, which is fused to a Clip tag, is covalently attached to the assembly via reaction between the Clip tag and a benzyl-cytosine derivative on the surface bound to Snap 1525. The result is a single polymerase bound to the bottom surface of the ZMW. As shown in FIG. 15C, the polymerase can be freed from the assembly via cleavage at the photocleavable linker (PC2) 1540 using light of a wavelength that is suitable for PC2 but has no effect at PC1." This allows the surface to be reused after a reaction has been completed.

Figure 16A:
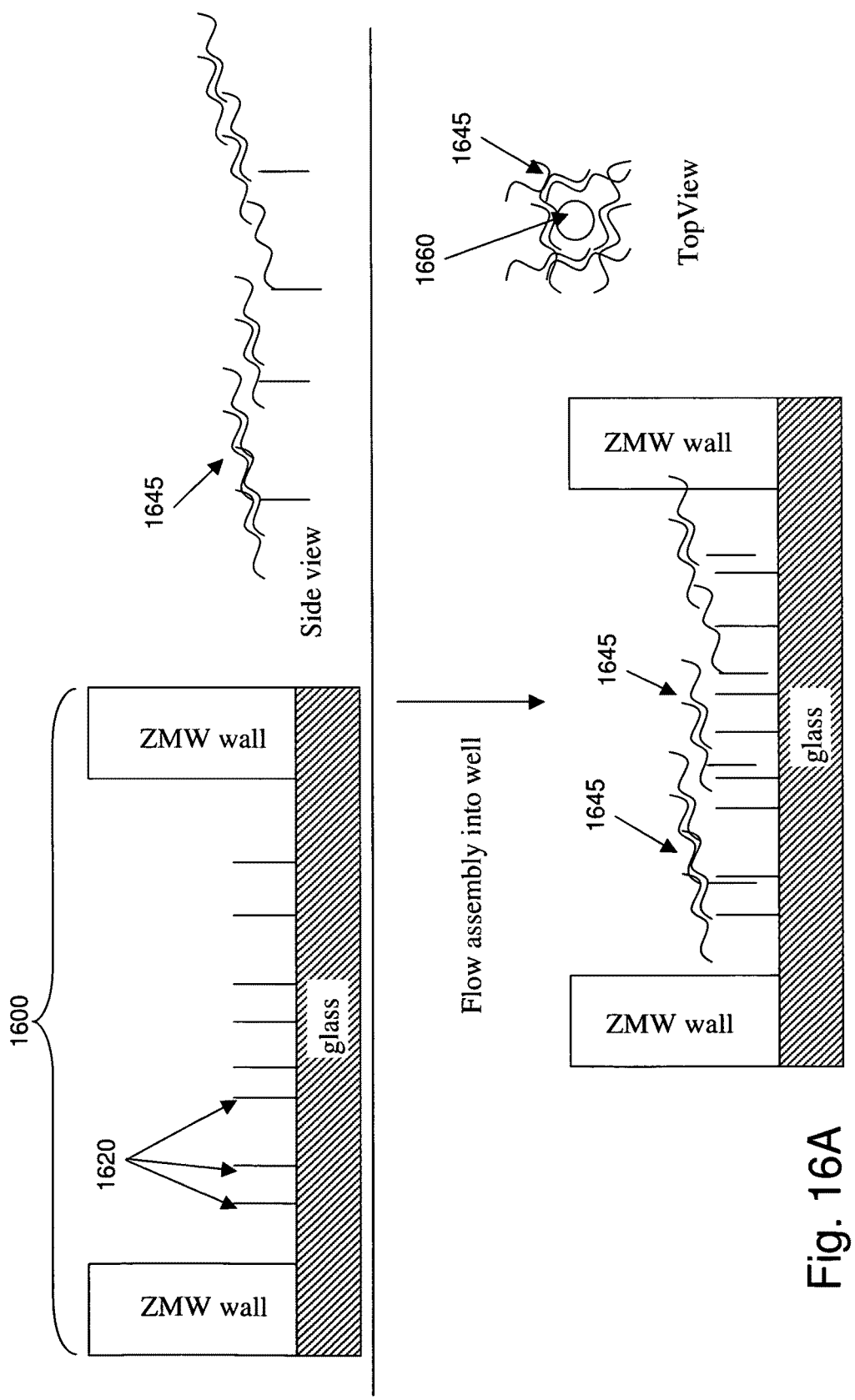
FIG. 16, panels A-B provide an additional schematic example of a DNA masking process.
Figure 16B:
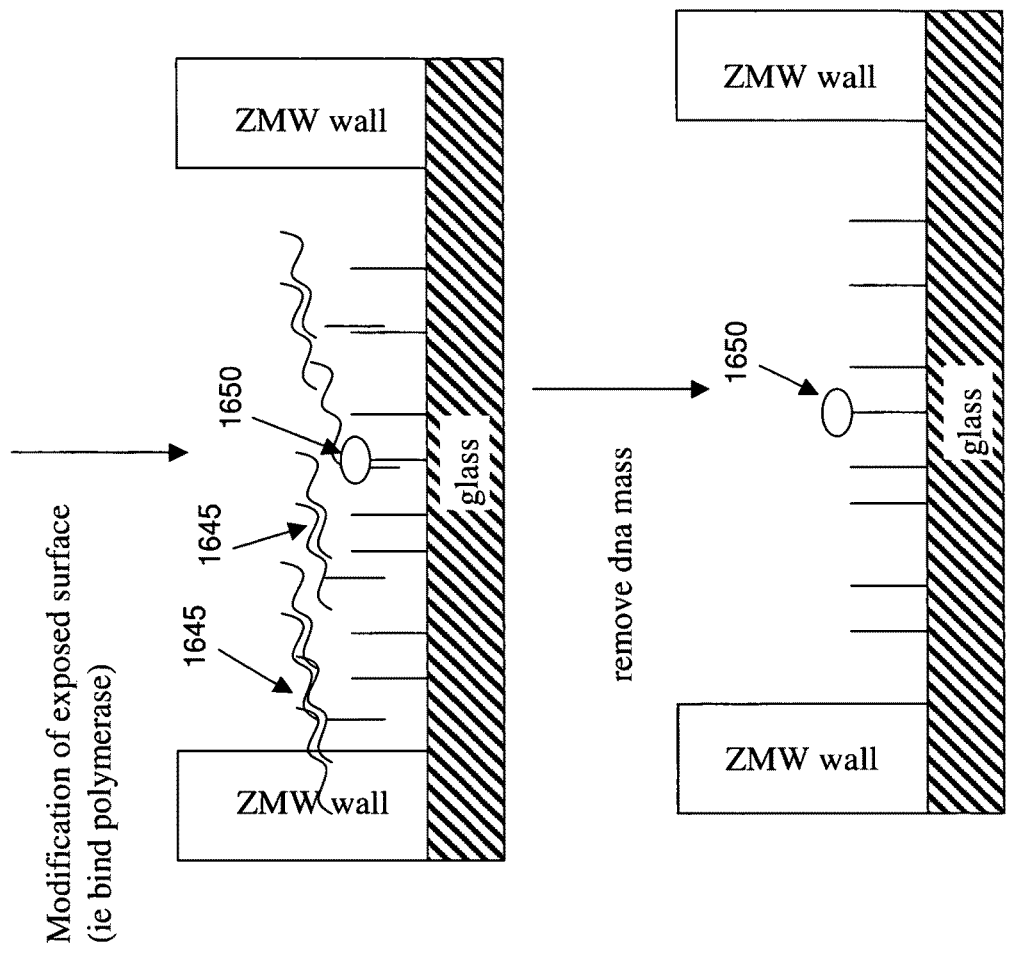

A variant of this approach is shown in FIG. 16, panels A-B. In this variant, the masking DNA is configured to leave a hole in the center upon binding, permitting an analyte to bind through this hole. Alternately, the masking DNA can include a site for binding the analyte, e.g., configured in the center of the mask. In either case, the masking DNA can be removed by cleaving a linker, disrupting a hydrogen bond, or by exonuclease digestion. For example, FIG. 16A shows oligo surface 1620 in ZMW 1600. Giant DNA mass 1645 is flowed into ZMW 1600 to provide hole 1660. Polymerase 1650 binds to oligo surface 1620 through hole 1660. DNA mass 1645 is then removed, e.g., by heat or exonuclease activity, to leave one polymerase per well, which can be centered or positioned according to where the hole is constructed.

Figure 17B:
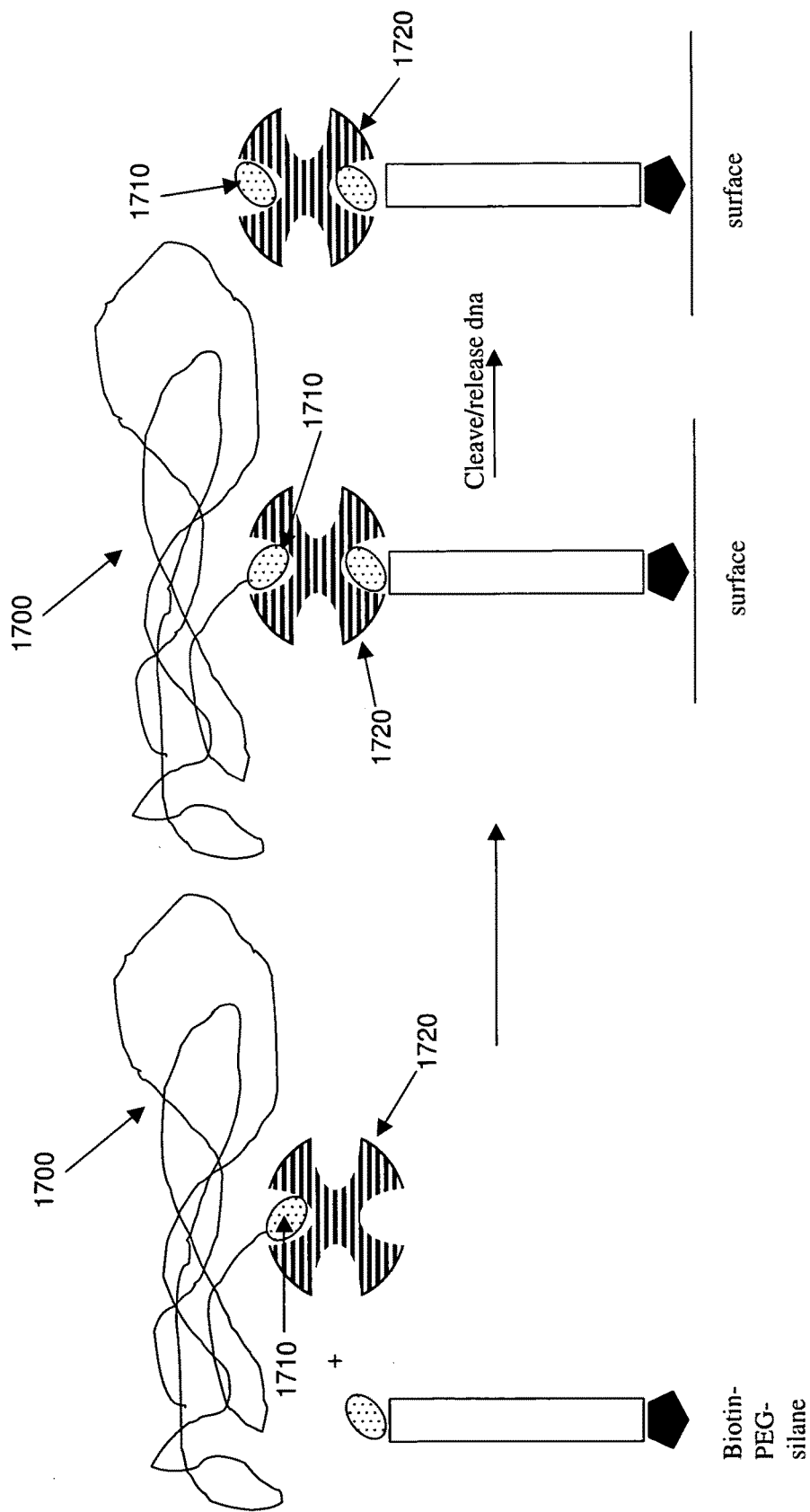
FIG. 17, panels A-B provide a schematic of a DNA masking process that uses a multidentate linker.

In yet another embodiment, as shown in FIG. 17, panels A-B, a DNA structure comprising a biotin site is produced. This site binds to an avidin (other multidentate enzymes and appropriate ligands can be substituted in this method). After binding, the large DNA mask is removed. Sites that comprise avidin will bind to biotinylated analytes. For example, large DNA mass 1700 is created with one exposed biotin, e.g., biotin 1710. This is mixed with avidin 1720 or any other multidentate enzyme. When applied to the surface via another biotin, the large DNA mass sterically excludes anything but the one avidin from binding to the surface. DNA mass 1700 can be cleaved resulting in a single avidin on the surface, which avidin has only one binding site left open (see structure of avidin).

Any of a variety of different binding tags can be added to a well or other reaction region, using standard surface functionalization chemistries. These tags can have DNA strands which hybridize with the assembly and then are cleaved. Different steric exclusion molecules can also be used (e.g., nanodots).

Electrostatically Controlled Loading

In addition to controlling entry into an array feature (well, reaction or observation region, etc.), by controlling the size of particles or other sizing elements that are linked to analytes, similar or complementary effects can be obtained by selecting the charge of the particles, analytes, or the like. For example, a particle that is charged can be attracted to a surface of the array, e.g., where the array has an opposite charge. A charged particle located in an array feature can also block the approach of a similarly charged particle e.g., through electrostatic repulsion. Selecting the charge of particles, analyte-particle complexes, and/or array features can, accordingly, be used to control particle delivery. Charge can be selected by controlling what groups are linked to the particles, complexes or features, and/or by selecting buffer conditions. Charge can also be modified by application of an electric field. For an introduction to electrostatic effects, see, e.g., Chang (1995) *Handbook of Electrostatic Processes* CRC Press, ISBN-10: 0824792548; and Bockris et al. (2001) *Modern Electrochemistry 2A: Fundamentals of Electrodics* Springer 2nd Edition ISBN-10: 0306461676. For an introduction to molecular electrostatic potentials, see Murray (1996) *Molecular Electrostatic Potentials* (*Theoretical and Computational Chemistry*) Elsiever ISBN-10: 0444823530. Size and electrostatic effects can also both be used at the same time to control entry of analytes into an array feature such as a ZMW.

Controlling Analyte/Particle Ratios

In general, it is desirable to attach or package a single analyte molecule of interest to the particle of interest, as the particle will ultimately be analyzed in single molecule analysis reactions. The presence of analyte molecules in excess of 1 in a reaction can lead to difficulties in interpreting analysis data, because of overlapping data sets detected from an analysis reaction.

The virally packaged nucleic acids noted above have an advantage in the context of the invention, because many viruses only package a single nucleic acid per capsid. These viruses are desirably used in the present invention to package a single analyte molecule per particle, as discussed.

Other particle types can also be used in the context of the invention, and the ratios of analyte to particle can be controlled in any of a variety of ways. First, particles can be exposed to levels of coupling reagents (or analytes) that will, on average, attach only a single analyte (e.g., DNA or polypeptide) per particle. That is, the lower the coupling reagent/analyte concentration during the relevant reaction, the more likely that only a single analyte molecule will be attached to the particle. Following coupling, blank particles (particles that lack the analyte) can be removed from any pool of particles to be analyzed by standard methods, such as charge-based separation (DNA, for example, has a net charge, as do many other analytes; particles comprising the DNA or other analyte will have a net charge difference), size based separation (via electrophoresis, chromatography, centrifugation, etc.), use of a FACS device to separate particles bearing labeled analytes from unlabeled particles, or the like. Once the particles bearing an analyte molecule have been separated from unlabeled particles, they can be delivered into array features such as wells of a small well array (e.g., to the ZMWs of a ZMW array) for analyte analysis via, e.g., single molecule analyte detection methods (e.g., single-molecule sequencing, or "SMS").

Delivering Particles to Arrays

Particles can be delivered to an array by methods that are generally used to deliver analyte molecules to the array. For example, delivery methods can include suspending the particles in a fluid and flowing the resulting suspension into the wells of the array. This can include simply pipetting the relevant suspension onto one or more regions of the array, or can include more active flow methods, such as electro-direction or pressure-based fluid flow. In one useful embodiment, the particles are flowed into selected regions of the array, e.g., where a particular particle type is to be analyzed in a particular region of the array. This can be accomplished by masking techniques (applying a mask to direct fluid flow), or by active flow methods such as electro-direction or pressure based fluid flow, including by ink-jet printing methods. Ink jet and other delivery methods for delivering nucleic acids and related reagents to arrays is found, e.g., in Kimmel and Oliver (Eds) (2006) *DNA Microarrays Part A: Array Platforms & Wet-Bench Protocols, Volume* 410 (Methods in Enzymology) ISBN-10: 0121828158; Lee (2002) *Microdrop Generation* (*Nano-and Microscience, Engineering, Technology and Medicine*) CRC Press ISBN-10: 084931559X; and Heller (2002) "DNA MICROARRAY TECHNOLOGY: Devices, Systems, and Applications" *Annual Review of Biomedical Engineering* 4: 129-153. Microfluidic flow can also be used for analyte delivery; these approaches are discussed in more detail herein. Regions of an array can also be selective targets of delivery simply by pipetting the relevant suspension into the correct region of the array.

The arrays can incorporate or interface with fluid channels, e.g., microchannels that can control or direct fluid flow into selected regions of the array. Alternately, the fluid delivery methods can be discrete from the array itself, e.g., using a print head, manual pipettor or robotic pipettor system. A variety of automated fluid delivery systems are available and can readily be used in the context of the invention.

Particle Delivery Examples

FIG. 1 shows array 1 comprising wells 20 and 30 in which viral particles 40 and 50 comprising template nucleic acids 60 and 70 are located. Template nucleic acids 60 and 70 are optionally different nucleic acids, as shown (60 is depicted as being larger than 70). As shown, polymerase enzyme 80 and 90 is fixed to well bottom 100 and 110, located within observation volumes 120 and 130. The Polymerase enzymes pull the template nucleic acids out of viral tail 140 and 150. Detection optics 160 and 170 (e.g., configured for epifluorescent detection) are configured to detect incorporation of labeled nucleotides into a copy template; the optics are coupled to analysis module 180 that assembles sequence from templates 60 and 70 into contigs. In an alternate embodiment, the polymerase enzyme can be fixed to or comprised as part of a viral coat or tail protein, which can, optionally be coupled to the well or other array feature, either through the polymerase or separately. Positioning of the polymerase in the well bottom is schematic, and can be varied as desired, e.g., to move the polymerase closer to or on an edge, or more centrally on the bottom of the well.

Figure 2:
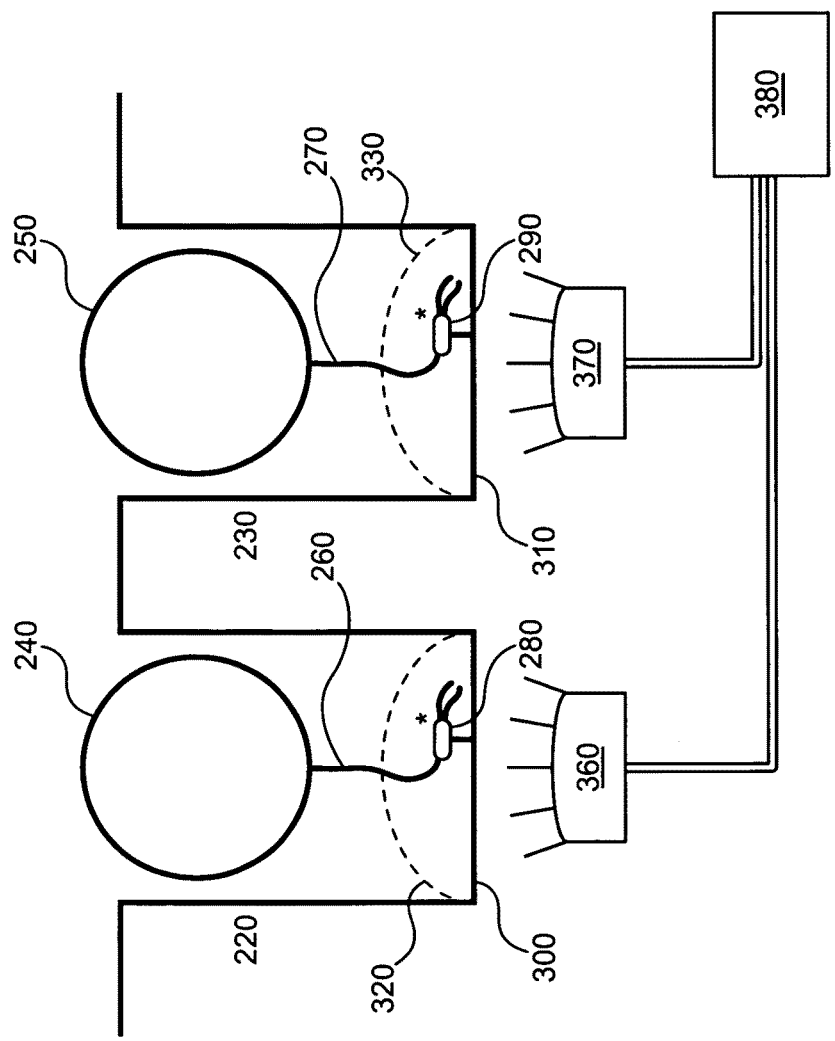
FIG. 2 is a schematic showing particles bound to template nucleic acids in the process of being read by a polymerase in a ZMW.

FIG. 2 shows an alternate arrangement, in which array 2 comprising wells 20 and 30 in which non-viral particles 240 and 250 comprising template nucleic acids 260 and 270 are located. As shown, polymerase enzyme 280 and 290 is fixed to well bottom 300 and 310, located within observation volumes 320 and 330. The Polymerase enzymes sequence the nucleic acid directly on the particle, or after cleavage of the nucleic acids from the particles. Detection optics 360 and 370 (e.g., configured for epiflourescent detection) are configured to detect incorporation of labeled nucleotides into a copy template; the optics are coupled to analysis module 380 that assembles sequence from templates 260 and 270 into contigs.

EXAMPLE

Combined Loading of Enzyme and Substrate

Figure 4:
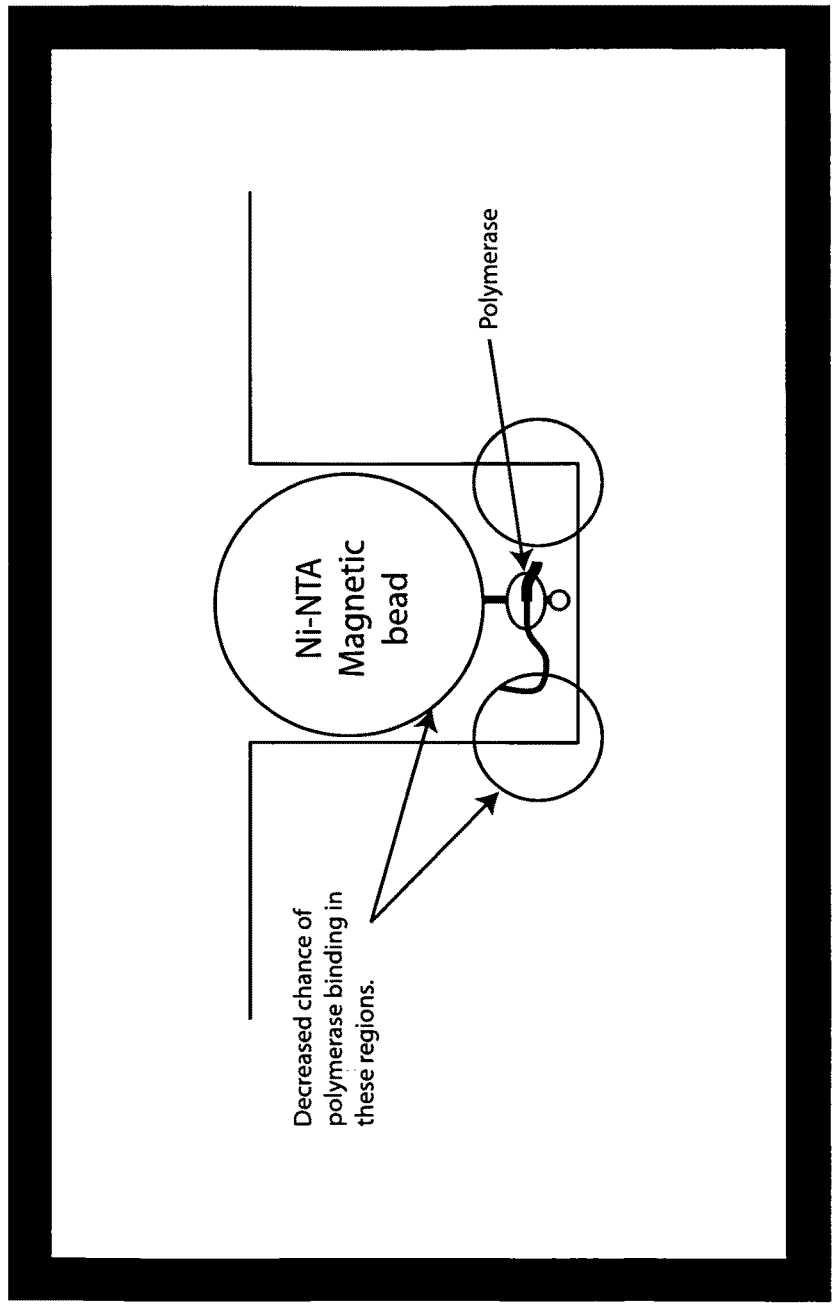
FIG. 4 schematically shows a bead-enzyme-template complex and strategy for non-random loading into a ZMW.

In one embodiment, the analyte of interest, e.g., an enzyme such as a polymerase, is delivered to a reaction/observation site, e.g., in a ZMW. As shown in FIG. 4, a magnetic bead slightly smaller than the ZMW is used to deliver the polymerase plus primer/template complex to the bottom of each ZMW. The magnetic bead is coated with a first tag, e.g., Ni-NTA, which is bound, e.g., by a polyhistidine tag recombinantly fused to the enzyme (e.g., the polymerase), e.g., at the C terminus. A second, e.g., biotin, tag is also linked to the enzyme (polymerase), e.g., at the N terminus. The polymerase can also have an Xa recognition site at the C-terminus. The Ni-NTA bead is delivered to the ZMW and moved into the reaction region via application of a magnetic field. The secondary tag is bound by a binding partner disposed on a surface of the ZMW, e.g., an avidin (alternately, a polyvalent avidin can be bound to the biotin tag, and the polyvalent avidin bound to a biotin on the surface of the ZMW). The first tag is cleaved from the polymerase, e.g., using a site specific endoprotease such as factor Xa (factor Xa preferentially cleaves the c-terminal bond of, e.g., an Ile-Glu-Gly-Arg sequence), e.g., which can cleave a recombinant sequence proximal to the first tag. This results in "touchdown" and binding of the enzyme onto the surface of the ZMW, as well as cleavage of the bead from the enzyme. The bead can then be removed by application of a magnetic field. This results in a single enzyme such as a polymerase being loaded into the reaction/observation region. This size exclusion method increases the probability of enzyme immobilization at the bottom surface of the analysis region, and allows super-Poisson enzyme loading—reducing the probability of multiple enzymes, e.g., polymerases, being immobilized within a single ZMW. Subsequent delivery of a nucleic acid template into the ZMW can proceed as noted herein, e.g., using a viral or other particle to deliver a single nucleotide to the enzyme.

Alternatively, a template nucleic acid can be pre-complexed with the polymerase before or while the polymerase is bound to the bead, optionally along with, e.g., any sequencing primer(s). Delivery of the polymerase as noted above results, in this embodiment, in the simultaneous delivery of the template and the polymerase to the reaction/observation region.

In either case, the magnetic beads are linked to the enzyme by mixing a monodisperse population of Ni-NTA (or other tag) coated beads in a ratio of about 1:1 with the enzyme, or with enzyme and template (or with enzyme that is prebound to template). For these embodiments, magnetic beads and populations of, e.g., monodisperse magnetic beads coated with Ni-NTA or other tags are a feature of the invention, as are mixtures of such beads with an enzyme (e.g., a recombinant polymerase comprising an appropriate tag binding partner such as a polyhistidine site) or an enzyme-template complex.

Thus, a polymerase or other enzyme comprising a factor Xa-His site to bind to the bead and to provide a protease site for subsequent cleavage from the bead is also a feature of the invention. This tag is optionally located relatively proximal to the active site, as this tag is removed by the protease. Thus, for a polymerase, this tag/cleavage site can be located at the C-terminal end of the enzyme. The polymerase can also include a biotin or other tag or tag binding site as well, for linking to the ZMW or other reaction or observation volume substrate. This tag can be located distal to the active site, to prevent inhibition of the activity of the surface bound enzyme, e.g., by linking the tag at the n-terminal end of the enzyme. A wide variety of constructs for linking active enzymes to surfaces can be found in Hanzel et al. ACTIVE SURFACE COUPLED POLYMERASES, WO 2007/075987 and Hanzel et al. PROTEIN ENGINEERING STRATEGIES TO OPTIMIZE ACTIVITY OF SURFACE ATTACHED PROTEINS, WO 2007/075873).

Washing steps can be used to eliminate any polymerase or polymerase template complexes that are not complexed with the bead, e.g., using standard washing steps, e.g., by pelleting beads bound to enzyme or enzyme complexes in a magnetic field. After delivery of the bead into the reaction/observation region, any unbound tag binding sites (e.g., avidin or biotin) on a surface of the region (e.g., the walls or bottom of a ZMW) can be blocked, e.g., by adding an excess of unbound cognate binding partner, thereby preventing binding of additional components to the surface(s).

Combination Loading Techniques

A variety of components are loaded as appropriate to the relevant assay into the reaction/observation regions (e.g., wells, size delimited regions, ZMWs, charge delimited regions, etc.) of the relevant arrays. As is noted in detail above, these components can include nucleic acids, enzymes such as polymerases (e.g., in sequencing applications), reagents used in the detection reaction (e.g., nucleotides or nucleotide analogues in the context of a sequencing reaction) and the like. In addition to the delivery methods of the invention, e.g., particle-based delivery, any previously available delivery method can be used, separately or in combination with those of the invention, to deliver additional reaction components to the regions.

Analytes or other reaction components can be fixed into reaction/observation regions using the techniques of the invention or other available techniques such as blocking and masking strategies, e.g., where a specific number or type of components in each reaction/observation region is desirable, and/or components can simply be loaded into the regions in solution, e.g., where the components are reagents to be used in a reaction of interest. All of the discussion herein regarding surface attachment chemistries applies to the attachment of non-analyte components in the wells of the array. For example, Foquet et al. SUBSTRATES AND METHODS FOR SELECTIVE IMMOBILIZATION OF ACTIVE MOL- ECULES (U.S. Ser. No. 60/905,786, filed Mar. 7, 2007 and U.S. Ser. No. 12/074,716, filed Mar. 5, 2008) provides methods, compositions and fabrication strategies for immobilizing components such as polypeptides in a ZMW, e.g., by incorporating a functionalizable element into the ZMW.

Constricting Array Feature Diameter or Charge

In one useful variant, the sizing or electrostatic control moiety is not attached to an analyte of interest, but is added to the ZMW or other array feature prior to loading of the analyte. This approach constrains the overall geometry and/or charge of the array feature to effectively reduce the diameter of the feature, or change its charge, or both, such that only a single analyte can fit into a binding site within the feature (e.g., only a single analyte can reach the bottom of a ZMW). The size or charge of the moiety that is used to constrain the diameter or alter the charge of the ZMW or other array feature can be varied, depending on the size of the feature and the size of the analyte or analyte complex. For example, where the analyte complex is about 10 nm in diameter, and the ZMW is about 100 nm in diameter, 40 nm sizing moieties are selected to reduce the effective diameter of the ZMW from about 100 nm to less than about 20 nm. Typical size ranges for relevant array features can be, e.g., 20-200 nm in diameter, with typical sizing moieties being about 5 nm to about 90 nm in size (e.g., about 5, 10, 15, 20, 25, 30, 35, 40, 45, 50, 55, 60, 65, 70, 75, 80, 85, or 90 nm in size).

In one example, a typical streptavidin-polymerase-template complex has a MW of ~180 kD which is close to that of IgG, having a size range of 10 to 15 nm. For a ZMW with a nominal diameter of 100 nm, binding of 40 nm beads or other sizing moieties or particles on an Al sidewall of the ZMW can reduce the accessible hole size to ~20 nm, thereby limiting the number of polymerase complexes that can reach the bottom of the ZMW and bind to a biotin moiety located on the bottom, to approximately one complex. Furthermore, if the 40 nm beads are bound to the outer diameter of the ZMW hole, the center of the bottom of the ZMW hole is exposed, helping to center the analyte complex in the ZMW (which can make it easier to read signal information from the ZMW).

Figure 5:
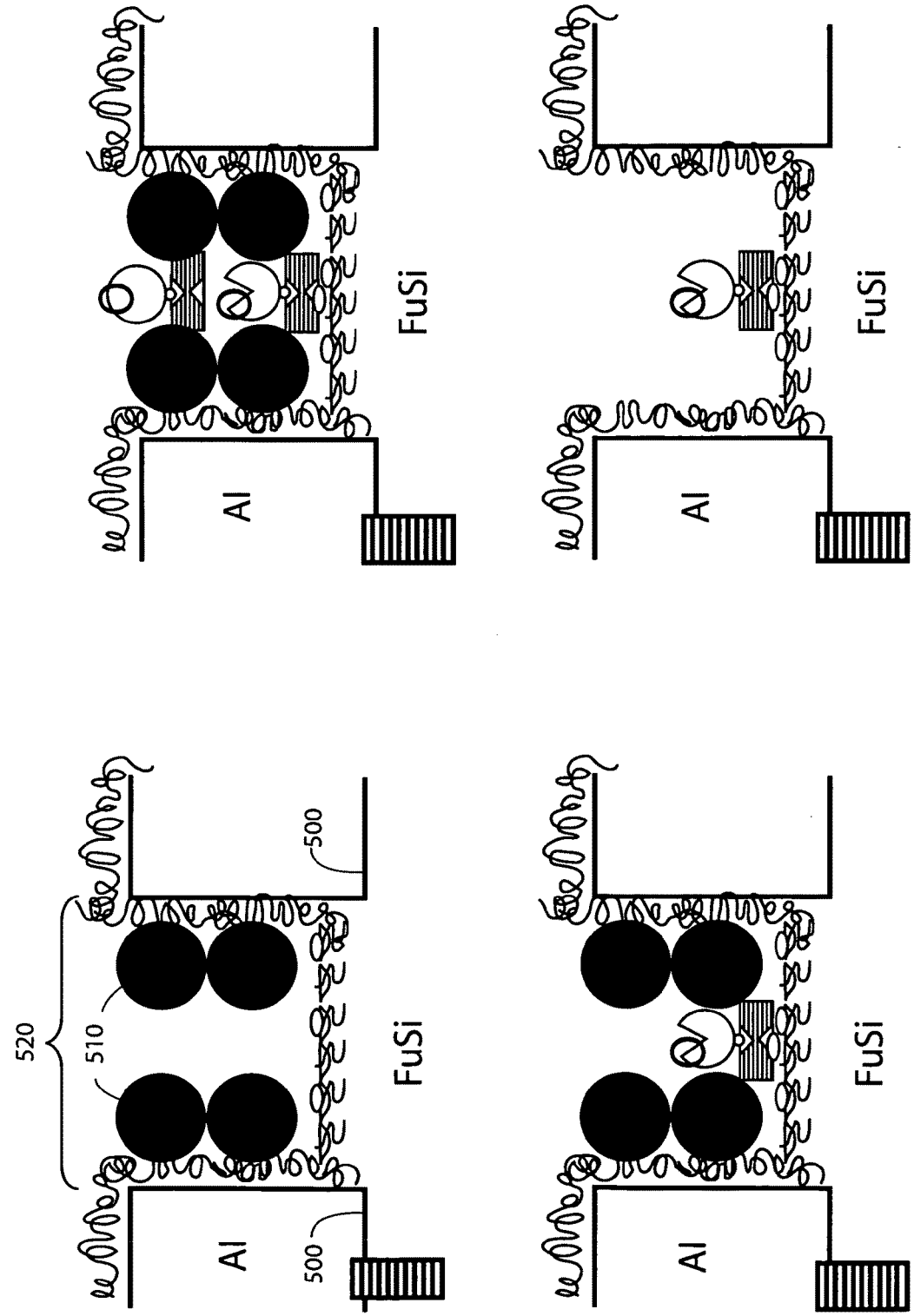
FIG. 5 schematically depicts temporary constriction of a ZMW using beads bound to the side walls of the ZMW, and the resulting single molecule binding of an analyte in the ZMW.

Any of a variety of interactions between the outer diameter of a ZMW hole or other array feature and a bead or other sizing moiety can be used. For example, beads can be coated with binding agent A, for example, a 6His peptide. A complementary binding partner B is attached on the walls of the array feature (e.g., ZMW hole walls). An example of a binding agent B that is complementary to the 6His peptide would be an NTA group bound to a phosphonate polymer. Al surfaces (e.g., ZMW hole walls) treated with this phosphonate NTA polymer will bind agent A—functionalized beads; at high bead concentrations, the Al sidewall of ZMWs in an array are covered with a monolayer of beads. A high concentration of, e.g., a Streptavidin-polymerase-template is introduced into this system so that all ZMWs are loaded. Since the accessible hole diameter has been reduced, for example to about 10 or 20 nm, only one analyte will be able to bind to an analyte binding moiety located at the bottom of the array feature. For example, the bottom surface of the ZMWs of an array can be functionalized with, e.g., a biotin silane moiety, typically at low concentration, to further reduce the chances that multiple analytes will bind. The analyte, e.g., an avidin-polymerase-template complex binds to the biotin moiety. Excess unbound analyte is removed by rinsing several times. If desired, beads can be dissociated from the sidewalls by appropriate chemistry, e.g., in the case of 6His-phosphonate NTA, by lowering the pH below 6 and/or adding excess 6His peptide; the beads can then be washed away. See FIG. 5, which provides examples of constricting array features in ZMWs. ZMW hole walls 500 include sizing moieties 510, e.g., beads, which reduce the diameter of ZMW hole 520.

Placing or Fabricating Analyte Binding Nanostructures into Array Features

One general approach of the invention to increasing the loading efficiency of single molecule analytes into an array of reaction regions includes creating a single binding site for the analyte within each of the reaction regions, and then completely loading the single binding sites. Washing steps can be used to remove unbound analytes from the array, resulting in essentially complete loading of analytes on the binding sites, leading to one analyte being loaded per reaction site. This yields an array of reaction sites, such as an array of ZMWs, having most or all of the reaction regions of the array loaded with a single molecule of the analyte of interest. While this approach is particularly well-suited to loading of single analyte molecules into reaction regions, it will be appreciated that the same approach can be used to load more than 1 molecule, e.g., by creating more than one binding site per reaction region, and loading the multiple binding sites.

In one example implementation, this aspect of the invention provides a general method for fabricating zero-mode waveguide (ZMW) or other reaction region structures with a single nanostructure (e.g., a nanodot) inside the ZMW hole/ reaction region or other array feature. The diameter of a typical ZMW hole is between, e.g., about 50 nm and about 120 nm, which is large enough to accommodate several copies of most reaction analytes (polymerase molecules, templates, etc.). The nanostructure in the hole or other reaction region, etc., is fabricated to be small enough, relative to the analyte, that only a single molecule of the analyte can bind to the nanostructure (alternately, the nanostructure can include just a single binding site for the analyte). Example nanostructures include metal nanodots, metallic nanostructure, dielectric nanostructures, or semiconductor material nanostructures that can be functionalized using standard chemistries to display binding moieties that can be bound by an analyte of interest.

For example, the presence of a functionalized metal nanodot or other nanostructure provides a binding site e.g., on the bottom surface or other target portion of a reaction region (e.g., a ZMW), etc., that is sufficiently limited in area such that a single analyte (e.g., polymerase or other enzyme) can be immobilized, e.g., for DNA sequencing or other single-molecule reactions. For example, noble metals, such as gold, silver, or platinum can be functionalized to form metal thiolates using alkanethiols, forming a binding site for the analyte.

Either the nanoparticles, the analytes, or both are optionally functionalized in order to attach the analytes to the nanoparticles. Similarly, an intermediate binding moiety such as a biotin or avidin can be functionalized. For instance, nucleotides or polypeptides herein are optionally functionalized with alkanethiols to facilitate attachment to noble metals such as gold. For example, nucleotides can be functionalized at their 3'-termini or 5'-termini (e.g., to attach them to gold nanoparticles). See Whitesides, *Proceedings of the Robert A. Welch Foundation 39th Conference On Chemical Research Nanophase Chemistry*, Houston, Tex., pages 109-121 (1995) and Mucic, et al. *Chem. Commun.*, 1966, 555-557. Functionalization via alkanethiol attachment strategies is also optionally used to attach analytes to other metal, semiconductor or magnetic nanoparticles. Additional or alternate functional groups used in attaching analytes to nanoparticles can include, e.g., phosphorothioate groups (see, e.g., U.S. Pat. No. 5,472,881), substituted alkylsiloxanes (see, e.g. Burwell, *Chemical Technology*, 1974, 4:370-377, Matteucci, *J. Am.*

*Chem. Soc.*, 1981, 103:3185-3191 (1981), and Grabar, et al., *Anal. Chem.*, 67:735-743). Nucleotides terminated with a 5' thionucleoside or a 3' thionucleoside can be used for attaching nucleotides/oligonucleotides to solid nanoparticles. See also Nuzzo, et al., *J. Am. Chem. Soc.*, 1987, 109:2358; Allara, *Langmuir*, 1985, 1:45; Allara, *Colloid Interface Sci.*, 1974, 49:410-421; Iler, *The Chemistry Of Silica*, Chapter 6, (Wiley 1979); Timmons, *J. Phys. Chem.*, 1965, 69:984-990; and Soriaga, *J. Am. Chem. Soc.*, 1982, 104:3937. Further guidance regarding combinations of nanoparticles and analytes can be found in, e.g., U.S. Pat. No. 6,979,729 to Sperling et al.; U.S. Pat. No. 6,387,626 to Shi et al.; and U.S. Pat. No. 6,136,962 to Shi et al.; and U.S. Pat. No. 7,208,587 to Mirkin et al. Additional details regarding suitable linking chemistries is found herein.

One example of the overall strategy is to fabricate a nanostructure array comprising Au nanostructures, followed by immobilization of a polymerase, template nucleic acid, or other analyte using typical functionalization and binding chemistries, e.g., to provide an analyte bound nanostructure, e.g., AuS—$(CH2)_x(CH_2H_4O)_y$-Biotin-Avidin-Analyte (e.g., AuS—$(CH2)_x(CH_2H_4O)_y$-Biotin-Avidin-Polymerase). The incorporation of metal nanostructures in ZMW holes or other reaction regions is not limited by Poisson statistics; thus, binding of the polymerase or other analyte to the nanostructures provides high yields of reaction regions in an array that each have a single active polymerase or other analyte.

Figure 6C:
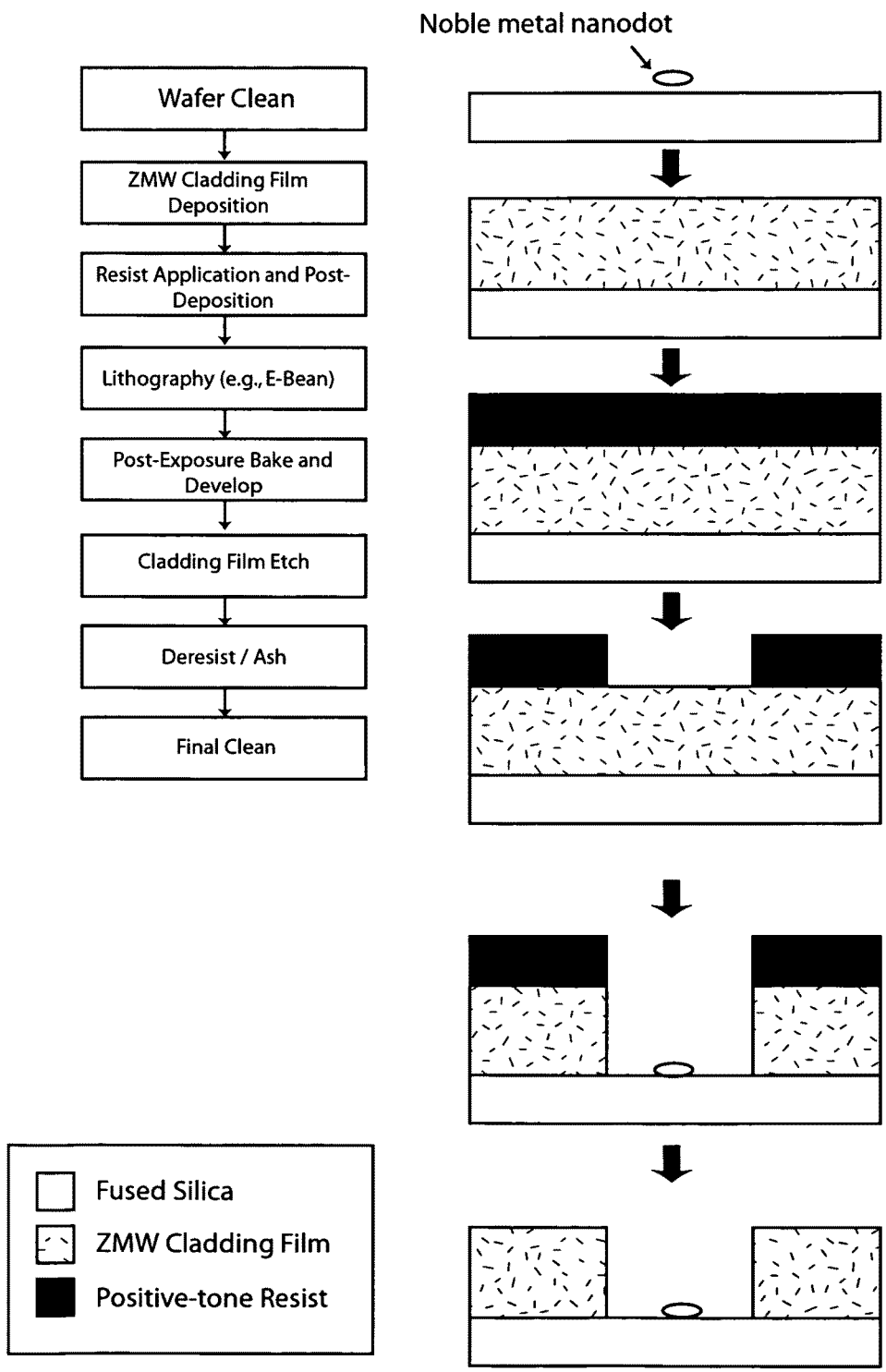
FIG. 6, panel A provides a photomicrograph of an array fabricated using a Vistec VB300 Electron Beam System and positive-tone chemically-amplified resist. Panel B shows a schematic and photomicrograph illustrating formation of a Ge nanowire with a Au—Ge tip. Panel C shows a flow chart and schematic for formation of a ZMW nanostructure over a nanodot array.

Overall fabrication approaches to making the array of nanostructures in reaction regions optionally use available process technology from semiconductor fabrication, photomasking, and MEMS manufacturing. For example, an array of metal nanodots can be formed using e-beam lithography, Deep Ultra-Violet (DUV) lithography, nanoimprint, or other available lithography process, or other available patterning techniques. Available commercial e-beam equipment and photoresist technology are sufficient to meet the size and positioning resolution requirements, e.g., as shown in FIG. 6A. The array in this Figure was fabricated using a Vistec VB300 Electron Beam System and positive-tone chemically-amplified resist. The steps in this process can include, e.g.: (1.) surface cleaning of a fused silica or synthetic quartz wafer, e.g., using conventional industry standard RCA protocols (also known as "standard cleaning" or SC-1), or using Piranha cleaning (also known as "piranha etching," e.g., using a mixture of sulfuric acid and hydrogen peroxide), see also, Rastegar "Cleaning of Clean Quartz Plates," Surface preparation and Wafer Cleaning Workshop, Austin, April 2005; (2) application of a resist adhesion promoter such as, but not limited to, hexamethyldisilazane; (3) spin coating and post-application bake of a positive-tone. chemically-amplified resist; (4) e-beam lithography; (5) post-exposure bake; (6) photoresist development; (7) photoresist descum; (8) metal deposition; and (9) deresisting. For additional details in wafer fabrication and lithography, see, e.g., Eynon and Wu (2005) *Photomask Fabrication Technology*, New York, McGraw-Hill; Alexe (Editor), Gösele (Editor), Gösele (Author) (2004) *Wafer Bonding* Springer ISBN-10: 3540210490; Luo (2004) *Integrated Modeling of Chemical Mechanical Planarization for Sub-Micron IC Fabrication: from Particle Scale to Feature, Die and Wafer Scales* ISBN-10: 354022369X; Madou (2002) *Fundamentals of Microfabrication: The Science of Miniaturization, Second Edition* CRC; and Atherton (1995) *Wafer Fabrication: Factory Performance and Analysis* (The Springer International Series in Engineering and Computer Science) Springer ISBN-10: 0792396197.

If metals such as Au, which have poor adhesion to SiO, are used, then an adhesion promoter can be deposited using vapor phase deposition. One example for an adhesion promoter for Au on SiO is octadecyltrichlorosilane (Szunerits et al. (2006) 22:10716-10722). Other alternatives to improve adhesion include using an interfacial metal such as Cr or Ti during the metallization step. Further details regarding available deposition methods, including vapor and thin film deposition, can be found, e.g., in Harsha (2006) *Principles of Vapor Deposition of Thin Films*, Elsevier Science ISBN-10: 008044699X; Dobkin and Zuraw (2003) *Principles of Chemical Vapor Deposition* ISBN-10: 1402012489; Mahan (2000) *Physical Vapor Deposition of Thin Films* ISBN-10: 0471330019; Mattox (1998) *Handbook of Physical Vapor Deposition (PVD) Processing (Materials Science and Process Technology Series)* Noyes Publications ISBN-10: 0815514220; and Smith (1995) *Thin-Film Deposition: Principles and Practice* McGraw-Hill Professional ISBN-10: 0070585024.

For the case when the nanodot is gold, its diameter and height in a ZMW or other reaction region can be modulated and its adhesion to the substrate, if no adhesion promoter is used, can be achieved by exposing the array to germane ($GeH_4$), e.g., as in Adhikari et al. (2007) *J. Appl. Phys.* 102: 94311-94316. Au catalyzes decomposition of germane by the reaction $GeH_4 \rightarrow Ge + 2H_2$ (Woodruff et al. (2007) *Nano Lett.* 7:1637-1642) resulting in a Ge nanowire with a Au—Ge tip as shown in FIG. 6B. As shown in FIG. 6B, solid/liquid nanoparticle 610 is situated upon solid flat substrate 620 in the presence of $GeH_4$ vapor 640, resulting in the formation of solid Ge nanowire 660 with a tip composed of solid/liquid nanoparticle 650. The diameter and length of the nanowire can be controlled by modulating process conditions and exposure time to $GeH_4$. Prior to exposing the array to $GeH_4$, the substrate can be exposed to high temperatures (ca. 300 degrees C.) to form spheres on the substrate. Anchoring the nanodot, e.g., through a germanium nanowire to the substrate, is not required for this class of embodiments.

The ZMW or other reaction region array structure can be formed using available fabrication methods, e.g., forming the reaction region array over the completed nanostructure array, such that the nanostructures reside in a desired portion of each of the reaction regions (e.g., in the bottom of ZMW holes in a ZMW array). An example process for producing an array of ZMWs or other suitable reaction regions can include: (1) surface cleaning, with the cleaning process type and recipe being based on, e.g., the effectiveness of the deresisting process used at the end of the production of the nanostructure array, adhesion strength of the nanodots to the substrate and accumulated adventitious contamination due to time between steps and any storage environment; (2) deposition of a ZMW (or other array feature) cladding metal such as aluminum; (3) spin coating and post-application bake of a positive-tone, chemically-amplified resist; (4) e-beam or other suitable lithography; (5) post-exposure bake; (6) photoresist development; (7) photoresist descum; (8) etch of the cladding metal; and (9) deresisting and final cleaning. For an example illustration of this process, see the flow diagram and illustration shown in FIG. 6C. Image placement or registration errors of current electron beam technology is sufficiently to provide accurate patterning of the zero mode waveguide structures over the nanodot array, e.g., over a 6-inch square area. See, e.g., Saitou (2005) "E-Beam Mask Writers," in *Handbook of Photomask Manufacturing Technology*, edited by S. Rizvi, New York, Taylor and Francis. For example, the VB300 Electron Beam Lithography System from Vistec can achieve less than a 10 nm error in patterning. Available e-beam systems used for photomask fabrication such as those from Nuflare Technology and JEOL have comparable image placement areas over a 6-inch square area Eynon and Wu (2005) *Pho-*

*tomask Fabrication Technology*, New York, McGraw-Hill; International Technology Roadmap for Semiconductors, 2007 Edition. The cladding metal lithography technique for patterning steps, nanodot metal adhesion promoters, and substrate material can be varied with still accomplishing the main objective of the invention. Additional details on example implementations that provide nanostructures in array regions such as ZMWs are provided below.

Fabricating or Immobilizing Nanoparticles in Arrays

One feature of the invention is the ability to achieve efficient high density loading of single molecules of interest into analysis regions of an array. One class of embodiments achieves higher levels of single (or other desired number) occupancy loading into arrays or reaction regions such as ZMWs by fabricating a nanoparticle deposited or fabricated in the reaction region. The nanoparticle is small enough that only one (or another desired number) analyte can bind to the particle. While this approach is particularly useful for loading single molecules of analyte, e.g., for single molecule reactions (e.g., SMS), it will be appreciated that a desired number of particles can be deposited or fabricated in selected reaction regions to achieve specific loading of any desired specific number of analytes.

The nanoparticle(s) optionally include(s) an easily functionalized surface to permit attachment of an analyte of interest. For example, the particle(s) can comprise gold, which can be functionalized with standard thiol chemistries. Individual particles are small enough that only a desired number of analytes (e.g., one) can bind to the particle, due to steric interactions of the analyte at the surface of the particle.

Figure 7:
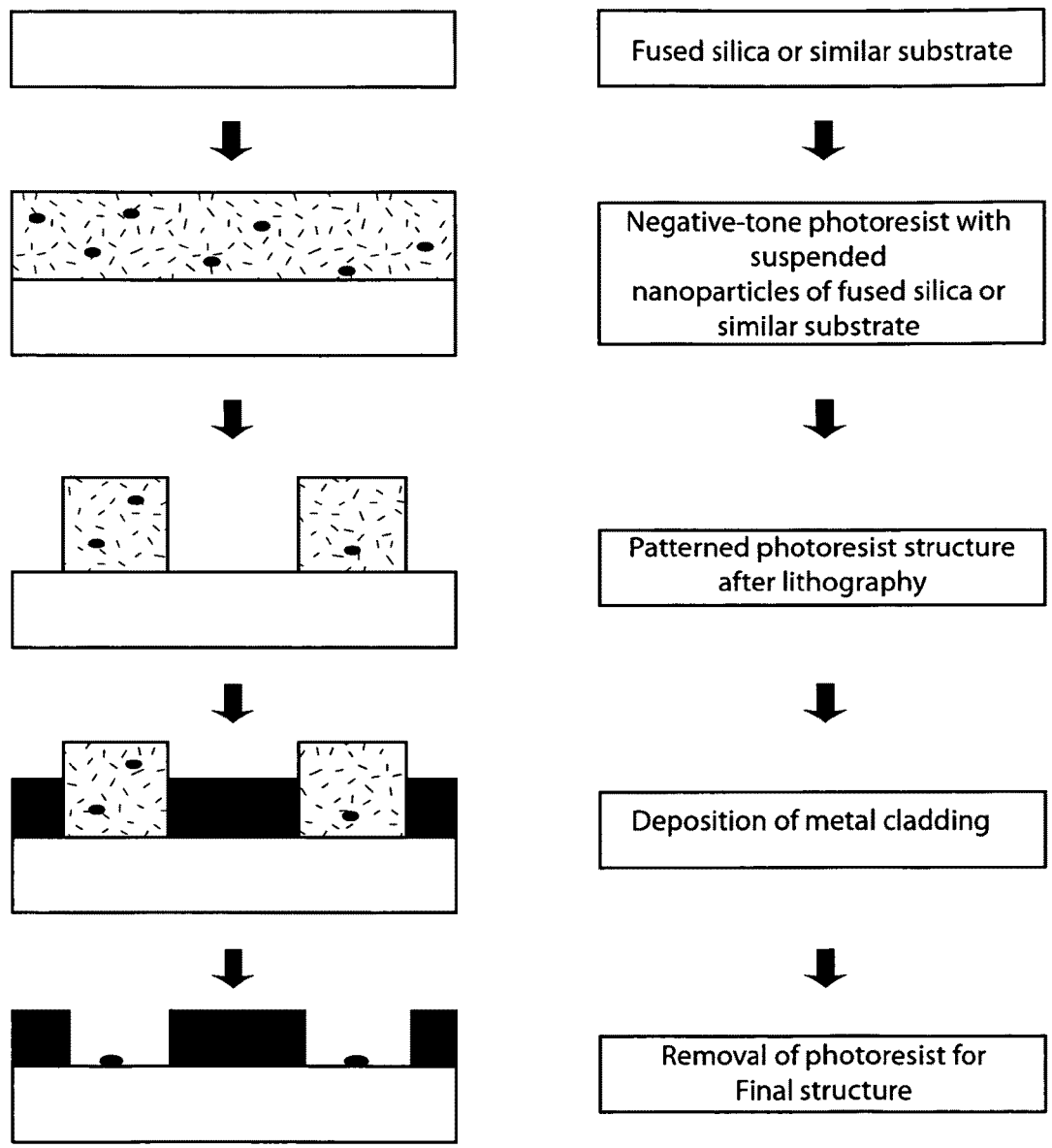
FIG. 7 provides a flow chart and schematic illustration of a process for immobilization of nanoparticles in a ZMW.

For example, immobilization of, e.g., metal nanoparticles can be performed by the process shown in FIG. 7. Metal nanoparticles of sizes ranging from 10-100 nm are suspended in a negative-tone photoresist and spun onto a fused silica, synthetic quartz, borosilicate, or a similar substrate. Using e-beam lithography, Deep Ultra-Violet (DUV) lithography, nanoimprint, or other available lithography process, pillars ranging from 50-200 nm in diameter are fabricated. A metal cladding film such as aluminum is deposited onto the structure. The photoresist is removed in a manner that leaves a single nanoparticle in each newly-created hole (e.g., comprising a reaction region (e.g., a ZMW). Biotin/avidin/polymerase can be tethered on the nanoparticle (e.g., Au—S—$(CH_2)x(C_2H_4O)y$-biotin). The nanoparticles are small enough that only one polymerase or other analyte of interest can fit on them in the reaction region, effectively limiting the number of analytes in the reaction region. During subsequent analyte loading processes, the analyte can be loaded into the reaction regions at relatively high concentrations, effectively loading most or all of the particles with an analyte molecule. Excess analyte is washed from the reaction region, resulting in a high percentage of the reaction regions acquiring a single polymerase or other analyte.

Depositing a Small Binding Site Island in a ZMW Using Directional Deposition

In one example approach, methods, systems and compositions for depositing a small island or dot at the bottom of an array feature (e.g., ZMW) or even simply on a flat substrate to create a heterogeneous surface of phase determining features, e.g., for single molecule attachment are provided. As above, the island/dot can be, e.g., a metallic, dielectric, or semiconductor material on which a polymerase or other analyte can be immobilized by means of a linker molecule such as a biotin-terminated poly(ethylene glycol)alkanethiol, as noted in more detail above.

Figure 8A:
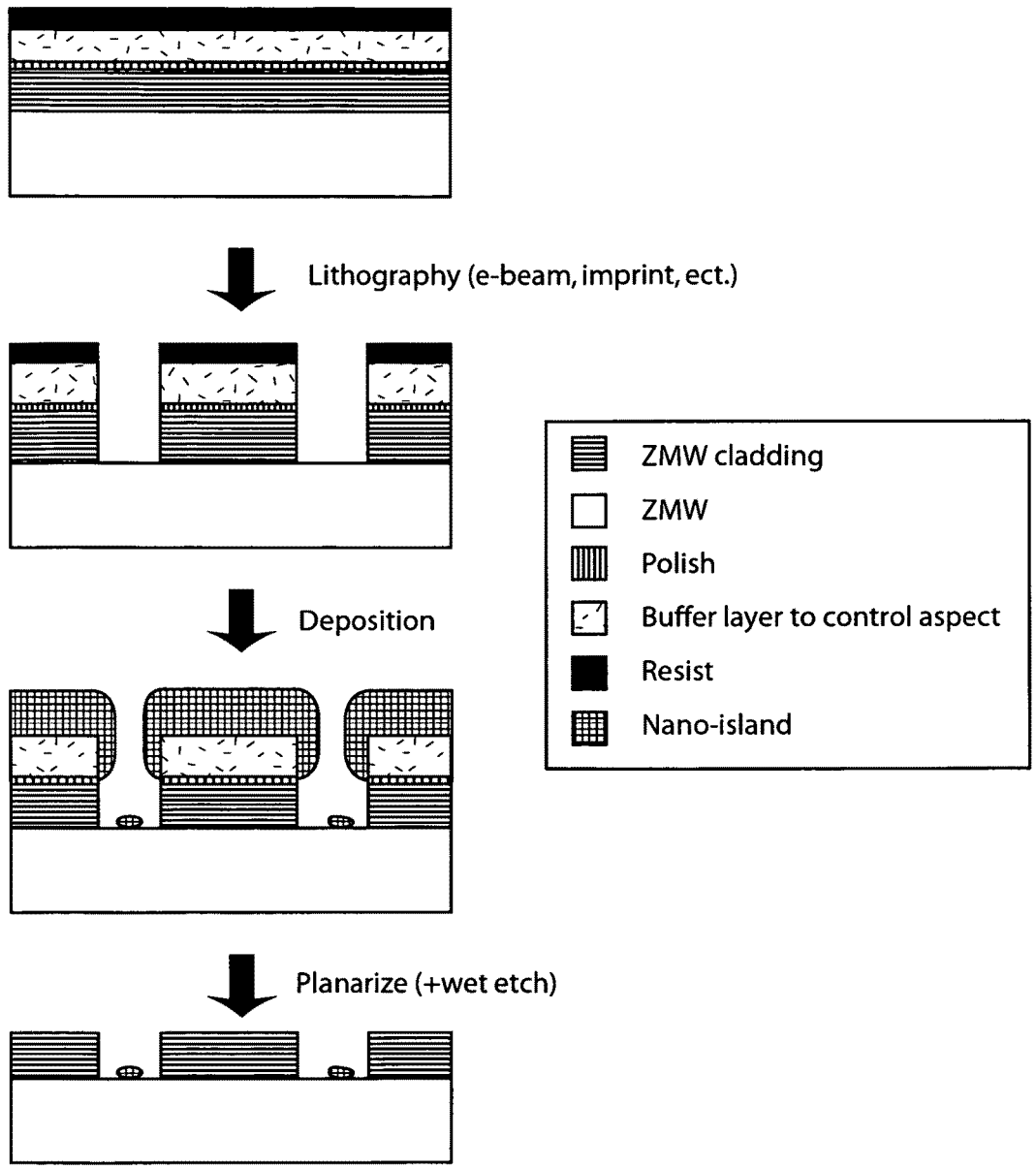
FIG. 8A provides a schematic illustration of a procedure for forming nanoparticles in ZMWs.

In one aspect, in order to make islands sufficiently small that only one polymerase can bind to one island, a high aspect ratio structure is used in conjunction with nonspecific, directional deposition. This can include, but is not limited to, physical vapor deposition (PVD) such as sputtering, e-beam evaporation, and thermal evaporation, or chemical vapor deposition (CVD) such as low-pressure CVD, plasma-enhanced CVD, or high density plasma CVD. Similar approaches have been used for fabricating nanowires of similar length scales, demonstrating the basic feasibility of this approach. As shown in FIG. 8A, a high aspect ratio pattern is created by adding a buffer film between a photoresist and a cladding film. Alternatively, a bilayer resist can be used in place of a single-layer resist/buffer layer to create the necessary dimensions. After patterning the ZMW hole or other array feature with the desired aspect ratio, a film is deposited over the entire structure by PVD or CVD. By using suitable aspect ratios and deposition conditions, a "breadloaf" shaped structure forms above the film, creating a mask through which a small diameter restricts the area of deposition onto the substrate. The breadloaf-like structure forms isotropically around, e.g., a ZMW hole, naturally aligning the island in the center of the ZMW cavity. The resulting island surface can be functionalized with linker to bind the desired enzyme, e.g., a polymerase.

Figure 8B:
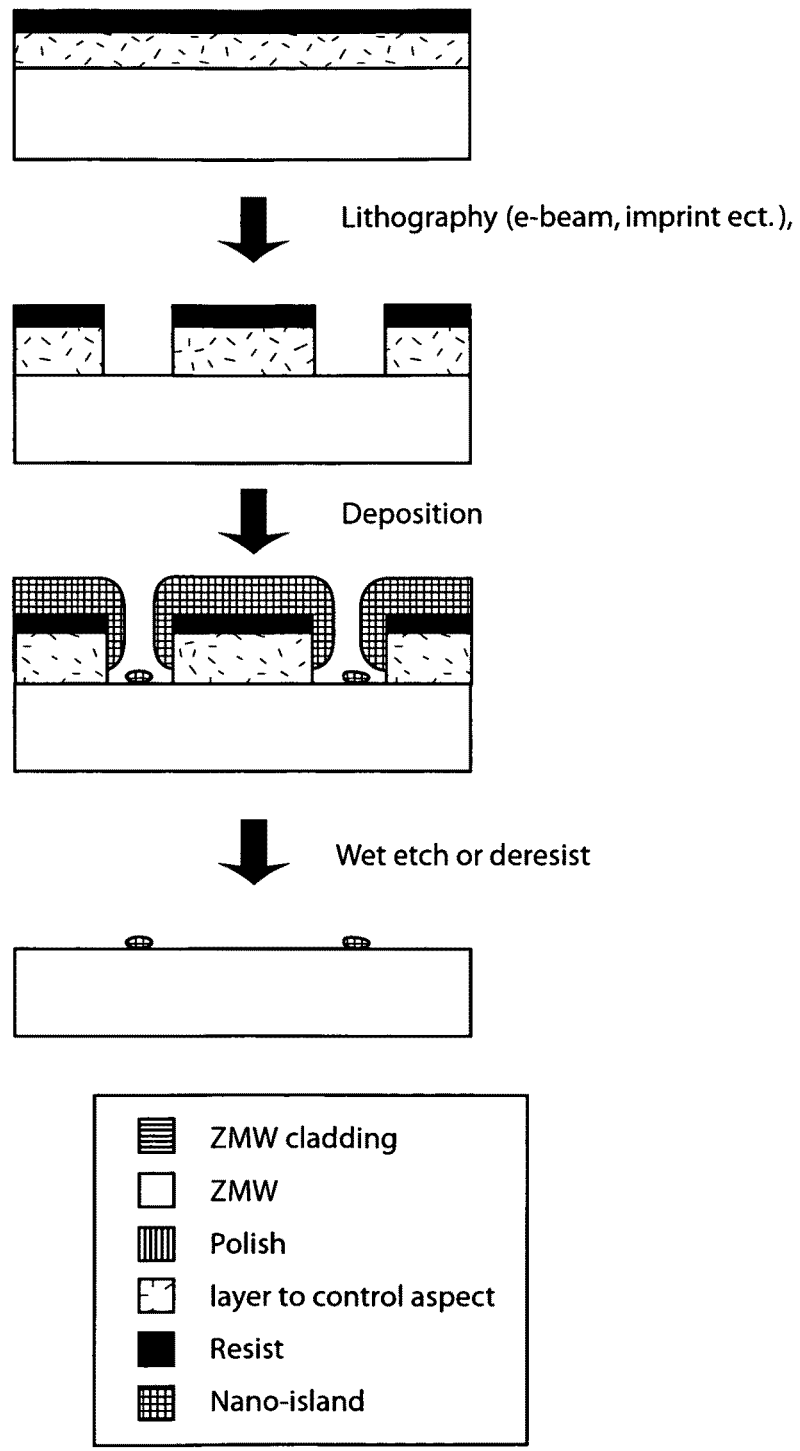
FIG. 8B provides a schematic of a process flow for flat substrates.

This overall process can also be adopted to form small dots that are sized for a single polymerase on flat substrates. These substrates can be used with single molecule analysis techniques that do not require a ZMW structure, such as Total Internal Reflectance Fluorescence (TIRF). A process flow for flat substrates is shown in FIG. 8B.

Figure 9A:
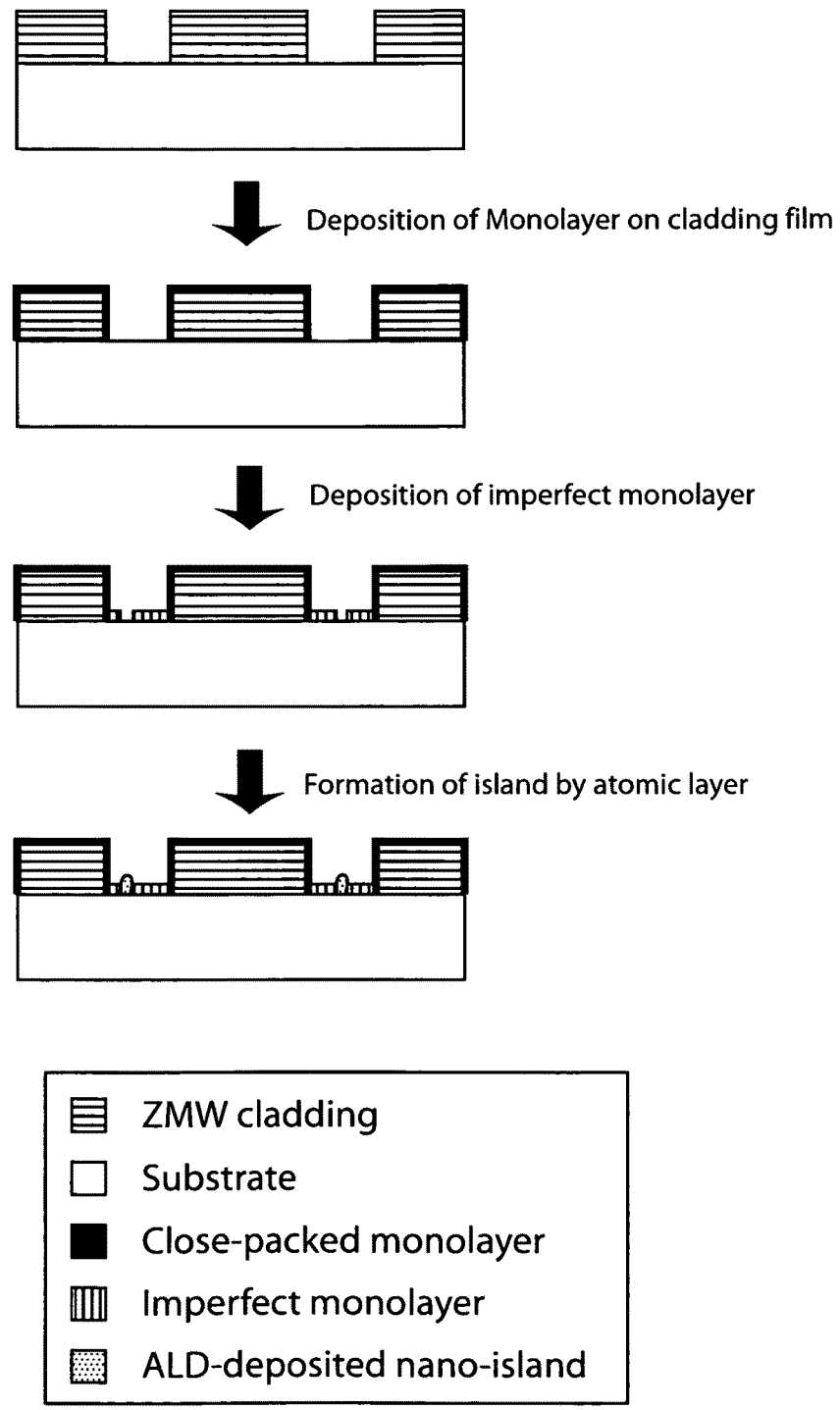
FIG. 9A provides a schematic illustration of a process flow for forming nanoparticles in ZMWs via deposition of an imperfect monolayer. A process flow for flat substrates is shown in FIG. 9B.
Figure 9B:
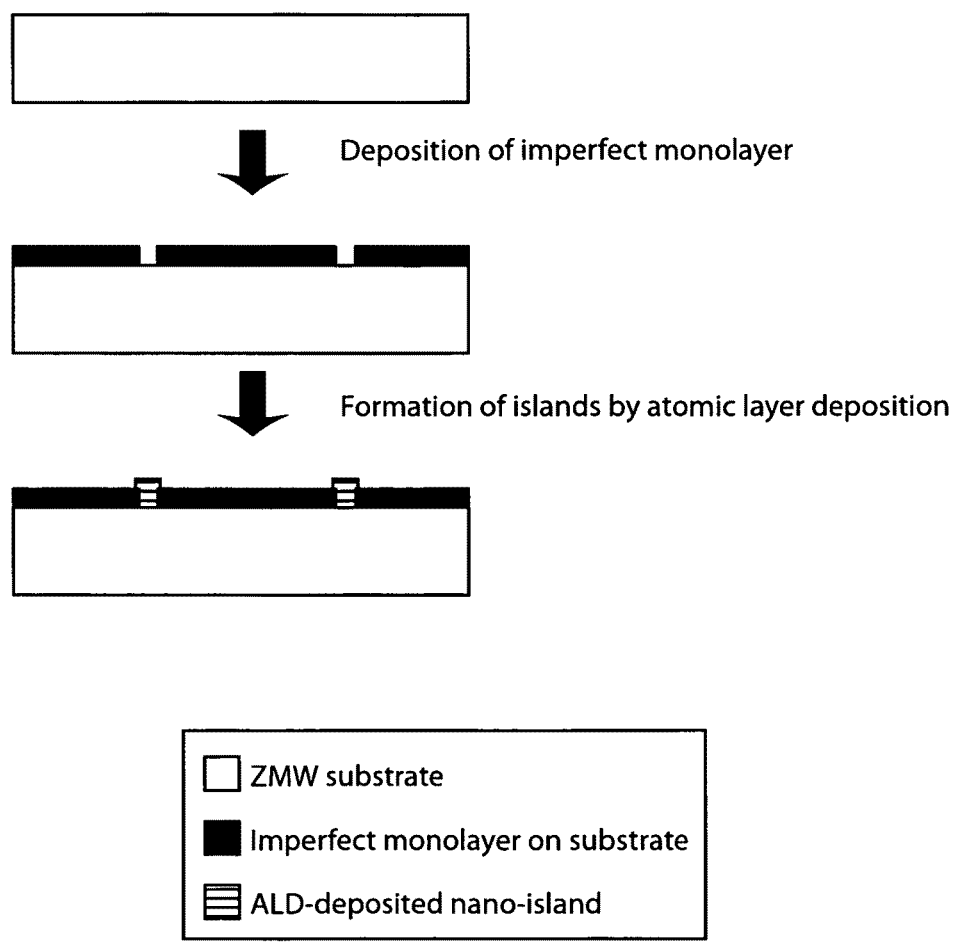

Depositing a Small Binding Site Island in a ZMW Using Self-Assembled Monolayers and Atomic Layer Deposition In this embodiment, to make islands sufficiently small so that only one polymerase can bind to one island, imperfectly-formed self-assembled monolayers and atomic layer deposition (ALD) are used. These technologies are routinely applied to form gate dielectrics of similar size for nanoscale electronics, demonstrating the feasibility of this method. As shown in FIG. 9A, the imperfect monolayer serves as a mask for forming an island on the surface by ALD. This island surface can be functionalized with linker to bind the desired enzyme, e.g., a polymerase. Unlike other types of deposition processes such as sputtering, evaporation, and conventional chemical vapor deposition (including but not limited to low-pressure chemical vapor deposition, high-density plasma chemical vapor deposition, plasma-enhanced chemical vapor deposition, etc.), ALD is sensitive to surface species, and films do not typically form unless those surface species are present to react with the ALD precursor and oxidizer. By selecting suitable monolayers for the cladding film and substrate, the ALD film grows only on the substrate. Deposition of materials that form imperfect monolayers such as octadecyltrichlorosilane is repeatable and controllable so that very small (<30 nm diameter) openings can be created, yielding an effective nano-mask for ALD. As above, this process can also be adopted to form small clusters sized for single polymerases on flat substrates. As above, these substrates can be used with single molecule techniques that do not require a ZMW structure such as TIRF. A process flow for flat substrates is shown in FIG. 9B.

Additional details regarding the production of imperfect monolayers can be found, e.g., in Richter et al. *Phys. Rev.* E, 2000, 61, 607-615. Further details regarding ALD can be found in Chen, et al., *Appl. Phys. Lett.,* 2004, 84, 4017-4019.

Depositing Small Binding Site Islands in a ZMW Using a Spacer Film

Figure 10A:
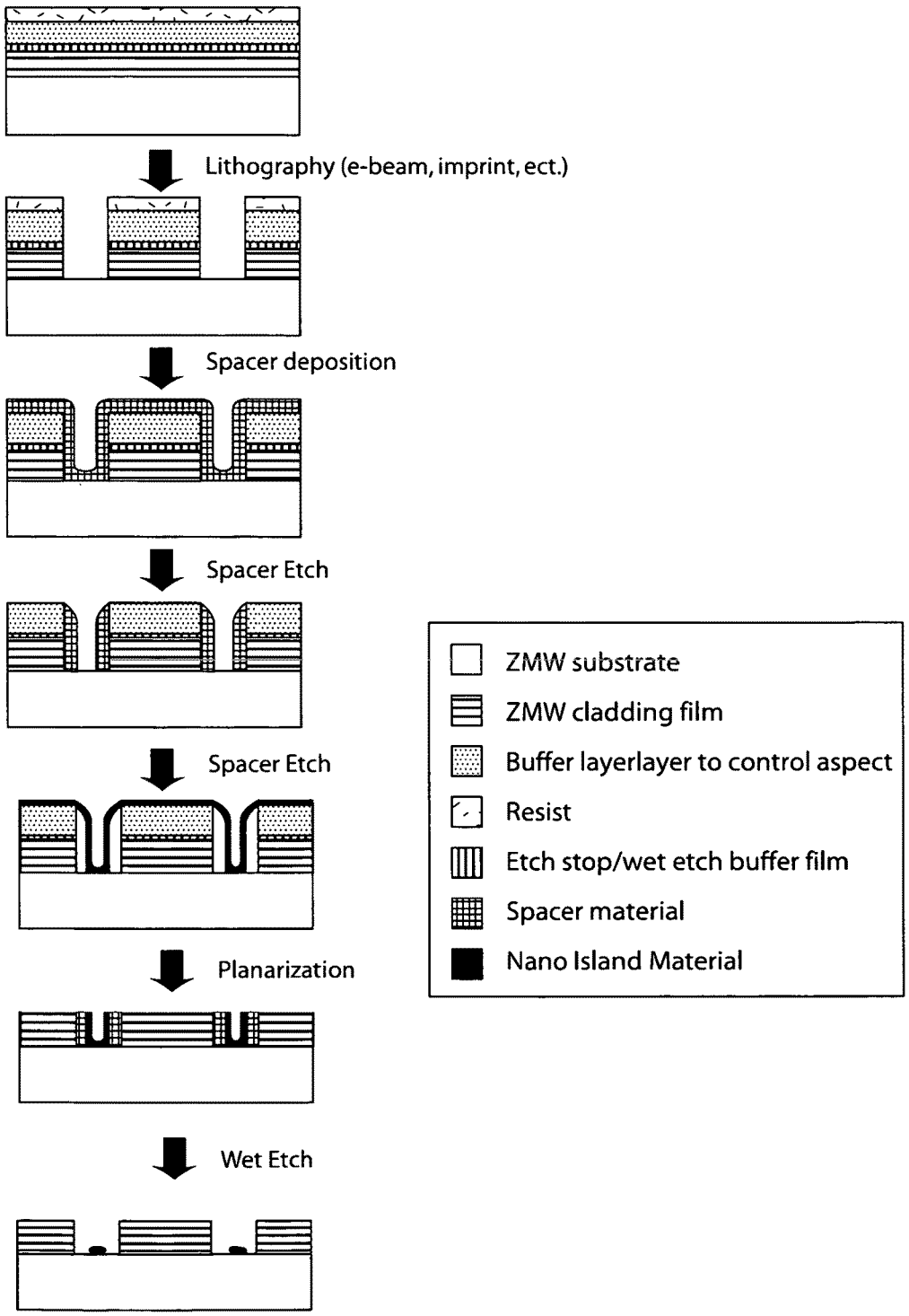
FIG. 10A provides a schematic illustration of a process for placing a functionalized island in a ZMW. A related process flow for flat substrates is shown in FIG. 10B.

In this embodiment, in order to make e.g., dots or islands, sufficiently small so that only one polymerase may be bound to one island or dot, a structure similar to that used for transistor spacer films is used as a self-aligning masking layer which controls both the location and size of the island or dot. As shown in FIG. 10A, a multi-film stack is created by exposing a positive-tone photoresist and etching through three layers. Alternatively, a positive-tone-like resist pattern can be created using nanoimprint lithography. The spacer film is deposited over the etched pattern by atomic layer deposition (ALD) or chemical vapor deposition (CVD). Using a directional etch, a spacer structure is created that forms isotropically around the ZMW hole, naturally aligning a space to deposit the island film in the center of the ZMW cavity. The island material is deposited by physical vapor deposition (PVD) or CVD. The entire stack is planarized to expose the buffer layer and spacer material so they can be removed by wet etching. A polish stop/wet etch barrier shown as the green film in FIG. 10A is present to protect the cladding film during these last two steps. Further details regarding techniques useful to this embodiment are found in Cerofolini, et al., (2005) *Microelectr. Eng.*, 81, 405.

Figure 10B:
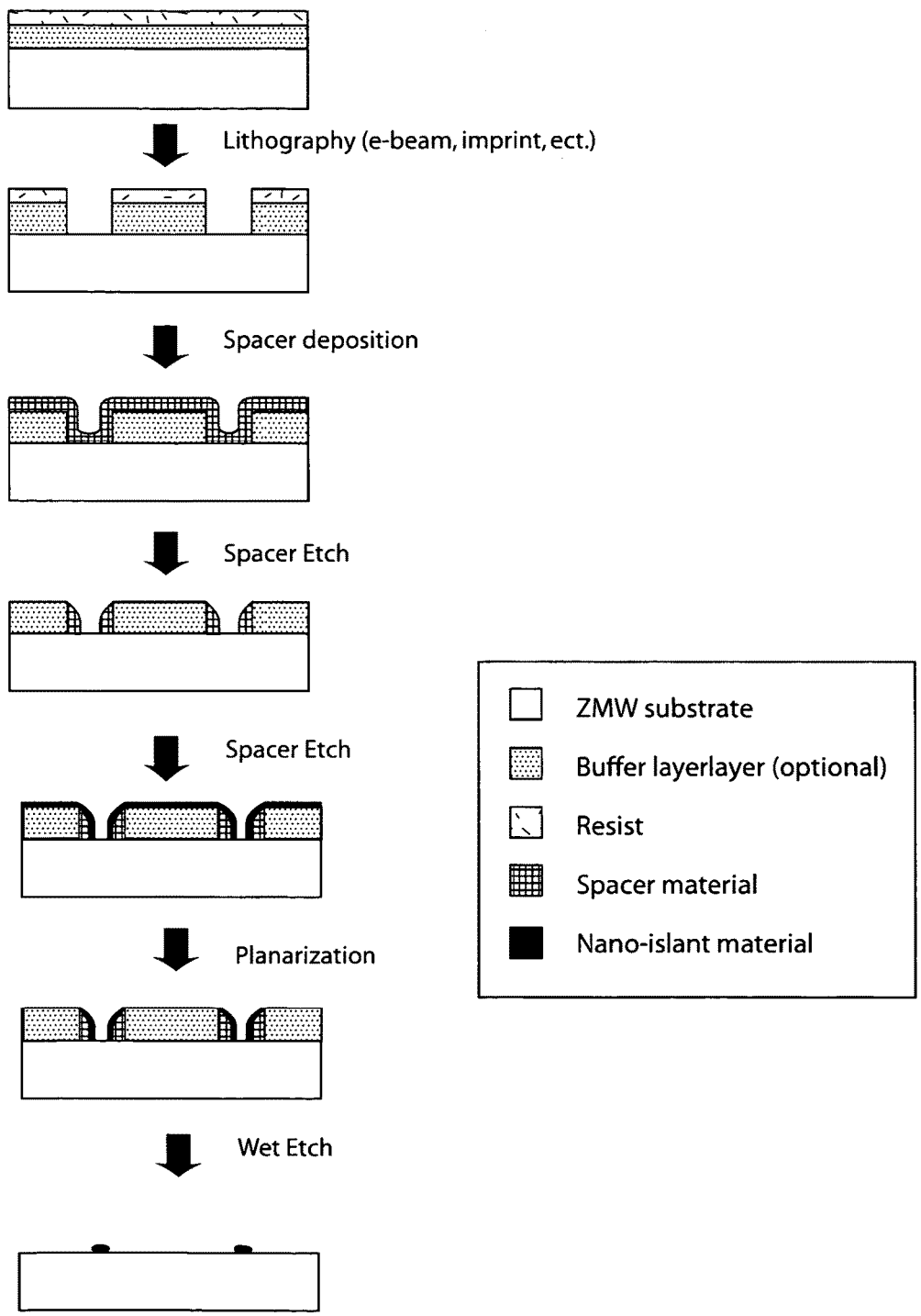

This process can also be adopted to form small islands that are sized for a single polymerase on flat substrates as well, e.g., using TIRF. A process flow for flat substrates is shown in FIG. 10B. In this case, if the resist is used alone or in conjunction with the buffer layer, then low-temperature ALD is suitable for depositing over the resist structures. The techniques illustrated by both FIGS. 10A and 10B produce an island surface that can be functionalized with a linker, e.g., that binds to polymerase.

Deposit Metal Nanoparticles in a ZMW Using Backside Exposure of Photoresist

Figure 11:
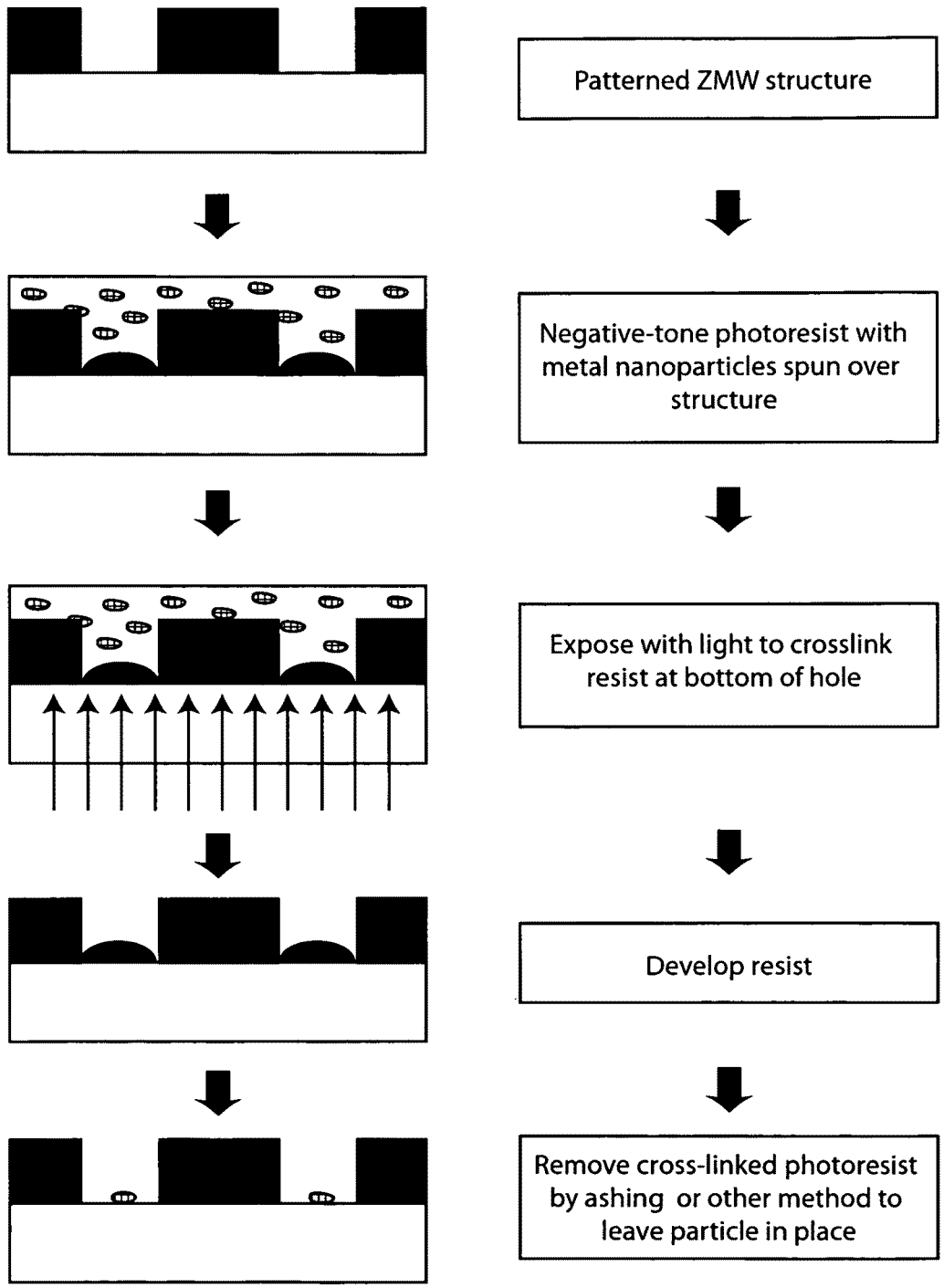
FIG. 11 shows a schematic process for immobilization of nanoparticles in ZMWs.

Immobilization of nanoparticles, e.g., metal nanoparticles can also be achieved by the process shown in FIG. 11. After the ZMW is fabricated using current processes, nanoparticles of sizes ranging from 10-100 nm are suspended in a negative-tone photoresist and spun onto the ZMW structure. The backside of the ZMW is exposed to radiation to cross-link the resist. The wavelength is chosen so that the illumination region is at the bottom of the ZMW hole. The un-crosslinked resist is removed as usual. The remaining photoresist is removed by ashing or other manner that leaves the nanoparticles in the ZMW hole.

Creating Particles in a Target Area by Annealing Smaller Nanoparticles

In one embodiment, monolayers of small nanoparticles close-packed on a surface can be annealed to coalesce and form a single, larger particle. The technique uses deposition of monolayers of small nanoparticles (e.g. 1.5 nm diameter particles) in a desired portion of an array (e.g., at the bottom of ZMWs of the array) followed by annealing the sample. The particles coalesce to form 1 or a few larger particles in the bottom of the ZMW, providing a limited number of binding sites for an analyte of interest. The size of the resultant particle is dependent on the composition of the nanoparticle monolayer, e.g., spacing, density, particle size, etc. These parameters can be adjusted so that the size of the particle only allows a single polymerase to fit on it.

Deposition of a Gold Particle in a ZMW Using Block Copolymer Micelle Nanolithography In one aspect, block copolymer micelle nanolithography is used to produce spatially well-defined deposits of nanometer-sized gold (or other nanomaterial) deposits that can be functionalized as phase determining features for binding of single analyte molecules. In this fabrication protocol, ZMWs (or other small array features) act as pre-structured guides for self-assembly of block copolymer micelles, generated at a size to match the ZMW (or other array feature) diameter. This results in one micelle per waveguide, and also results in positioning of an e.g., gold dot or cluster in the center of the waveguide. The clusters are stable and immobile, presenting suitable substrate sites for coupling to suitably tagged or derivatized molecules of interest, e.g., via gold-based or other suitable chemistries as described above. The small size of the dots/clusters (e.g., gold dots as small as 2 nm in diameter can be produced) ensures single molecule occupancy of the analyte in each ZMW (or other array feature), as proteins and other molecules are typically larger than the minimum size of the gold dots, and will be sterically prevented from binding more than one molecule of analyte per dot (e.g., T7 DNA polymerase has a ~10 nm diameter); thus, the binding site is sterically inaccessible to more analyte molecules after the first analyte has bound. This permits functionalization of a ZMW or other array reaction region under conditions of excess analyte (e.g., excess polymerase), ensuring that each ZMW or other array region harbors a single analyte molecule, followed by washing to remove unbound enzyme.

Additional details regarding functionalization schemes for gold dots prepared by block copolymer micelle nanolithography for binding of single proteins can be found, e.g., in Glass et al. (2003) "Block copolymer micelle nanolithography" *Nanotechnology* 14:1153-1160; Glass et al. (2003) "Micro-nanostructured interfaces fabricated by the use of inorganic block copolymer micellar monolayers as negative resist for electron-beam lithography" *Adv. Funct. Mat.* 13: 569-575; Haupt et al. (2003) "Nanoporous gold films created using templates formed from self-assembled structures of inorganic-block copolymer micelles" *Adv. Mater.* 15: 829-831; and Arnold et al. (2004) "Activation of integrin function by nanopatterned adhesive interfaces" *Chemphyschem.* 5:383-388.

Use of Degradable, Photopolymerizable, Cross-Linked Networks as a Delivery Vehicle for Loading Chemically Active nanostructures into Array Features In one embodiment, a cross-linked network comprised of a very low concentration of reactive, small (e.g., less than about 50 nm) nanostructures such as beads are bulk-polymerized in the presence of a photo-polymerizable monomer (e.g., a positive resist or a photo- or pH degradable network such as PLA or PGA) to form a bulk polymer that fills a ZMW or other array reaction region. This network can be degradable via exposure to UV or, e.g., 405 nm light at low intensities. Using shadow masking or photolithography, it is possible to spatially control the degradation profile via light exposure intensity and mask size above the ZMW. The surface chemistry and/or the network properties are designed such that the beads or other nanostructures are placed in the vicinity of the ZMW or other array reaction region, controlling where the structures are delivered by controlling the region of the array that is exposed to light.

This embodiment provides delivery of single nanostructures to the surface of a ZMW or other array reaction region without having to rely on diffusion of the nanostructures. The nanostructures used can include, but are not limited to, gold beads that facilitate thiol chemistry, —COOH or —NHS reactive beads that can be used for functionalization using EDC or amine specific chemistry, magnetic beads, etc. The nanostructures can be functionalized before or after degradation of the surrounding network. If functionalized before degradation, the functional groups may be degraded, but depending on the density of the functional group on the bead, this approach can still deliver a single functionalized bead into each ZMW that can be used to bind to an analyte of interest. As has been discussed in detail herein, placing a single analyte binding site into each reaction region (e.g.

ZMW) of an array, it is possible to more completely load the reaction regions of the array than can be achieved with random loading approaches. Overall, this embodiment helps locate beads toward the surface of ZMWs or other array features to prevent the need to rely on diffusion as a delivery mechanism for an analyte binding nanostructure.

Electrochemical Growth of a Nanostructured Polymerase Binding Site

In one class of embodiments, an electrical current is used to nucleate growth of a nanostructure that can be used to bind to an analyte of interest. In this embodiment, an electrode can be placed under the ZMW or other array, with a transparent conductive substrate in between the electrode and ZMW. A small amount of current flowing from the electrode nucleates the growth of a small nanostructure at the bottom of the ZMW. Once one such structure nucleates, it is far more likely for that structure to continue to grow in response to further current flow than for another nanostructure to nucleate. The current flow is turned off (stopping growth of the structure) while the structure is still small enough for only one polymerase or other analyte to fit on it. The nanostructure can be functionalized with the appropriate chemistry as described herein. When the polymerases or other nanostructure is loaded in at high concentration, only one polymerase can bind to the nanostructure within each ZMW.

Forming Single Analyte Binding Sites in an Array Feature

Similar to the approaches for putting a nanostructure into a ZMW (or other array feature) to facilitate super-Poisson loading of an analyte, the invention also provides approaches for locating binding groups that are capable of binding to, e.g., a single analyte into the array feature, without the use of a nanostructure to provide the binding site. In this class of embodiments, binding sites for analyte molecules are not necessarily located on a functionalized particle or other nanostructure, but can be formed directly on the array feature. For example, using this class of embodiments, it is possible to form a small functionalized region at the bottom of a ZMW that is capable of binding to an analyte molecule, e.g., where the functionalized region is small enough that only one analyte molecule can bind to the functionalized region at a time.

As with the methods above, placement of a single analyte binding site in the ZMW or other array reaction region makes it possible to completely load the array with the desired number of analyte molecules (polymerase, template, etc.), by introducing a high concentration of analyte to the array, and then washing any excess analyte from the array after binding to the analyte binding site. As with the other embodiments herein, this approach is particularly well suited to delivery of a single analyte molecule to each reaction region of an array, though it is possible to use similar approaches to place more than 1 analyte binding site in an array reaction region, if desired. For single molecule sequencing applications, it is generally desirable to use the methods of this class of embodiments for loading single analyte molecules into a ZMW or other array reaction region.

Figure 12:
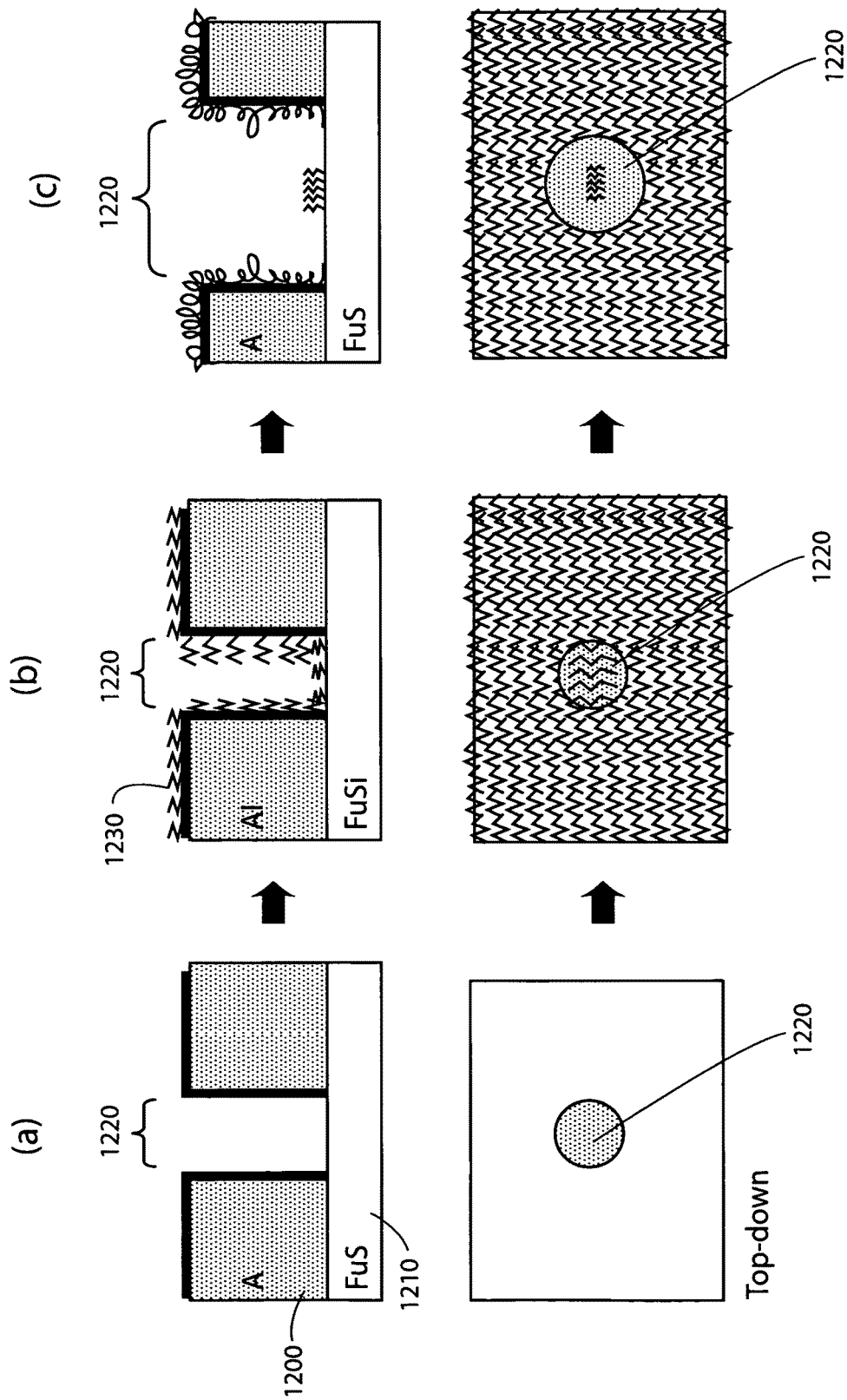
FIG. 12 shows an example schematic of a chemical polishing process used to form an analyte binding site at the bottom of a ZMW or other array reaction region.

Chemically Polishing a ZMW or Other Array Feature to Leave a Small Analyte Binding Site In one approach, chemical polishing is used to form an analyte binding site at the bottom of a ZMW or other array reaction region. FIG. 12, subpanel (a) shows an example schematic of the process. An initial array of reaction regions 1220 (e.g., ZMWs) or other array features is formed in cladding material 1200 (e.g., Al) on substrate 1210 (e.g., a glass, quartz or silicon substrate). The initial cladding is thicker than the final desired thickness of the cladding in a final array, and reaction regions 1220 (e.g., holes in the cladding), etc., have a diameter smaller than the final desired array region (e.g., the holes are smaller than the ZMWs that form a ZMW array).

The first step in the process, shown in FIG. 12 subpanel (b), is to deposit functionalizing material 1230 such as peg-silane (e.g. biotin-peg-silane) on the surface of substrate 1210, which is covered in cladding material 1200 (additional details regarding suitable linking chemistries is found herein). The functionalizing material deposits on the aluminum as well as on the glass or silicon surface at the bottom of holes 1220 in the cladding material, but is removed during chemical polishing.

The polish step is provided by an immersion of the functionalized cladded substrate into a phosphonic acid bath at elevated temperature (e.g. polyvinyl phosphonic acid at 90° C.). The acid uniformly etches (e.g., aluminum) cladding 1200. The surface at the bottom of the holes, e.g., glass, fused silicon, quartz, or the like, is not susceptible to corrosion in phosphonic acid. The resulting structure, shown in FIG. 12 subpanel (c), consists of a phosphonate treated ZMW (or other feature) array with a functionalized center having a larger diameter as the original hole through the cladding. By controlling initial cladding thickness, material, and hole-diameter, it is possible to yield a very small functionalized area in the center of the fused silica surface. The size of the functionalized region can be small enough that only a single appropriately functionalized analyte can bind to the small functionalized region. For example, if the analyte is on the order of 10-15 nm in diameter, the functionalized region can be on the order of, or less than, e.g., about 10-25 nm or less.

Such a surface is an ideal platform for achieving super-Poisson loading of a single active analyte (e.g., polymerase) in the bottom of an otherwise passivated ZMW. If the functionalized area is small enough, then only one, e.g., polymerase, is able to bind within each ZMW.

Deposition of a Small Analyte Binding Site in an Array Feature Such as a ZMW by Evaporation In one embodiment, an evaporation strategy is used to leave a functionalized region in the center of a ZMW or other array feature. The ZMW holes of the array are filled with one drop each of a solvent (water or other solvent appropriate to the functionalization chemistry) containing a low concentration of solute. The solute is a linker molecule capable of binding both the surface and the analyte (e.g., capable of binding to a DNA polymerase). As the drop evaporates from the outside to the center, the linker is concentrated in the middle of the ZMW or other array feature. Eventually the linker precipitates in the center of the ZMWs of the array. The linker can be chemically absorbed to the ZMW by heating, exposure to light, or any other appropriate linker fixation method. By optimizing the concentration of linker and solvent it is possible to form a very small region of the linker in the ZMW or other feature, e.g., small enough that only a single molecule of analyte can bind to the region.

The polymerase or other analyte is deposited into the ZMW or other array feature, e.g., by flowing the analyte onto the array. Free analyte is washed away, leaving an analyte bound to the center of the ZMW.

Tilted Angle Evaporation

Figure 13:
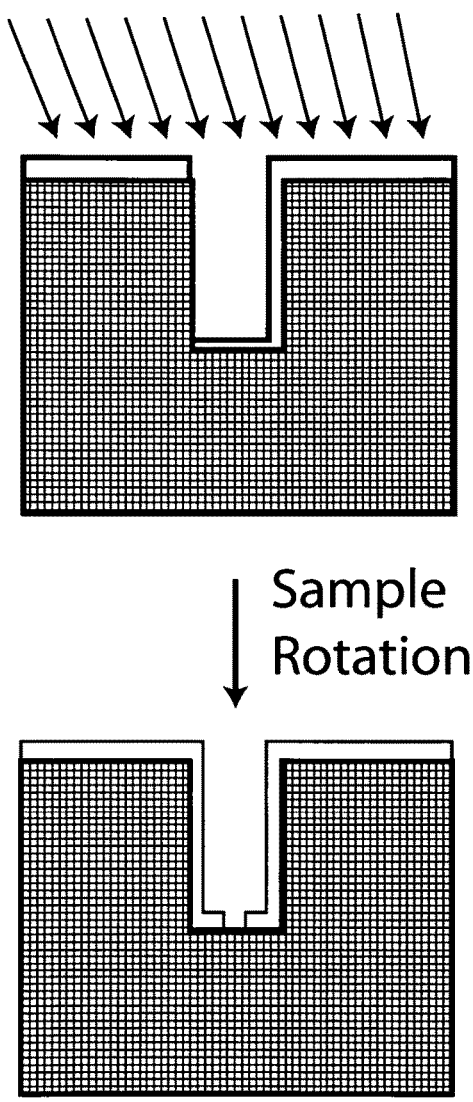
FIG. 13 provides a schematic of a tilted angle evaporation embodiment for forming a functionalized region in a center of a ZMW.

In a variant of the above method, tilted angle evaporation is used to mask off a portion of an array feature (e.g., to mask off a portion of a bottom surface of a ZMW), leaving a small unmasked region that can be functionalized for analyte binding. The resulting functionalized region can be small enough that only a single analyte can bind to the region. In this embodiment, evaporation of a coating is performed in the array feature (e.g., in the ZMWs of the array). If the sample is tilted in an evaporator, a portion of the bottom of the ZMW is left uncovered by the coating. If the sample is rotated during the evaporation (FIG. 13), it is possible to form an uncoated island in the center of the ZMW that does not contain the coating (this approach typically leaves the center of the bottom of the ZMW uncoated, which is desirable). A binding site for the analyte (e.g., polymerase) can then be added to the island. The binding site only attaches to the bottom of the ZMW or other array feature in the region of the uncoated island, i.e., the coating on the rest of the bottom blocks functionalization of the coated regions. The binding site can be small enough so that only a single polymerase or other analyte will easily bind to it.

Bead Assisted Conjugation of One (or a Few) Biotin-Peg Molecules to a Surface in a Self-Assembled Monolayer Super-Poisson loading of reaction regions (e.g., ZMWs) in an array can be achieved at high concentration of analyte (e.g., polymerase) if the (e.g., glass, quartz or fused silica) surface at the bottom of an array feature only contains one analyte binding molecule. As in the other embodiments herein, loading of the analyte can proceed to completion, because only one analyte will bind in each ZMW or other reaction region of interest.

To provide a single analyte binding site in the relevant array feature, a bead or other small structure roughly the size of the array feature (e.g., having a diameter close to the diameter of the ZMWs in a ZMW array) is used to react one array binding molecule such as biotin-PEG with the surface near a desired portion of the reaction region of the array (e.g., at the center of the bottom surface of ZMWs of the array).

Once this has been achieved, the array can be incubated with a high concentration of appropriately complementary analyte (e.g., a streptavidin-polymerase-template complex) to get close to complete loading with single, active analyte molecules (further details are found herein regarding pre-selecting polymerases for activity, which can be used to increase the active fraction of the analyte applied to the array).

Figure 14:
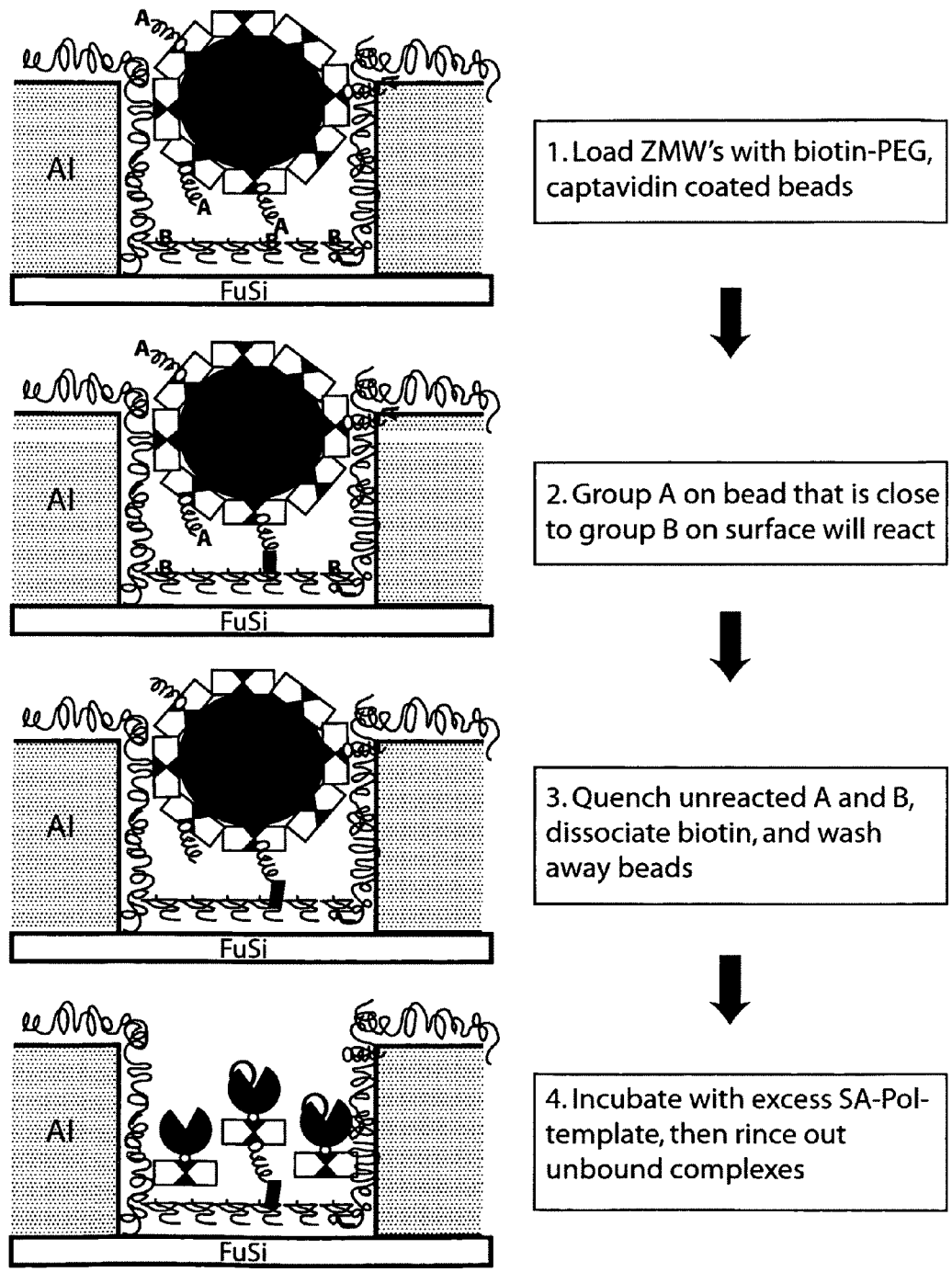
FIG. 14 provides a schematic illustration and flow chart of a process for bead assisted conjugation of one (or a few) biotin PEG molecules to a surface using a self assembling monolayer.

In one illustrative example described in FIG. 14, beads are coated with captavidin and bind to a biotin-PEG molecule containing a reactive functional group A at low surface coverage density on the bead. In one specific implementation, the molecule can be a biotin-PEG-hydrazine, e.g., as commercially available from Solulink (San Diego, Calif.). A ZMW array is incubated at a high bead concentration, so that almost all of the ZMWs of the array are loaded. By choosing a bead with a diameter close to that of a ZMW, only one bead can come in contact with the surface at the bottom of the ZMW hole (e.g., the glass or other similar surface). The hole bottom surface (which is typically glass, silicon, quartz, or the like) is functionalized with silane at a low surface density of functional group B that is reactive towards group A. Group B can be, e.g., a benzaldehyde moiety. The contact area between the bead and the surface constrains a biotin-PEG-hydrazine molecule to react with a nearby benzyladehyde group near the center of ZMW. As long as the surface density of the biotin-PEG-hydrazine and benzyladehyde groups is low, only one or few hydrazine group can react. Once reaction is complete, unreacted A and B sites are quenched, and the biotin-PEG is dissociated from the captavidin at high pH, releasing the bead, which can then be washed away. The ZMW chip can be incubated with a high concentration of streptavidin-polymerase to ensure that a maximum number of ZMWs are singly loaded.

In the embodiment above, biotin-PEG molecules can be replaced with other molecules (e.g., other PEG molecules) that are linked with a moiety that can bind or react with polymerase. Also, group A and B can be replaced with other chemistries that react together but do not react with polymerase.

Removing or Blocking Analyte Binding Sites After Binding of an Analyte

As discussed herein, simple loading and analysis of single analyte molecules into arrays of analysis regions, such as an array of ZMWs, can be constrained by the Poisson limit, which describes the statistical occupancy distribution of molecules in the array. For example, loading low numbers of enzymes, relative the number of, e.g., ZMWs in an array, yields a statistical distribution of enzymes in the arrays in which most ZMWs are either empty or singly loaded. If more enzyme is added, this decreases the number of empty ZMWs, creating more singly-loaded ZMWs, but also yields ZMWs with multiple enzymes. This causes difficulties in signal readout of what are intended to be "single" molecule reactions, such single molecule sequencing. For random loading, the optimum singly loaded occupancy distribution is limited by Poisson statistics, which typically means that about 70% of, e.g., ZMWs in an array do not generate useful data.

Creating arrays with one analyte molecule per reaction region can be approached in several different ways, as noted herein. As discussed, beating the Poisson limit, e.g., through steric or electrostatic means that facilitate single-loading of polymerases in the ZMWs, is highly useful in improving array efficiency. However, instead of using steric or electrostatic exclusion (or in addition to using steric or electrostatic exclusion), it is also possible to effectively remove binding sites after binding of a first analyte to the reaction region. This can be accomplished, e.g., by catalytically removing any unbound reaction sites after analyte binding, or by blocking the unbound sites, e.g., by coupling a polymer to the analyte that flattens out upon binding to the binding site, or by coupling the analyte to a multimer that binds to multiple binding sites.

Catalyst Scouring for Surface Patterning

Instead of using steric exclusion (or in addition to using steric exclusion), in one embodiment, tethered catalytic scouring of the surface is used to leave a desired number (e.g., one) analyte binding site in a region of interest (e.g., a ZMW, small well, reaction compartment, etc.). If the region only has one binding site, the analyte (e.g., polymerase, template, etc.) can be applied to the reaction region at high concentration, to ensure that the binding site binds to the analyte (excess analyte can be washed from the site, if desired). This approach does not have a particular format limitation. That is, catalyst scouring can be performed whether the reaction region is on a flat surface, in a ZMW, on a bead, or the like.

In one variant, a catalyst binding site within or proximal to a reaction region of interest is used to capture a catalyst, e.g., via a relatively long flexible tether or linker. Upon entry of the catalyst into the reaction region, and/or upon activation of the catalyst, the catalyst degrades any un-bound additional unprotected binding sites that it can reach. The catalyst is optionally blocked from degrading its own binding site, either through selection of a primary binding site/linker configuration that is not cleaved by the catalyst, or via steric inhibition by the linker, primary binding site, and/or catalyst. After the catalyst reaction is allowed to go to completion (once all secondary binding sites within reach of the catalyst have been degraded), the primary binding can be disrupted, allowing a secondary binding to occur between the primary binding site and a new moiety (analyte, etc.). Alternately, if the catalyst can only reach a portion of the reaction region, then those regions that are not reached can be sufficiently small that they include only selected number (e.g., 1) of analyte binding site(s).

Because e.g., a single secondary site is desirably left per reaction region, after treatment by the catalyst, the analyte can initially be applied to the reaction region at high concentration, while still resulting in one analyte being attached per area. Routine optimization for particular applications can include balancing the rate of primary catalyst binding with the rate of catalysis and with concentration and component diffusion rates. In addition, more than one catalyst-tether molecule can, in some circumstances, bind initially to the reaction region. If additional catalyst molecules binds to a cleaved secondary binding site, then the secondary catalyst increases the rate of removal of secondary binding sites. However, if it binds and blocks a secondary binding site, then more than one secondary binding site can be left behind after catalyst treatment. This can be addressed, e.g., by releasing the catalyst, binding a second round of catalyst to the site, and repeating the process, as necessary, until only one site is left in a region of interest.

A number of variants within this approach are possible. In a first variant, a catalyst binding site and a secondary binding site that is cleaved/destroyed by the catalyst can be different. For example, binding sites can incorporate different nuclease cleavage sites. Placement of the catalyst binding site relative to the secondary site can protect the secondary site, e.g., by steric interactions, reach of the tether, or the like. If the catalyst binding site is impervious to the catalyst, the catalyst can be retained until it is specifically released from the reaction region. The primary catalyst binding site that is left behind can also be re-used as an analyte binding site, e.g., where two different analytes are desirably present in a reaction of interest.

The flexible linker used to initially anchor the catalyst can be engineered to for ease of production, length of the linker (and reach of the catalyst) or the like. Where the catalyst is an enzyme, such as a nuclease, the linker can be, e.g., polyglycine, polyserine, a nucleic acid with a blocked nuclease site, or a combination thereof. This has the advantage of permitting simple recombinant production of the linker-enzyme as fusion protein, e.g., by encoding the linker with a catalysis domain. Polyethylene glycol (PEG) and other typical linkers can also be added via well-established chemical linkage methods.

A variety of different approaches can be used to release the catalyst or catalyst/linker. These include, e.g., heat, cleavage of a photocleavable site (e.g., in the linker, the catalyst, or at a site formed by the binding of the linker to the binding site), enzymatic cleavage of the linker (e.g., using a protease, or, where the linker is a nucleic acid, an endonuclease), or the like.

In one specific embodiment, a linker comprises or is connected to either the catalyst or binding site via a "SNAP™-tag" or similar linkage. This tag/linker is based on mammalian O6-alkylguanine-DNA-alkyltransferase (AGT). SNAP™-tag substrates are derivates of O6-benzylguanines. Related substrates, called "Clip-tags" (New England Biolabs) are benzyl-cytosine derivatives that are recognized by the same AGT proteins and or fusions. In the labeling/linking reaction, the benzyl group of the substrate/moiety that carries the label is covalently attached to the SNAP™-tag. SNAP™-tags are highly optimized for reactions with O6-benzyl guanines and related substrates. Cleavage of the catalyst can then be achieved by simple protease cleavage, e.g. using PreScission™ (GE Healthcare) protease. The primary binding element can include a blocker (such as backbone P→N substitution) after the benzylGuanine e.g., (bG-XXNXXXX). This has the effect of allowing the benzylGuanine (bG) to be cleaved, while allowing the catalyst to be released more easily.

For example, a reaction region surface can comprise bG. A low concentration of a catalyst fusion (e.g., Snap-(new tag)-long linker-enzyme) which binds to free bG is provided. The enzyme fusion can be incubated for a long time to ensure binding of one molecule per region. Because of the low concentration of the enzyme fusion, there is most likely only one binding event, with all other sites being modified by the activity of the enzyme. The enzyme is cleaved (e.g., via a cleavage site in the linker/Snap tag) to provide a new tag site, which binds to the analyte of interest (e.g., a recognition site for a polymerase).

Optionally, a catalyst can be optimized/engineered to reduce any inhibition caused by any particular tag. This can be performed via random or semi-directed mutation and screening methods such as DNA shuffling, or via any of a variety of routine directed or random mutagenesis protocols.

In an alternative, instead of a SNAP™ Tag linker/cleavage site, the catalyst is a single stranded endonuclease which degrades single stranded nucleic acids/oligonucleotides, e.g., fixed to the reaction region. The catalyst/linker comprises or is coupled to a site that binds to an oligonucleotide in the region, protecting that site. Other oligonucleotides in the region are degraded by the catalyst, removing them as potential binding sites. When heated, the catalyst is released, leaving behind a single oligonucleotide primary binding site, which is re-used to bind to an analyte of interest. One advantage of this alternative is that it can be performed cyclically/repeatedly to eliminate binding sites with repeated rounds of catalyst binding and activation. This alternative also allows for simple heating of the reaction region, e.g., using standard heat-cycling equipment (e.g., as designed for performing PCR), to remove polymerase or other analytes of interest after they are bound, making it possible to reuse the reaction region (e.g., to reuse a ZMW array, or other device).

In one useful embodiment, the catalyst contains a "kill" switch (triggered by heat, light, or other inactivation energy) which prevents it from removing any secondary binding elements when it is released from a primary binding site. For example, many catalysts, when heated, denature and are inactive (this is the case for most proteases and nucleases from organisms that are not thermostable). In some cases, this inactivation is not reversible. In either case, the catalyst can be released under conditions that reduce or eliminate activity of the catalyst, preventing it from scouring binding sites that are to be left behind for analyte binding.

Figure 18B:
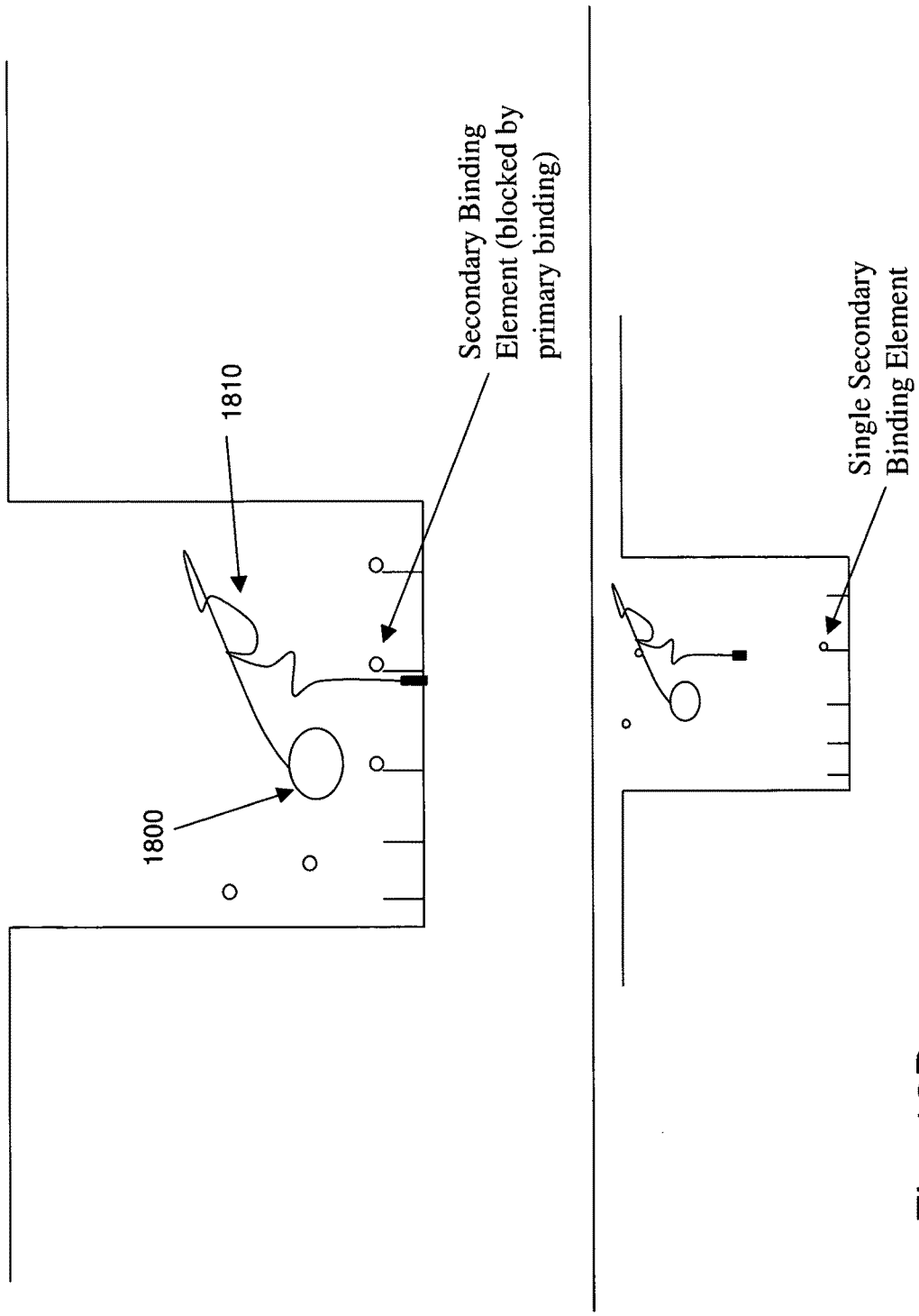
FIG. 18, panels A-C provide a schematic of a catalyst scouring technique to remove excess analyte binding sites in an array feature.
Figure 18C:
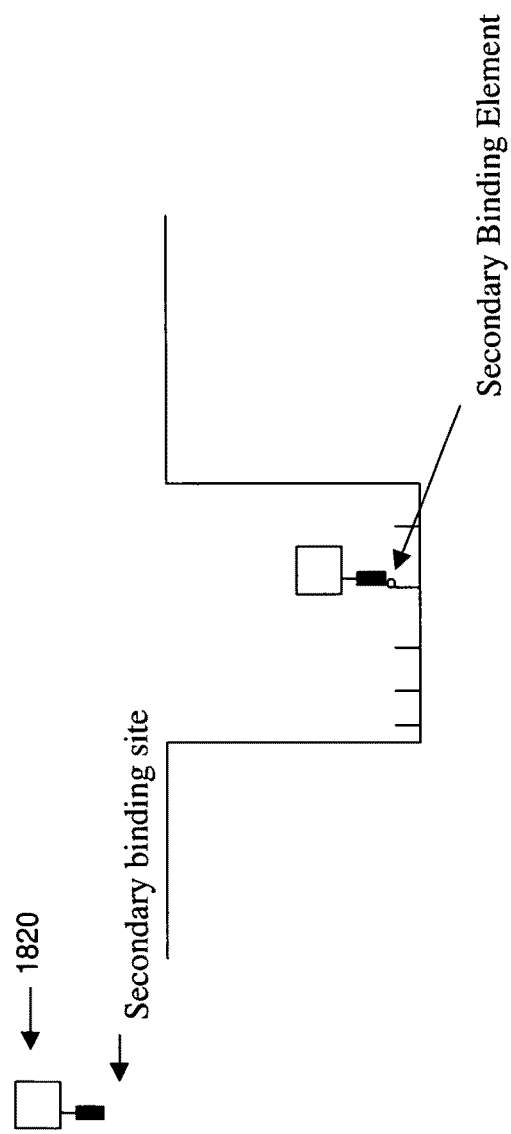

FIG. 18 further illustrates catalyst scouring approaches. As shown in Panel A, a primary binding element linked to surface scouring catalyst 1800 through flexible linker 1810 is bound, at low concentration to a surface to be modified, e.g., functionalized with a secondary binding element that binds to the primary binding element. As shown in Panel B, the catalyst cleaves the secondary binding elements from the surface, except for the secondary binding moiety that is bound by the primary binding element. The catalyst is then removed by treatment of the bound primary-secondary elements with an appropriate dissociation agent, e.g., heat, light, low salt, etc. The analyte, e.g., a moiety of interest such as polymerase 1820, which comprises an appropriate binding moiety is bound to the secondary binding element, or through a bi-functional linker bound to the binding element (Panel C).

As further illustrated in FIG. 19, catalyst 1900 can be, e.g., an exonuclease that degrades single stranded DNA. Primary binding site 1920 and linker can be, e.g., a single stranded DNA with a blocking group or P to N substitution that blocks degradation of the DNA by the catalyst. The analyte of interest can be, e.g., SNAP™-tagged polymerase 1930. Surface bound primary binding element 1930 can be a single stranded DNA that is complementary to primary binding site 1920, e.g., linked to the surface via standard silane chemistries. Secondary binding element 1940 can be, e.g., benzylguanine, which is recognized by the Snap tag on Snap tag polymerase 1930.

Figure 20A:
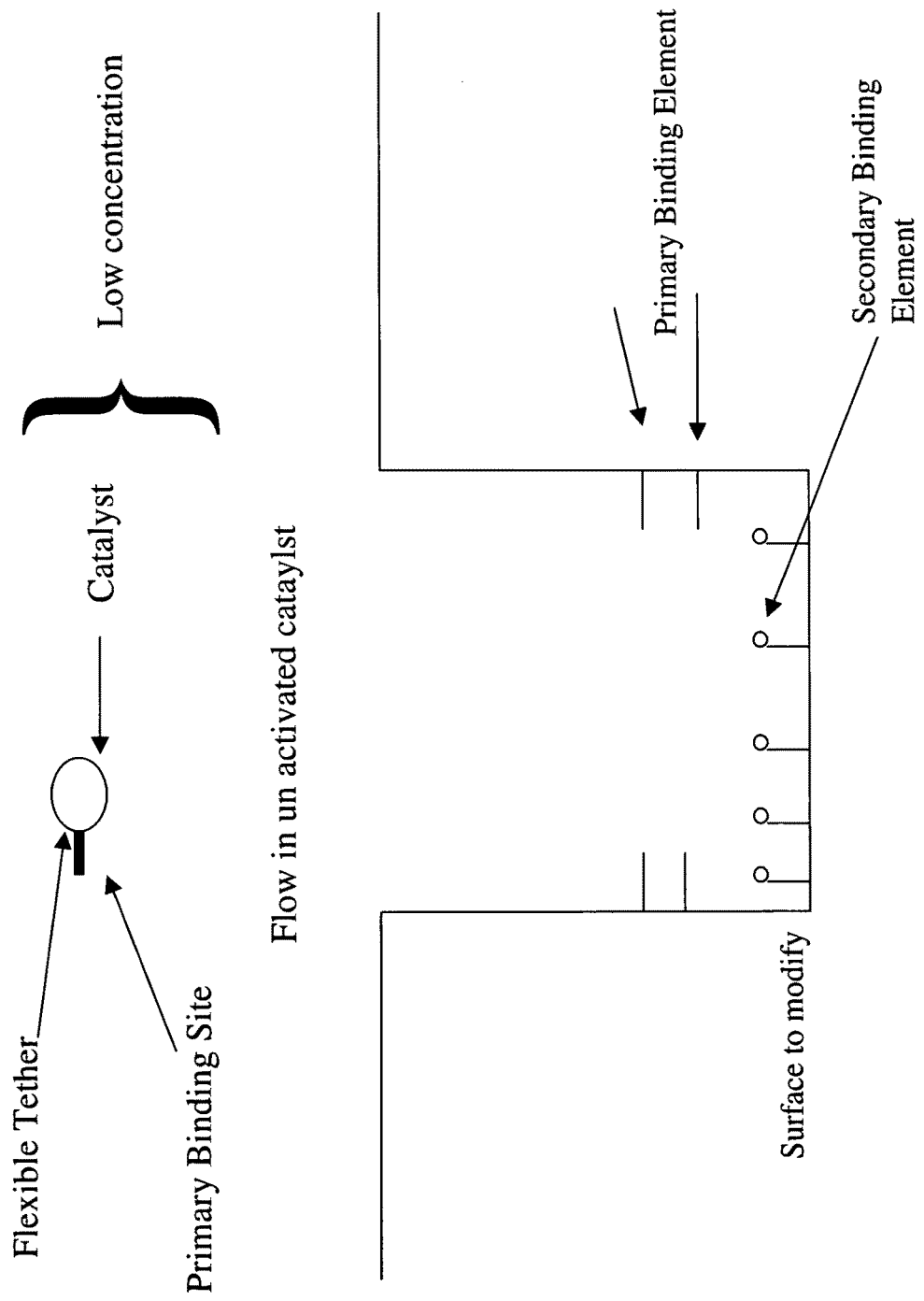
FIG. 20, panels A-B provide a schematic process for catalyst scouring that places the catalyst on the sides of an array feature of interest.
Figure 20B:
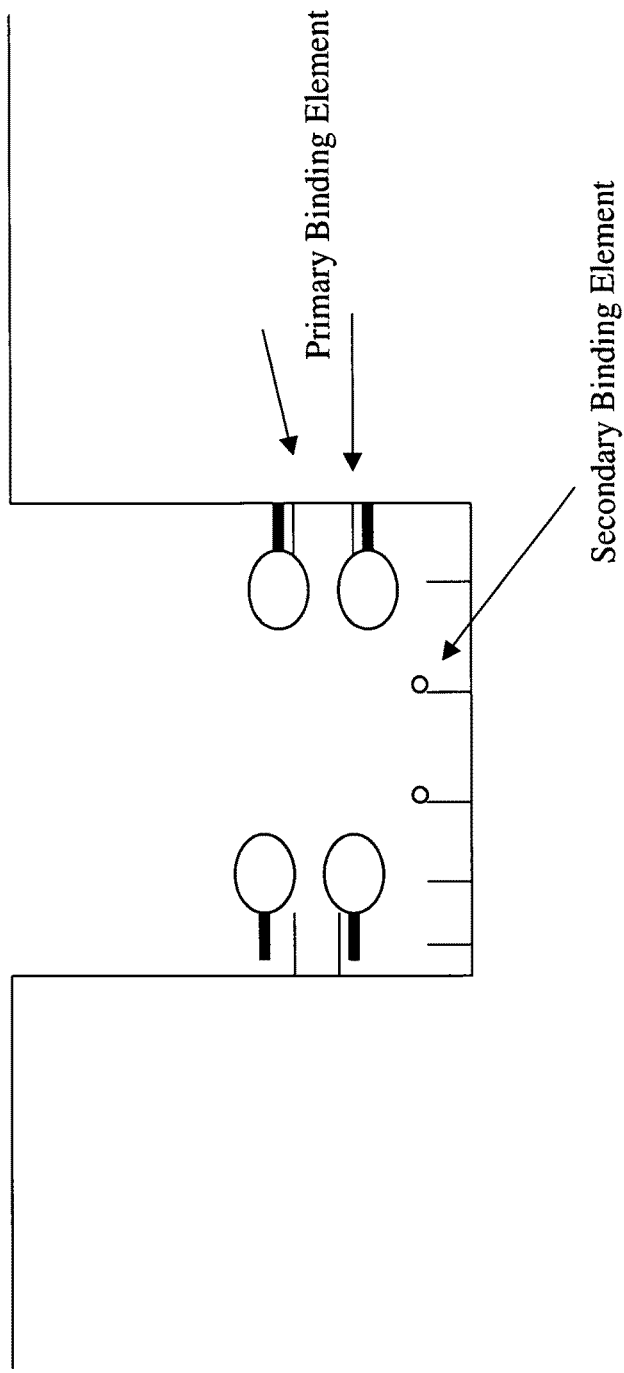

As shown in FIG. 20, panels A-B, in one class of variants, the catalyst is bound to the sides of the array feature of interest, via a flexible linker that is long enough to cleave binding sites from the edges of the feature, but not the center of the feature. At this point the catalyst can be added and activated or made less inhibited after binding to the primary binding element. Cleavage leaves one or more binding sites in the center of the feature (e.g., in the center bottom of a ZMW). If the center region that comprises binding sites is small enough, then only one analyte can bind to this region.

Figure 21:
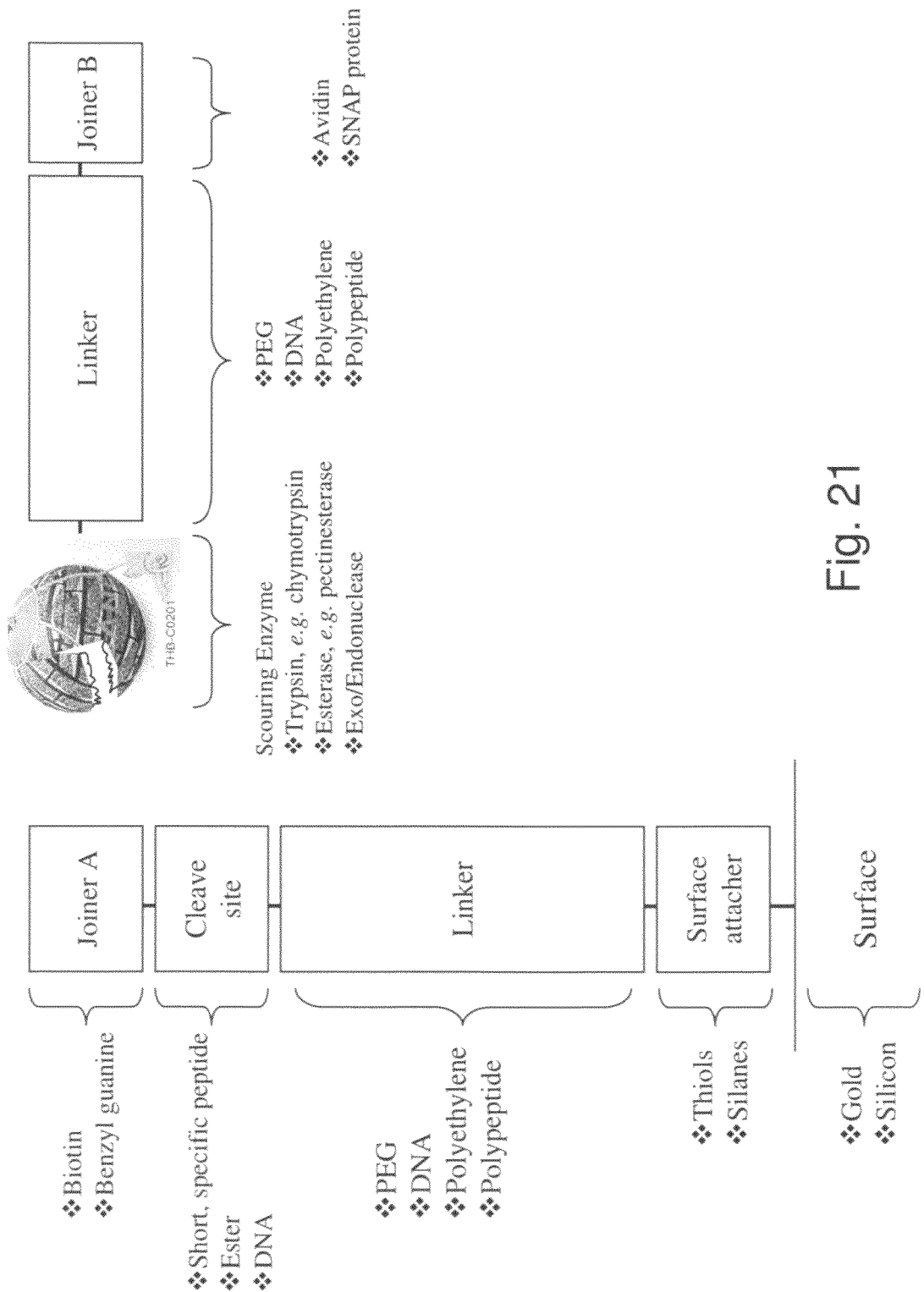
FIG. 21 provides additional details regarding example features of the moieties used for catalyst scouring.

Example variants of catalyst and surface binding features are schematically illustrated in FIG. 21. As shown, example catalysts include trypsin, esterase, exo or endonucleases; example surfaces with convenient linking chemistries include gold, and silicon; surface attachment chemistries include thiols and silanes; linkers include PEG, DNA, polyethylene, polypeptides and others; cleavage sites include peptide sequences, esters, and nucleic acids; attachment sites/joiners include biotin, avidin, benzyl guanine and SNAP™ proteins.

Particles of Polymerase and DNAase/Protease

In an example of the catalytic scouring approach noted above, the bottom of a ZMW or other region is made with numerous copies of a binding site, such as single-stranded DNA (which can be used to bind, e.g., either template or polymerase analytes, or complexes thereof). A fusion protein complex that includes a DNA polymerase, a complementary strand or strands of DNA that bind to the single stranded DNA, and a DNAase protein that degrades single-stranded DNA. When the complex enters the ZMW, the complementary DNA strand binds to one of the single-strands of DNA layering the ZMW bottom. The DNAase subsequently degrades any remaining single-strands of DNA, removing binding sites for additional complexes. See also, FIGS. 18-21.

In another example, the binding sites can be a protein (such as streptavidin). Instead of a complementary DNA strand, the complex contains one or more molecular groups that bind tightly to this protein (such as biotin). Instead of a DNAase, the complex would contain a protease that only degrades steptavidin that is not bound to biotin.

The components of the complex (polymerase, binding target, and DNAase/protease) can be produced as a fusion protein, or, in an alternate embodiment, can each be linked to linking structure such as a nanoparticle, rather than being produced as a fusion protein.

Use of Analyte Tails to Increase Loading Efficiency

In one class of embodiments, binding of a modified single polymerase or other analyte to a ZMW passivates that ZMW, in the sense that subsequent binding attempts by other polymerases/analytes are not successful. In one class of embodiments, the block produced by binding of the polymerase is removable or reversible, e.g., after the array has been filled with polymerases at each site where a polymerase is desired, to avoid hindering binding of other reaction components, such as templates, to the immobilized polymerases (or to a growing double-stranded reaction product if template is immobilized with the polymerase). One way of achieving these goals is to fuse a large polymer tail to the polymerase or other analyte, with a proteolytic cleavage site between the e.g., polymerase (and affinity tags used for immobilization) and the polymer tail. In solution, the polymer tail's shape can be described by a three-dimensional, self avoiding random walk, but near a surface, the polymer spreads out into a more two-dimensional "pancake" described by the 2-D random walk. This steric pancake passively terminates the ZMW surface, preventing loading of additional polymerases (or, optionally, other analytes). This approach to passivation of the ZMW or other reaction region is not limited to polymerases, in that similar approaches of using a large polymer tail can be incorporated with other analytes, such as other enzymes, nucleic acid templates, etc.

Suitable polymers include polysaccharides, large polypeptide domains, polyethylene glycol, and the like. Further details regarding fusions between large polypeptide domains and polymerases can be found in Hanzel et al. ACTIVE SURFACE COUPLED POLYMERASES, WO 2007/075987 and Hanzel et al. PROTEIN ENGINEERING STRATEGIES TO OPTIMIZE ACTIVITY OF SURFACE ATTACHED PROTEINS, WO 2007/075873).

Similarly, in an alternate embodiment, a bead can be bound to the polymerase or other analyte, where the bead fills the ZMW or other reaction region upon binding. One advantage of the polymer tail over a bead is that the bead typically has a fixed, relatively large size to block the ZMW (which can limit diffusion of the bead and any associated analytes in solution), whereas the 3-D to 2-D shape rearrangement of the polymer tail upon binding means that a polymer that is smaller in solution than the bead can be used, which results in faster diffusion (leading to faster surface binding). The polymer will spread out upon successful binding to a ZMW and can block the same surface area as a bead or other fixed size particle.

Beads or polymer tails can be removed, e.g., using sequence-specific proteases that cleave peptide bonds between amino acids (e.g., the TEV protease cuts the peptide sequence "ENLYFQG" between the Q and G). A wide variety of sequence specific proteases are known and find use with this aspect of the invention, to release the polymer tails. See, e.g., Barrett et al. (2003) *The Handbook of Proteolytic Enzymes,* 2nd ed. Academic Press, ISBN 0-12-079610-4; and Beynon (2001) *Proteolytic Enzymes: A Practical Approach,* 2nd ed. ISBN-10: 019963662. In general, a polymerase (or other enzyme of interest) can be expressed as a fusion protein that comprises the tail (or an attachment site for the tail) and the polymerase, separated by a specific proteolytic cleavage site. The fusion can also include an array binding feature fused to the polymerase, to facilitate binding of the polymerase to the array. A protease specific for the cleavage site is added to the array, after binding of the polymerase, to release the tail.

Pegylation

In one embodiment of this approach, the polymerase or other enzyme is pegylated using standard methods. In solution, the pegylated complex is roughly spherical, permitting it to easily enter an array feature (well, ZMW, etc.) that is large enough to accommodate the complex in solution. Once bound to a surface, e.g., using standard PEG linking chemistries, the PEG molecule will flatten out, and can block binding of additional analytes to a surface that the PEG is attached to, e.g., where the PEG covers the surface.

Attach Polymerase to Biotin Dendrimer

In one variant, rather than catalytically removing excess binding sites, the excess binding sites are bound or rendered inaccessible by analyte binding. This can be accomplished by adding a binding structure to the analyte that comprises several binding elements that bind to several or all of the available binding sites in a given array region (e.g., the binding sites in the bottom of a given ZMW). A variety of molecules can be used for this purpose, including branched molecules such as branched DNA (bDNA), self-assembling multimers, dendrimers, dendrions, branched polymers, fusion proteins, and the like; long linear molecules with multiple available sites can also be used, e.g., where the linear molecules are flexible and can bind to multiple sites at once.

Dendrimers and dendrons, for example, are large molecules (5-25 nm) that can be tailored to have multiple terminal groups with the same functional moiety. In this variant, a dendrimer is made with, e.g., both biotin and benzylguanine termination groups (other type of binding groups can be used as well, depending on the binding site to be bound). This dendrimer is hydrophilic, and is able to carry, e.g., 10+ biotin end groups; the branch to which the benzylguanine (which is used in this non-limiting illustrative example to bind to the analyte) is attached is long and flexible so that the biotin branches can cover a large area.

This dendrimer is bound to a SNAP™-tagged polymerase; if desired, the reaction mix can be purified through size-exclusion to provide only a mono-loaded polymerase dendrimer. A dilute biotin coated surface is provided in the array (e.g., at the bottom of ZMW holes), with the total number of available biotins per array being ~10, achieved through dilution of the biotin moiety during the surface preparation. The surface is coated with streptavidin, which binds the polymerase-dendrimer to the surface. Once the first biotin-streptavidin binding occurs at the surface, other biotins groups on the dendrimer quickly bind to the remaining streptavidin molecules on the surface due to the entropy advantage provided by locating the dendrimer close to the surface. This depletes the streptavidin at the surface, preventing other polymer-dendrimers from loading.

Controllably Loading Individual Analytes

One aspect of the invention is the controllable delivery of individual analyte molecules to an array site (e.g., reaction or observation region, e.g., ZMW) of interest. This can be achieved, e.g., by optical or electrical trapping, by microfluidic flow control of solutions comprising the analytes, by photo-activation, or a combination thereof.

Super-Poisson Loading of Polymerase in ZMW Array Using an Optical or Electrical Trap, or an Array of Optical or Electric Traps One aspect of the invention provides for serial loading of a ZMW or other reaction region array with single polymerase/DNA complexes, using an optical or electric trap or trap array.

Using current technology, it is possible to capture a single latex (or other dielectric) particle in an optical trap (*Annual Review of Biophysics and Biomolecular Structure*. 23:247-285, 1994), where gradient optical forces on the dielectric particle trap the particle near the focus of, e.g., a laser beam. It is also possible to trap smaller particles, such as a polymerase/DNA complex, in an electric trap (e.g., an anti-Brownian electrophoretic, or "ABEL" trap, see *Appl. Phys. Lett.* 86: 093109 (2005)), without using a latex particle. It is also possible to create an array of optical traps, or an array of electric traps.

It is possible to link the analyte or analyte complex (e.g., polymerase or polymerase template compex) to a dielectric (e.g., latex) particle and capture it in an optical trap. The trap can then be positioned above a ZMW or other reaction region, with the complex being positioned inside the reaction region. When the trap is turned off, the complex can attach itself to the bottom of the ZMW or other region using appropriate chemistry (e.g., through a binding group on the particle or analyte complex that recognizes a cognate group attached to the reaction region). Optionally, the particle can be cleaved and released after delivering a single analyte to the reaction region. This process can be repeated for each reaction region, one-after-another, or an array of traps can provide simultaneous delivery of more than one particle or particle complex to the reaction region.

When using an array of optical or electric traps, a trap-to-trap pitch that matches the pitch (or other phase determining feature) of the ZMWs or array feature of interest is used. Each trap in the trap array contains a single analyte, e.g., polymerase or polymerase/dielectric particle complex. The array of traps is positioned within the array of, e.g., ZMWs, and is then released, e.g., in parallel. Once all ZMWs are loaded with one complex, the dielectric particle is cleaved using appropriate chemistries.

Alternatively, it is possible to capture the polymerase/DNA complex in an electric trap (also called an anti-Brownian electrophoretic trap, or "ABEL"), which is able to capture very small particles, and again position and release the complex in a single reaction region (e.g., ZMW).

Where an array of optical or electrical traps is used, the array can include a trap-to-trap pitch (spacing or format) that matches the pitch of the ZMWs or other reaction regions on or in an array of analysis regions/ZMWs. Each trap can contain a single latex particle and/or analyte and/or analyte complex (e.g., polymerase/DNA complex); these complexes are positioned appropriately relative to the reaction regions of the array (e.g., ZMWs in a ZMW array) and released in sequence or in parallel.

A variety of alternatives are readily appreciated for this set of embodiments. For example, the size and composition the particle can vary, e.g., the particle can include latex, silica, magnetic or non-magnetic metal, polystyrene, etc. The laser used for the optical trap can vary depending on the nature (size and composition) of the particle. The size and format (e.g., pitch) of the optical or electric trap array is selected for ease of use with the array of reaction regions. Methods used to position the traps can vary, depending on available equipment for orienting, focusing and moving trap components. Chemical subgroups on analyte components can vary depending, e.g., on the attachment chemistry to be used between the particle and the analyte (e.g., between the components of a polymerase/DNA/particle complex, e.g., it is possible to add or remove charged groups or affinity groups to provide for charge or affinity interactions).

Super-Poisson Loading of Polymerases and Other Analytes Using Microfluidic Channels In one aspect of the invention, single molecule analytes, such as polymerases or templates, are controllably delivered to a reaction site of interest (e.g., a ZMW) via a microfluidic delivery system. Because delivery is controllable, all of the reaction sites of interest in an array can be loaded with a single analyte molecule (or as many analytes or molecules as is desired). This controllable loading approach overcomes the Poisson limit that can be achieved by random loading of single molecule analytes.

For example, a microfluidic device can be coupled to a ZMW or other reaction region array such that each ZMW or region is independently addressed by at least one microfluidic channel. Each channel can include a valve or flow gating system enabling it to be controlled (opened or closed) independently. A very low concentration of polymerase, template, or any other analyte, e.g., labeled with a fluorescent tag, can be flowed into each channel. The ZMW or other reaction region can be, e.g., optically monitored, e.g., using a CCD camera. When an appropriate signal (e.g., a flash of fluorescence) is seen in a ZMW or other reaction region, this is an indication that a labeled analyte has entered that ZMW. The valve or other gating device regulating flow to that ZMW is closed before another relevant analyte can enter. This process can be continued until all the reaction regions are loaded with a single molecule of analyte.

If desired, the fluorescent or other label can be cleaved from the analyte after loading—in serial or in parallel—using appropriate chemistry. Cleavage of the label is especially desirable where the label will interfere with downstream use of the analyte, e.g., in a sequencing or other reaction.

It will be understood that the type of label used to detect presence of the analyte can vary. For example, the label can be non-fluorescent/fluorogenic, e.g., the label could be a magnetic label, a light scattering label, a surface-enhanced Raman scattering label, or the like. Appropriate detectors will be configured to detect the relevant label. For example, in one embodiment that does not rely on fluorescence, instead of tagging the polymerase with a fluorescent label, it is possible to monitor conductivity through a narrow region of the microfluidic channel. When a polymerase or other analyte passes through the neck, there is a drop in the conductivity, which can be monitored with a conductivity sensor. When a drop in conductivity is measured, a valve can be closed, or flow can otherwise be gated to prevent another polymerase from entering the array region.

A variety of microfluidic systems can be used for analyte delivery to reaction regions such as ZMWs. These include systems that move analyte-containing fluids using pressure-based flow, electrokinetic flow, or the like. For an introduction to microfluidic and other related systems, See, e.g., Bruus (2007) *Theoretical Microfluidics* (*Oxford Master Series in Physics*) ISBN-10: 0199235090; Li (2006) *Microfluidic Lab-on-a-Chip for Chemical and Biological Analysis and Discovery* (*Chromatographic Science*) CRC ISBN-10: 1574445723; Tabeling (2006) *Introduction to Microfluidics* Oxford University Press, USA ISBN-10: 0198568649; Nguyen and Wereley (2006) *Fundamentals And Applications of Microfluidics, Second Edition* (*Integrated Microsystems*) Artech House Publishers ISBN-10: 1580539726; Saliterman (2006) *Fundamentals of BioMEMS and Medical Microdevices* (*SPIE Press Monograph Vol. PM*153) PIE Publications ISBN-10: 0819459771; Berthier and Silberzan (2005) *Microfluidics for Biotechnology* (*Microelectromechanical Systems*) Artech House Publishers ISBN-10: 1580539610; and Karniadakis et al. (2005) *Microflows and Nanoflows: Fundamentals and Simulation* (*Interdisciplinary Applied Mathematics*) Springer ISBN-10: 0387221972; Minteer (Editor) (2005) *Microfluidic Techniques: Reviews And Protocols* (*Methods in Molecular Biology*) Humana Press, ISBN-10: 1588295176. A wide variety of microfluidic delivery and control systems and devices are described in the literature, and various commercial sources provide "off the shelf" microfluidic controllers and apparatus, including those available from Caliper Life Sciences (Hopkinton, Mass.) and Fluidigm Corp. (South San Francisco, Calif.). These include systems that use electrokinetic and pressure based controllers, as well as electrokinetic gating, membrane valves (e.g., Nanoflex™ valves), and the like. Such systems can be adapted to deliver materials to a ZMW array via microfluidic channels.

Super-Poisson Loading by Active Photo-Activation Immobilization Control

Random analyte loading methods to distribute single analyte molecules into an array of reaction sites yields a statistical distribution of analytes in the reaction sites that is generally well described by Poisson statistics. These approaches yield a maximum single molecule occupancy in such arrays of about 37% (higher levels of loading result in two or more molecules per site, confounding single molecule analysis); in practice, this theoretical maximum is relatively high, with loading efficiency of about 30% being more typical. The methods, compositions, devices and systems herein provide much higher single molecule occupancy loading of analytes, increasing the throughput of single molecule sequencing protocols.

In one class of embodiments, loading is actively controlled by selective photo-activation of analytes and arrays. In certain of these methods, both a detectable label and a photo-activation group is incorporated into the analyte (e.g., into a polymerase). The array or reaction regions (e.g., ZMW array) is illuminated by light sources to (1) activate the photo-activation group, which renders the polymerase capable for binding to the ZMW surface, and (2) to detect or track the analyte by detection of the detectable label. The label and the photo-activation group can use the same light source, or separate sources. Upon detection of immobilization to an array site, at least the light source that provides photoactivation is turned off, or otherwise blocked from the array site, eliminating binding of additional analyte molecules to the array site. This process can be repeated at all desired array sites, resulting in up to 100% loading of the array (lower levels of loading, e.g., greater than, e.g., about 40%, about 50%, about 60%, about 70%, about 80%, about 90%, etc. can also be achieved by this approach).

It will be appreciated that a number of variants of this approach are specifically contemplated. For example, in a highly multiplexed reaction site array, each site in the array (e.g., each ZMW in a ZMW array) is typically addressable individually (because the arrays are configured for detection of separate reaction events at the sites of the array). Thus, the cessation of illumination to individual sites can be controlled automatically, e.g. by use of micromirror plates or other optical elements that can be used to control light delivery to an array site of interest (e.g., use of waveguides, optical trains, etc.). The light sources for photo-activation and labeling can be the same, or separate sources (e.g., providing different wavelengths of light) can be used. Other variants include the optional use of a sacrificial polypeptide or other molecule attached to the analyte to carry either the photo-activation group or the label. Label detection can include optical detection, fluorescence detection, light scattering detection, or any other available label detection method. Further details regarding optical array systems that find use with the invention can be found, e.g., in Lundquist et al., PCT/US2008/010652 HIGHLY MULTIPLEXED CONFOCAL DETECTION SYSTEMS AND METHODS OF USING SAME; and Lundquist et al., PCT/US2008/005953 METHODS AND SYSTEMS FOR ANALYZING FLUORESCENT MATERIALS WITH REDUCED AUTOFLUORESCENCE; and Korlach et al. WO 2008/121374 SYSTEMS AND METHODS FOR ENHANCING FLUORESCENT SIGNALS.

Iterative Analyte Loading

In one class of embodiments, high densities of single molecule analytes in array reaction regions such as ZMWs of a ZMW array are achieved through iterative loading procedures. In general, these procedures include performing a first loading cycle, e.g., using standard random analyte loading methods, followed by a subsequent loading cycle that targets regions of the array that were not loaded in the first loading cycle. These iterative loading procedures can be repeated until essentially complete single molecule loading into all desired array regions is achieved.

In general, after each loading cycle, the presence of the analyte of interest is detected, e.g., through an activity assay (e.g., by detecting a SMS sequencing reaction), or via detection of a label bound to the analyte. Regions that do not comprise the analyte are targeted for additional loading, e.g., by directing flow to those regions (e.g., using microfluidic flow or optical or electrical trapping as described herein), or simply by masking the loaded regions and loading unmasked regions.

For example, random loading methods that result in a standard statistical distribution of analytes into array regions can be performed. For example, polymerase loading can be performed, using a fluorescently labeled polymerase (or using any other type of detectable label). After deposition, the array is imaged (the labels are detected) to detect which array regions (e.g., which ZMWs) contain only one polymerase (single versus multiple loading can be differentiated by the magnitude of the label signal at each array site). A mask is created, e.g., using lithographic methods as discussed herein, with the mask protecting those array regions (e.g., ZMWs) that contain only one polymerase. The remaining ZMWs are washed out to remove polymerases from multiply-loaded ZMWs. This process can be repeated until essentially all of the array regions are loaded with analyte. For example, after two rounds, ~60% of ZMWs can contain only one polymerase (if loading proceeds using standard Poisson statistics, about 0.37+0.37*0.63). After three rounds, ~75% of ZMWs will contain only one polymerase. After four rounds, ~84%. After five rounds, ~90%. After six rounds, ~94% loading is achieved. If desired, the label can be cleaved from the polymerase before starting a sequencing or other reaction.

Alternatively, each step could utilize sub-Poisson loading (e.g., below the ~37% Poisson limit) to ensure that there are virtually no multiply-loaded ZMWs in each reaction cycle. In this case, it is not necessary to differentiate between singly and doubly loaded array regions—instead, all of the labeled reaction sites can be masked, and the loading process repeated on unlabeled sites.

Enrichment of Active Analytes

Typical analyte samples contain active and inactive forms of the analyte. For example, a typical solution of polymerase enzyme contains many copies of active and inactive molecules of polymerase. In bulk solution assays, where there are many copies of the analyte that can act in the reaction, this is not generally a significant issue—at most, it may be useful to normalize the activity of the analyte for quantitative purposes. However, in single molecule assays, the presence of a fraction of inactive molecules in a source of analyte molecules that is used to form single molecule reactions is undesirable, because the presence of an inactive analyte molecule in a given single molecule reaction effectively kills that reaction.

Thus, it is desirable to have a source of analytes that is enriched in active analyte molecules. For example, it is useful to form single molecule sequencing reactions using an enriched population of polymerases that is, e.g., capable of DNA extension so that all polymerase molecules immobilized in a SMS reaction are functional. Improperly active analytes such as some defective polymerases can also have undesirable features beyond simple inactivity, e.g., increased binding of labeled analogs, which can confound readout of SMS reactions; accordingly, it is also useful to actively eliminate improperly active as well as inactive analytes.

In general, any of a variety of screening steps to negatively select improperly active analytes, combined with positive screening steps to isolate active enzymes can be used to achieve active analyte enrichment. For example, polymerases that bind, but do not release a template can be negatively selected, while polymerases that bind and extend a template can be selected for. Polymerases that do not bind template at all can be negatively selected. Centrifugation, or simple size or affinity purification to isolate template bound from non-template bound fractions can be used to purify active enzyme from inactive enzyme. Similar approaches can be used to select for or against template nucleic acids to be sequenced, e.g., by separating cross-linked from non-crosslinked nucleic acids, or the like.

In one example, the invention provides a protocol to enrich fraction of active polymerase (e.g., Phi29 polymerase) in a given sample. The polymerase sample is first incubated with a "double headed template" with a FAM or hapten conjugated at 5' ends of oligos. Concentration of polymerase and template is to be at least about 10× Kd of the template-Pol dissociation constant, with polymerase at slight excess to ensure close to 100% binding of template. Functional polymerase molecules bind template, but non-functional, inactive polymerase or contaminating proteins do not. Bead conjugated to FAM antibody (or another antibody that binds to the hapten) is mixed and centrifuged, and supernatant is discarded to remove non-functional (non-template binding) proteins. The bead is resuspended and reagents for DNA extension are added (divalent metal. dATP, dCTP, dGTP, dTTP) along with a trap molecule, either DNA or heparin, at a concentration that is several times in excess of the double-headed templates. The reaction is allowed to proceed for a few minutes to allow the polymerase to extend the DNA. Active, productive polymerase catalyzes dNTP incorporation and extends the DNA and eventually dissociates from the template when it reaches the end of the (linear) double headed template. These active polymerase bind the trap molecule and do not rebind to any free "double head template". Non-productive or non-catalyzing polymerase remains bound to the template. Active, productive polymerase is separated by centrifugation, which pellets beads bound with nonproductive enzyme and template, leaving active, productive polymerase in the supernatant. Another method to enrich active polymerase is to use magnetic beads conjugated to trap molecules (DNA or heparin). The magnetic beads are added along with reagents for DNA extension. Active polymerase which dissociates from the template binds to trap molecules on magnetic beads. Magnetic beads are then separated from the reaction mixture. Active polymerase are recovered by dissociating trap molecules, e.g., during dialysis.

Figure 22:
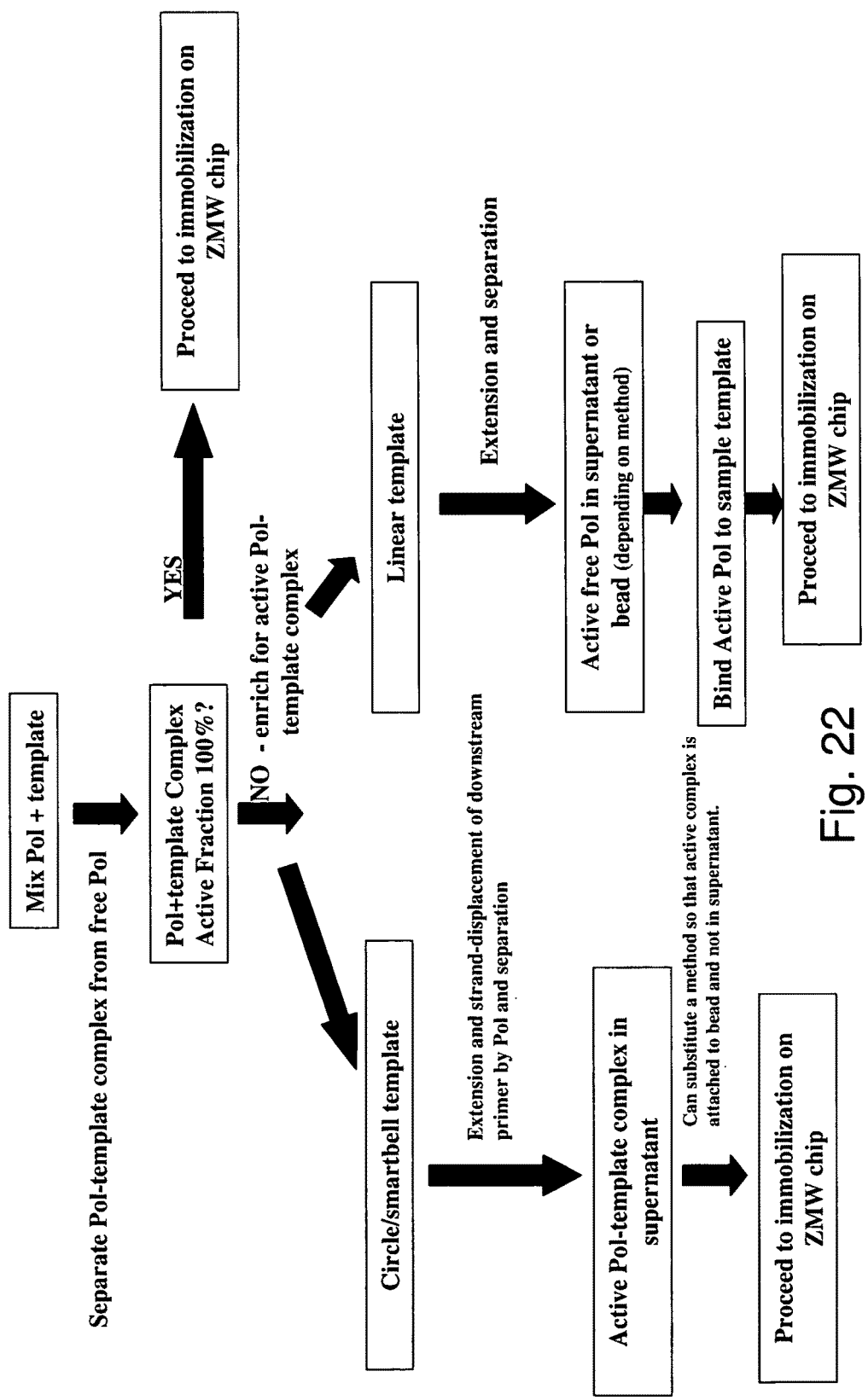
FIG. 22 provides an example flow chart for enrichment of active polymerases.
Figure 23A:
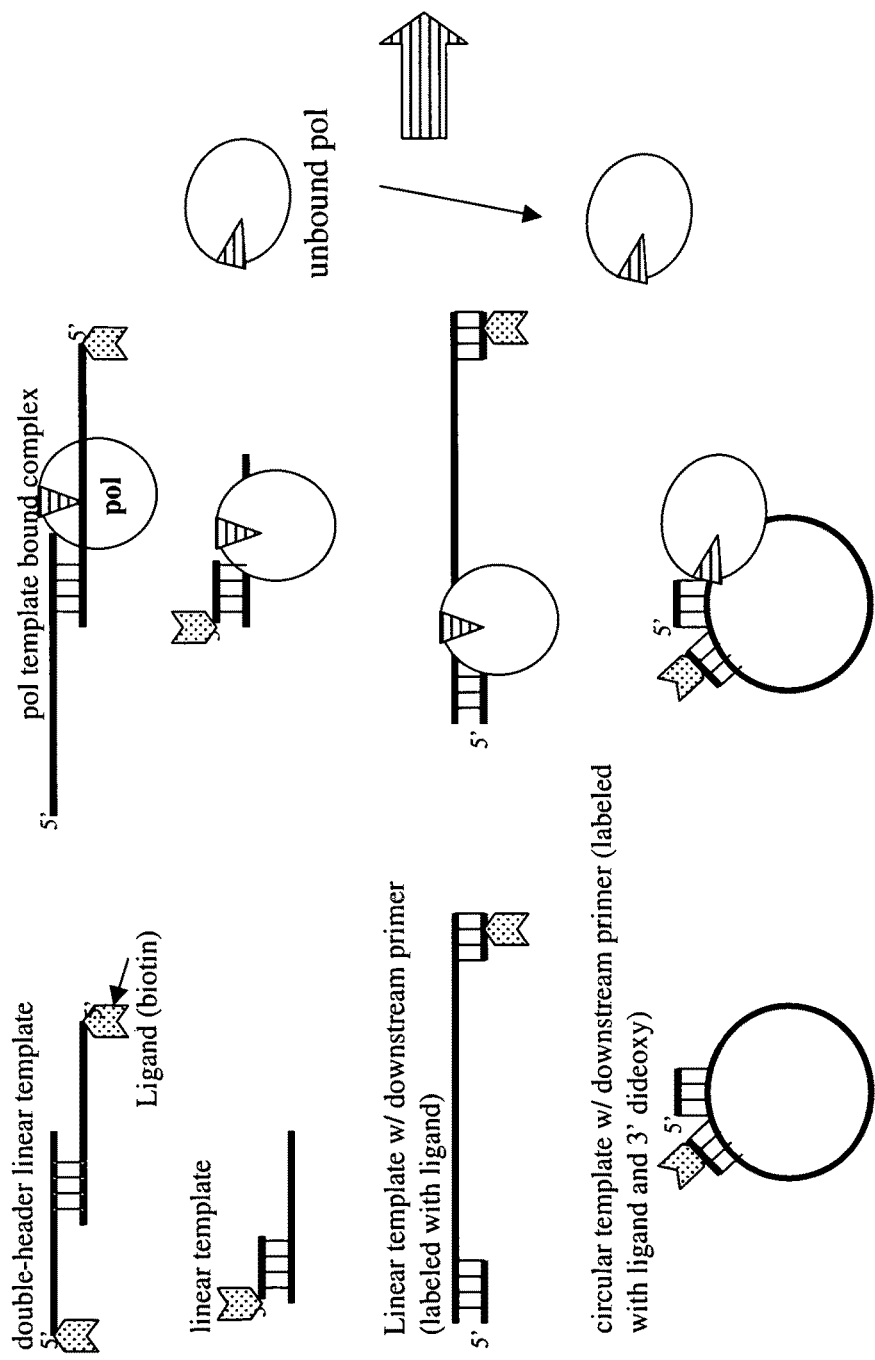
FIG. 23, panels A-B provide additional details regarding polymerase enrichment.
Figure 23B:
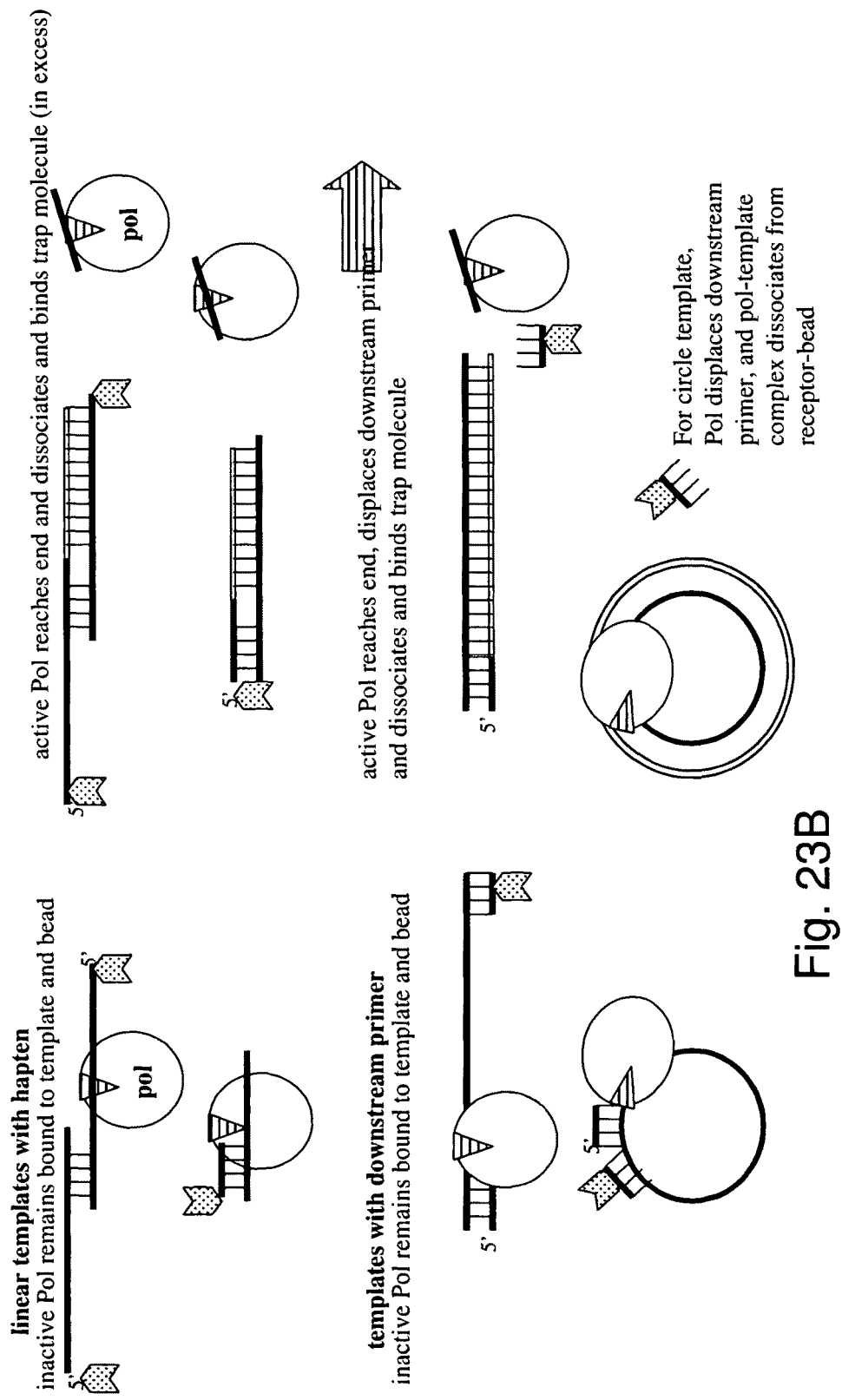

An example flow chart for enrichment of active polymerases, e.g., using phi29 as an example polymerase, is illustrated in FIG. 22. FIG. 23, panels A-B provides an example enrichment protocol. As illustrated, polymerase such as a phi29 polymerase can be enriched for the ability to bind to a template (linear, circular, etc.). Bound (active) and unbound (dead) polymerases are separated, e.g., by centrifugation. For example, the polymerase can be mixed with beads conjugated with receptor, e.g., streptavidin for biotin, antibody for FAM, and incubated. The beads are then pelleted and the supernatant, which contains unbound or inactive polymerase, discarded. Polymerization is initiated by adding dNTPs and divalent cation ($Mg^{++}$ or $Mn^{++}$) and active versus inactive polymerases are again separated, e.g., using centrifugation. In another example, engaged polymerases are more stable at 37° C. than are non-engaged polymerases, providing an additional enrichment selection scheme. A heat treatment before loading increases the proportion of productive polymerase: template complexes, leading to improved loading. The addition of $Ca^{2+}$ ions and cognate nucleotide analogs can be used to further improve loading. Similarly, pre-forming and purifying a streptavidin-polymerase complex can be performed before template is added to further enhance loading of active polymerase.

Further Details Regarding Linking Chemistries

As noted, in viral particle applications, the analyte of interest is simply packaged by the relevant viral capsid components. When non-viral particles are used, other approaches are useful for attaching the particle, array surface, etc., to the analyte molecule (e.g., DNA to be sequenced in a ZMW, or enzyme such as a polymerase to be delivered, etc.).

The binding surfaces and/or particles within the arrays of the invention can present a solid or semi-solid surface for any of a variety of available linking chemistries, allowing the binding of biological analytes of interest to the particle members to be distributed into the arrays. A wide variety of organic and inorganic polymers, both natural and synthetic can be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials that are employed, include papers, ceramics such as glass, fused silicon, quartz, metals such as gold, metalloids, semiconductive materials, cements or the like. In addition, substances that form matrixes, such as proteins (e.g., gelatins), lipopolysaccharides, silicates, agarose and polyacrylamides can also be used. Proteins can also provide particles, e.g., using antibodies that bind specific recognition components incorporated into the analyte of interest.

A wide variety of linking chemistries are available for linking molecules to a wide variety of molecular, solid or semi-solid particle support elements. These chemistries can be performed in situ (i.e., in the array) or prior to introduction of the particles into the array. It is impractical and unnecessary to describe all of the possible known linking chemistries for linking molecules to a solid support. It is expected that one of skill can easily select appropriate chemistries, depending on the intended application.

In one preferred embodiment, the particles or binding surfaces of the invention comprise silicate elements (e.g., glass or silicate beads). A variety of silicon-based molecules appropriate for functionalizing surfaces are commercially available. See, for example, *Silicon Compounds Registry and Review*, United Chemical Technologies, Bristol, Pa. Additionally, the art in this area is very well developed and those of skill will be able to choose an appropriate molecule for a given purpose. Appropriate molecules can be purchased commercially, synthesized de novo, or it can be formed by modifying an available molecule to produce one having the desired structure and/or characteristics.

A substrate linker attaches to the solid substrate through any of a variety of chemical bonds. For example, the linker is optionally attached to the solid substrate using carbon-carbon bonds, for example via substrates having (poly)trifluorochloroethylene surfaces, or siloxane bonds (using, for example, glass or silicon oxide as the solid substrate). Siloxane bonds with the surface of the substrate are formed in one embodiment via reactions of derivatization reagents bearing trichlorosilyl or trialkoxysilyl groups. The particular linking group is selected based upon, e.g., its hydrophilic/hydrophobic properties where presentation of an attached polymer in solution is desirable. Groups which are suitable for attachment to a linking group include amine, hydroxyl, thiol (e.g., in the case of gold particles), carboxylic acid, ester, amide, isocyanate and isothiocyanate. Preferred derivatizing groups include aminoalkyltrialkoxysilanes, hydroxyalkyltrialkoxysilanes, polyethyleneglycols, polyethyleneimine, polyacrylamide, polyvinylalcohol and combinations thereof.

By way of non-limiting example, the reactive groups on a number of siloxane functionalizing reagents can be converted to other useful functional groups:

1. Hydroxyalkyl siloxanes (Silylate surface, functionalize with diborane, and H2O2 to oxidize the alcohol);
   a. allyl trichlorosilane→→3-hydroxypropyl
   b. 7-oct-1-enyl trichlorchlorosilane→→8-hydroxyoctyl
2. Diol(dihydroxyalkyl)siloxanes (silylate surface and hydrolyze to diol)
   a. (glycidyl trimethoxysilane→→(2,3-dihydroxypropyloxy)propyl
3. Aminoalkyl siloxanes (amines requiring no intermediate functionalizing step)
   a. 3-aminopropyl trimethoxysilane→aminopropyl
4. Dimeric secondary aminoalkyl siloxanes
   a. bis(3-trimethoxysilylpropyl)amine→bis(silyloxylpropyl)amine.

See, for example, Leyden et al., Symposium on Silylated Surfaces, Gordon & Breach 1980; Arkles, Chemtech 7, 766 (1977); and Plueddemann, Silane Coupling Reagents, Plenum, N.Y., 1982. These examples are illustrative and do not limit the types of reactive group interconversions which are useful in conjunction with the present invention. Additional starting materials and reaction schemes will be apparent to those of skill in the art.

The components that can be attached to a derivatized particle or binding surface include nucleic acids such as DNA, polypeptides (e.g., enzymes such as polymerases), mimetics, large and small organic molecules, polymers and combinations thereof. For example, moieties bearing a charge can be easily coupled to a particle. For example, the charged group can be a carboxylate, quaternary amine or protonated amine that is a component of an amino acid that has a charged or potentially charged side chain. The amino acids can be either those having a structure which occurs naturally or they can be of unnatural structure (i.e., synthetic). Useful naturally occurring amino acids include: arginine, lysine, aspartic acid and glutamic acid. Surfaces utilizing a combination of these amino acids are also of use in the present invention. Further, peptides comprising one or more residues having a charged or potentially charged side chain are useful coating components and they can be synthesized utilizing arginine, lysine, aspartic acid, glutamic acid and combinations thereof. Useful unnatural amino acids are commercially available or can be synthesized utilizing art-recognized methodologies, such as available systems of orthogonal elements. In those embodiments in which an amino acid moiety having an acidic or basic side chain is used, these moieties can be attached to a surface bearing a reactive group through standard peptide synthesis methodologies or easily accessible variations thereof. See, for example, Jones, Amino Acid and Peptide Synthesis, Oxford University Press, Oxford, 1992.

When proteins are attached to the particles or binding surfaces, it is also possible to subsequently attach a nucleic acid to the protein. For example, a variety of proteins that specifically bind to specific DNA sequences can be used to link DNAs to the particles or binding surfaces. Examples include capsid packaging proteins, as discussed above, as well as a variety of antibodies. Similarly, nucleic acids can be attached to particles and used to bind polypeptides of interest. Linkers can be added to the DNAs for purposes of linking to the proteins on the particles or binding surfaces, using the methods discussed above, e.g., in the context of adding packaging sites to the analyte nucleic acids.

Linking groups can also be placed on the particles of the invention. Linking groups of use in the present invention can have a range of structures, substituents and substitution patterns. They can, for example be derivatized with nitrogen, oxygen and/or sulfur containing groups which are pendent from, or integral to, the linker group backbone. Examples include, polyethers, polyacids (polyacrylic acid, polylactic acid), polyols (e.g., glycerol,), polyamines (e.g., spermine, spermidine) and molecules having more than one nitrogen, oxygen and/or sulfur moiety (e.g., 1,3-diamino-2-propanol, taurine). Specific examples of linkers that can link DNA and proteins include: (1) incorporating O6-benzylguanine analog(s) on DNA, and a SNAP-tag on the protein (Stein et al. (2007) "A Covalent Chemical Genotype-Phenotype Linkage for in vitro Protein Evolution." *Chembiochem* 8:2191-2194). Another known strong DNA-protein attachment that could be exploited is between the Ter sequence at DNA replication terminators and the Tus protein, as described by Coskun-Ari and Hill (1997) "Sequence-specific Interactions in the Tus-Ter Complex and the Effect of Base Pair Substitutions on Arrest of DNA Replication in *Escherichia coli*," JBC 272: 26448-26456.

In one embodiment of the invention, the coupling chemistries for coupling materials to the particles of the invention are light-controllable, i.e., utilize photo-reactive chemistries. The use of photo-reactive chemistries and masking strategies to activate coupling of molecules to substrates, as well as other photo-reactive chemistries is generally known (e.g., for semiconductor chip fabrication and for coupling bio-polymers to solid phase materials). The use of photo-cleavable protecting groups and photo-masking permits type switching of particles, i.e., by altering the presence of substrates present on the array members (i.e., in response to light). Among a wide variety of protecting groups which are useful are nitroveratryl (NVOC)-methylnitroveratryl (Menvoc), allyloxycarbonyl (ALLOC), fluorenylmethoxycarbonyl (FMOC), -methylnitro-piperonyloxycarbonyl (MeNPOC), —NH-FMOC groups, t-butyl esters, t-butyl ethers, and the like. Various exemplary protecting groups (including both photo-cleavable and non-photo-cleavable groups) are described in, for example, Atherton et al., (1989) Solid Phase Peptide Synthesis, IRL Press, and Greene, et al. (1991) Protective Groups In Organic Chemistry, 2nd Ed., John Wiley & Sons, New York, N.Y. The use of these and other photo-cleavable linking groups for nucleic acid and peptide synthesis on solid supports is a well-established methodology.

Tethering Particles to the Array

The viral or other particles can incorporate features that permit tethering of the particles to the wells of the array. Any of the applicable linking chemistries discussed herein in the context of fixing analytes to particles are applicable to the problem of linking/tethering the particles to the surfaces of the arrays. Devices, methods and systems that incorporate functionalized regions into the walls of a ZMW, e.g., by incorporating an annular gold ring into the walls of the ZMW, are described, e.g., in Foquet et al. SUBSTRATES AND METHODS FOR SELECTIVE IMMOBILIZATION OF ACTIVE MOLECULES (U.S. Ser. No. 60/905,786, filed Mar. 7, 2007 and U.S. Ser. No. 12/074,716, filed Mar. 5, 2008).

The particles can include appropriate functionalities for linking to the relevant array surface. For example, thiol chemistries can be used to link proteins to surfaces. Recombinant proteins such as viral capsid assemblies can also include unnatural amino acids with any of a variety of linking chemistries, e.g., when expressed in a host cell that includes orthogonal elements that permit site-specific expression of the unnatural amino acid. Systems of orthogonal elements that can be used to incorporate unnatural amino acids, including amino acids with reactive groups, are described in Wang, et al. (2006) "Expanding the genetic code." *Annu Rev Biophys Biomolec Struct* 35: 225-249; Wang and Schultz (2005) "Expanding the Genetic Code," *Angewandte Chemie Int. Ed.* 44(1):34-66; Xie, et al. (2005) "An expanding genetic code." *Methods* 36: 227-38; and Xie, et al. (2006) "A chemical toolkit for proteins: an expanded genetic code." *Nat Rev Mol Cell Biol* 7: 775-82.

In the context of particles, the site specific incorporation of an amino acid that comprises a reactive/linking group can be used to specifically orient the particle relative to the array well. For example, the array well can include a specific functionalized region (e.g., a gold band, as discussed above) that can be coupled to a specific portion of the particle. For example, where the particle is a viral particle, the tail or capsid can incorporate one or more reactive/linking groups to orient the capsid relative to the well (and/or relative to other assay components, such as surface immobilized enzymes, e.g., surface immobilized polymerases).

Reading the Analyte

In the embodiments herein, the analyte molecule is optionally complexed to a particle, binding site or other entity and analyzed in a reaction site, well, ZMW or other observation volume or region of the array. In the simplest case, this is accomplished simply by performing the relevant read reaction (e.g., a copy polymerization reaction using a polymerase); the analyte is optionally complexed to the particle, etc., during this readout. This is particularly practical where the particle or other coupled moiety does not inhibit the action of relevant readout components, such as a polymerase analyte acting on a DNA template analyte. In the case of some viral particles, including many bacteriophage, the polymerase can capture the analyte DNA, which may protrude from the capsid, and can pull it from the capsid as it synthesizes a complementary strand, e.g., during a sequencing reaction. Further, active enzymes can remain bound to particles, or can be transferred from a particle to a structure in the reaction/observation region. See Hanzel et al. ACTIVE SURFACE COUPLED POLYMERASES, WO 2007/075987 and Hanzel et al. PROTEIN ENGINEERING STRATEGIES TO OPTIMIZE ACTIVITY OF SURFACE ATTACHED PROTEINS, WO 2007/075873). Similarly, a polymerase or other readout enzyme can bind to other particle-bound analytes (e.g., enzyme substrates) and can act on them without separation from the particle. However, alternate approaches can also be used, in which an analyte is separated from the particle or other moiety before it participates in a relevant reaction.

Methods of separating the analyte from the particle are available in the context of the present invention. For example, a restriction enzyme can be used to cleave an analyte DNA from the particle, after it is delivered to an array well. Similarly, a polypeptide linker can be cleaved using a site-specific protease. In another approach, as is discussed above, photo-cleavable linkers can be used to couple the analyte to the particle; upon exposure to light, the cleavable linker is cleaved, releasing the analyte. Linkers can also incorporate specifically cleavable linkages that cleave as a result of changing pH, presence of a cleavage molecule, or the like. A viral capsid can be digested away from the nucleic acid using either chemical or enzymatic methods after delivery of the capsid to the array well. Any of these methods (or combinations thereof) can result in a controllable release of the analyte molecule from the particle of interest.

Once any necessary or desired separation of the analyte and anything it is bound to is performed, the analyte can be read or can participate in the system in any of the typical methods that are used to read the array during regular single molecule analyte monitoring. For example, in the case of sequencing in a ZMW, a polymerase can be bound in the waveguide in which the sequencing reaction is performed; the incorporation of appropriately labeled nucleotides is used to determine sequences of the analyte nucleic acids. For a description of polymerases that can incorporate appropriate labeled nucleotides see, e.g., Hanzel et al. POLYMERASES FOR NUCLEOTIDE ANALOGUE INCORPORATION, WO 2007/076057. For a description of polymerases that are active when bound to surfaces, which is useful in single molecule sequencing reactions in which the enzyme is fixed to a surface, e.g., conducted in a zero mode waveguide, see Hanzel et al. ACTIVE SURFACE COUPLED POLYMERASES, WO 2007/075987 and Hanzel et al. PROTEIN ENGINEERING STRATEGIES TO OPTIMIZE ACTIVITY OF SURFACE ATTACHED PROTEINS, WO 2007/075873). For further descriptions of single molecule sequencing applications utilizing ZMWs, see Levene et al. (2003) "Zero Mode Waveguides for single Molecule Analysis at High Concentrations," *Science* 299:682-686; Eid et al. (2008) "Real-Time DNA Sequencing from Single Polymerase Molecules" *Science* DOI: 10.1126/science. 322.5905.1263b; U.S. Pat. No. 7,033,764, U.S. Pat. No. 7,052,847, U.S. Pat. No. 7,056,661, and U.S. Pat. No. 7,056,676, the full disclosures of which are incorporated herein by reference in their entirety for all purposes.

In general, analytes such as nucleic acids or polypeptides can be distributed into array wells using the methods described herein. Once the analytes are formatted into the appropriate wells, any of a variety of different analyte readout formats in current use can be used during analyte analysis. These include fluorescence measurement, epifluorescence measurements, and the like. For a discussion of array readout formats see, e.g., Kimmel and Oliver (Eds) (2006) *DNA Microarrays Part A: Array Platforms & Wet-Bench Protocols, Volume* 410 (Methods in Enzymology) ISBN-10: 0121828158; Kimmel and Oliver (Eds) (2006) *DNA Microarrays, Part B: Databases and Statistics Volume* 411 (Methods in Enzymology) ISBN-10: 0121828166; Alan R. Kohane et al. (2005) *Microarrays for an Integrative Genomics* MIT Press ISBN: 0262612100; Hardiman (2003) *Microarrays Methods and Applications* (*Nuts & Bolts series*) DNA Press, USA; Baldi and Hatfield (2002) *DNA Microarrays and Gene Expression* Cambridge University Press; ISBN: 0521800226; Bowtell and Sambrook (Eds) (2002) *DNA Microarrays: A Molecular Cloning Manual* David Paperback: 1st edition Cold Spring Harbor Laboratory; ISBN: 0879696257; *Microarrays and Related Technologies: Miniaturization and Acceleration of Genomics Research* (May 1, 2001) Cambridge Healthtech InstituteISBN: B00005TXRM; Rampal (ed) (2001) *DNA Arrays: Methods and Protocols* (Methods in Molecular Biology, Vol 170 Humana Press, ISBN: 089603822X; Schena (2000) *Microarray Biochip Technology* Eaton Pub Co ISBN: 1881299376; and Schena (Editor) (1999) *DNA Microarrays: A Practical Approach* (Practical Approach Series) Oxford Univ Press, ISBN: 0199637768. In general, a variety of commercially available array readers exist, or can be modified to read the arrays of the invention.

Controlling the Size/Charge and Distribution of Reaction/Observation Volumes of the Array In a related aspect of the invention, the invention selectively controls the quantity and/or size or charge of analyte molecules that will fit into the relevant observation volume (e.g., array well such as a ZMW, or reaction/observation portion thereof). This can be accomplished, as noted in detail above, by controlling the effective size or charge of the analyte molecule by coupling the analyte to a particle or other sizing moiety. However, the size, charge, shape and location of the array observation volumes (wells) can also be selected, resulting in the ability to tune how many analyte molecules can fit into the wells, and which wells the analytes can fit into. This type of well size selected array can also be used to help determine which regions of the array are most likely to yield the most useful analyte data (e.g., the longest sequence runs in the context of nucleic acid sequencing), thereby improving data compilation processes for complex projects (e.g., in the context of DNA sequencing, contig assembly from multiple sequencing volumes). If it is known which volumes/wells contain which specific analyte (or analyte type) then assembly can be performed within those areas that should contain the same analyte. This is especially useful when using a sizing moiety as the selection mechanism, instead of the size of the DNA per se, e.g., where the carrier or tag is selected to correspond to a particular analyte or analyte type.

In one aspect, it is desirable to eliminate, or at least sequester, small from large analytes (e.g., small from large nucleic acids). That is, there are a variety of preparatory processes that lead to the presence of small "contaminating" molecules, such as small non-target nucleic acids in a sample to be analyzed, e.g., resulting from formation of primer-dimers during preparatory nucleic acid amplification steps. Even if the small molecule is not strictly a contaminant, e.g., where a small nucleic acid actually does include target sequences to be analyzed, extremely short regions of nucleic acid can be difficult to compile into an overall contig sequence (because overlap regions are short for short nucleic acids). Indeed, where the sequence is repetitive, small fragments of a genomic DNA can be difficult or even impossible to compile.

Accordingly, one aspect of the invention includes methods of distributing a population of heterogeneously-sized nucleic acid molecules to a ZMW or other "small well" array (an array with wells that have a dimension about ½ of the excitation wavelength, e.g., about 250 nm or smaller in at least one dimension, e.g., about 200 nm or smaller in at least one dimension, optionally equal to or less than about 150 nm in at least dimension, and less than about 100 nm in some embodiments). The ZMW or other small well array is fabricated to include a population of small (e.g., "decoy") wells for capturing small contaminants or small analytes and a population of "target" wells. The target wells are typically small enough to permit optical confinement, e.g., by having a dimension about ½ the wavelength of excitation light. The decoy wells are smaller in diameter or depth than the target wells, and preferentially accept the small contaminants or small analytes (e.g., short nucleic acids), rather than larger analytes, such as large template nucleic acids. The precise dimensions of the target and decoy wells will, therefore, vary, depending on the dimensions of the analytes (e.g., nucleic acids, etc.) and the wavelength of excitation light. A population of heterogeneously-sized analytes such as nucleic acid molecules, that includes a subpopulation of short molecules and a subpopulation of long molecules is delivered to the array. The population of analytes is delivered to the array, such that the subpopulation of short molecules is preferentially delivered into the decoy wells and the subpopulation of long molecules is preferentially delivered into the target wells.

This preferential loading can be accomplished in any of a number of ways. First, the relevant analyte sample can be pre-sorted into larger and smaller analyte molecules, e.g., using typical size/charge separation methods. This can result in a continuum of size separated fragments, or in discrete populations of size separated fragments. The sized fragments are loaded onto the array (e.g., ZMW) using progressively shorter nucleic acids (i.e., the fragments are loaded onto the array, using first large and then small fragments). This results in larger molecules being delivered to the larger (e.g., target) wells, while the smaller molecules are delivered to the smaller (e.g., decoy) wells.

In some embodiments, biased immobilization strategies are useful, e.g., to fix large analytes (e.g., large DNA templates) into large wells, and small analytes (e.g., small DNA templates) into small wells. In these embodiments, the target analyte molecules (e.g., DNA templates for sequencing) can be fixed into the wells once they are delivered to the desired well type, sterically (and/or electrostatically) blocking additional analyte molecules from entering analyte loaded wells. This can be accomplished using standard surface chemistries, e.g., using a functionalized region of material at a location in the well of the array where the analyte molecule is to be fixed for analysis. Devices, methods and systems that incorporate functionalized regions into the walls of a ZMW, e.g., by incorporating an annular gold ring into the walls of the ZMW, are described, e.g., in Foquet et al. SUBSTRATES AND METHODS FOR SELECTIVE IMMOBILIZATION OF ACTIVE MOLECULES (U.S. Ser. No. 60/905,786, filed Mar. 7, 2007 and U.S. Ser. No. 12/074,716, filed Mar. 5, 2008). In these embodiments, thiol based attachment chemistries (e.g., as appropriate for gold surface chemistry) can be used.

In some embodiments, the large wells are optionally loaded first, permitting the large analytes to settle (and optionally be fixed) into the wells, with progressively smaller molecules being loaded subsequently. Alternatively, the small molecules can be loaded first, being washed out of the large wells (and, optionally fixed into the smaller wells) prior to loading (and optional fixation) of the large molecules in the large wells. Alternately, the wells can be specifically loaded, e.g., by distributing sized analytes into various regions of the array that comprise the appropriate wells size (large wells for large analytes, small wells for small analytes). In yet another embodiment, the analytes can be loaded without prior size separation, e.g., by permitting the small analytes to diffuse into the small wells, and the large analytes to diffuse into the large wells. If there is an excess of small wells, the small wells will adsorb small analyte molecules from the sample in a stochastic process, enriching the preferential delivery of large molecules (delivery of large molecules without delivery of small molecules) into the large wells.

Specific regions of the array can include specific well sizes, i.e., the array can include 1, 2, 3, 4, . . . n regions that each have a selected well size. For example, region 1 can include wells that are about 10 nm in diameter, region 2 can include wells that are about 20 nm in diameter, region 3 can include wells that are about 30 nm in diameter, etc. By loading appropriately sized analytes (e.g., DNAs) onto each of the regions of the array, it is possible to create an array with generally sized DNAs or other analytes in selected regions of the array. This assists in the eventual deconvolution of sequencing data derived from the array, in that large DNA molecule regions of the array can be checked for sequence overlap before the smaller regions, establishing a contig framework that can be used to order any short sequences that are produced from small DNAs. Additionally, sequences can be amplified prior to sequencing, with different sequences in each region of the array being replicated by many copies, each individually loaded in a well of the region, for each sequence. This allows the use of consensus sequencing to improve on the raw single molecule sequencing accuracy for a given molecule. This is also especially useful in the case where the DNA is packaged in a particle (e.g., a viral particle), because placement is independent of the DNA size in these embodiments (because the dimensions of the particle determine the size of the molecule delivered to the wells). For further details on sequence compilation from ZMW arrays, see, e.g., Turner VIRTUAL READS FOR READLENGTH ENHANCEMENT U.S. Ser. No. 60/995,732 filed Sep. 28, 2007 and U.S. Ser. No. 12/212, 106, filed Sep. 17, 2008.

Analyte particles can be used to further control the size of the analyte molecules relative to the array wells. As is discussed above in detail, the analyte of interest can be bound to or packaged by particles. These particles can be used to sterically (and/or electrostatically) control entry of analyte molecules into the wells of the array. In this embodiment, the size of the particles is used to select which well size a given analyte will fit into.

Multisized ZMW Arrays

In one implementation of the multi-sized well arrays discussed above, the invention includes a zero-mode waveguide (ZMW) array that comprises a plurality of ZMWs of selectively different size. In this embodiment, "decoy" wells smaller than "target" wells are used to capture small nucleic acids from a sample to be analyzed. The decoy wells are small enough that they can not capture large templates of interest, but large enough that they can capture small nucleic acids such as contaminants, or simply smaller analyte fragments of a nucleic acid of interest. For example, the decoy wells can be about 100 nm or smaller, e.g., about 75 nm or smaller in at least one dimension, e.g., about 60 nm or smaller, or e.g., about 50 nm or smaller.

Figure 3:
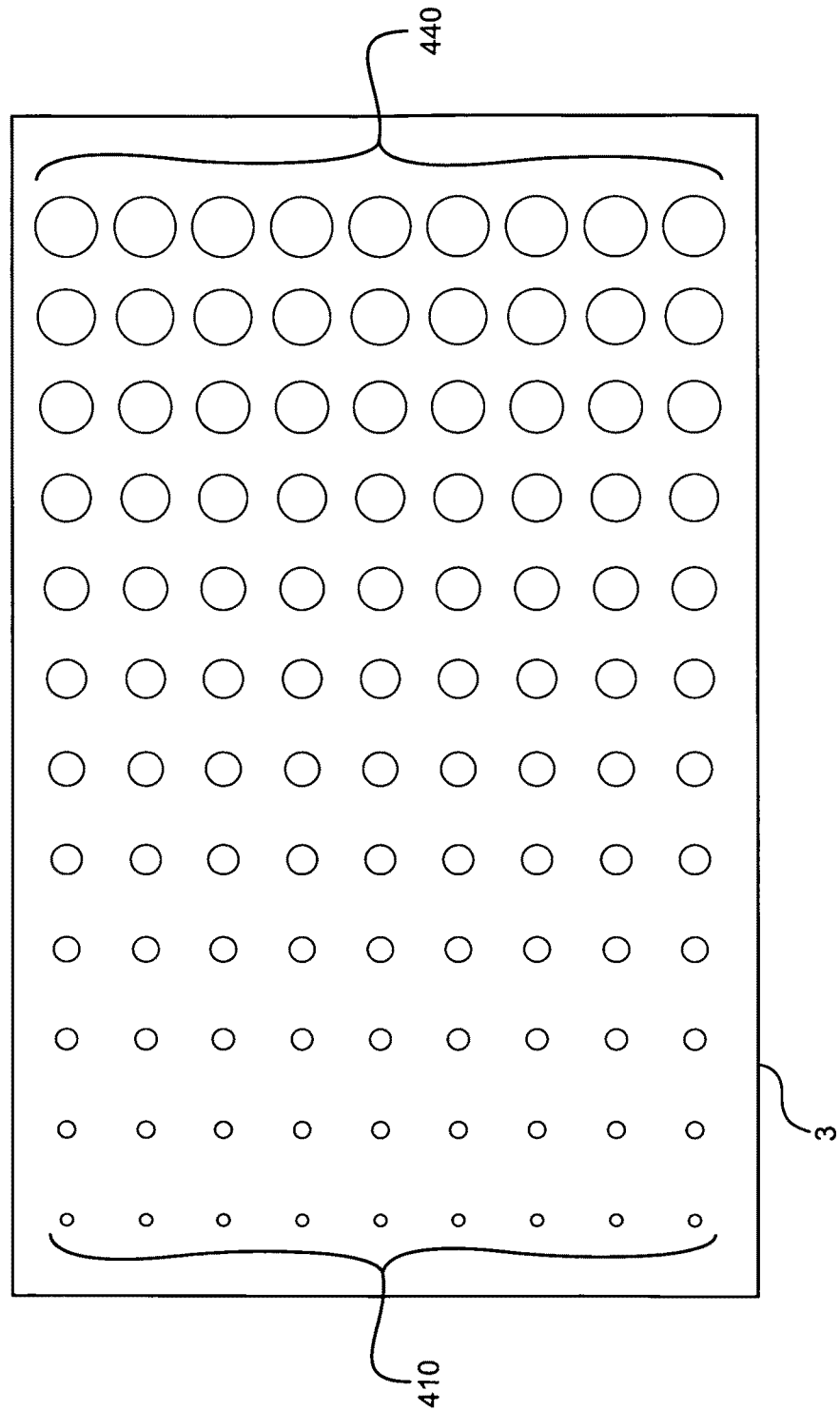
FIG. 3 schematically shows a ZMW comprising a gradient of well sizes.

This type of ZMW illustrated in FIG. 3. As shown ZMW array 3 comprises a set of ZMWs 400 arranged from progressively smaller ZMWs 410 to progressively larger ZMWs 440. A simple gradient pattern is depicted, but essentially any arrangement of wells can be used, depending on the application.

The layout of well patterns (e.g., regions of large and small wells) can be set by the user, taking available readout instrumentation into account. Essentially any layout that can be imaged by available detectors can be used, e.g., blocks of small wells and blocks of large wells, defined patterns that intersperse large and small wells, progressive gradients of large to small wells (or small to large), or the like.

Non-Random Loading of Multi-Sized ZMW Arrays

The size of the relevant wells can be used to control how many copies of a nucleic acid or other analyte can fit into each well, providing an additional basis for performing non-Poisson limited loading of the wells. The wells can be sized to accommodate only a single analyte molecule (or analyte-particle molecule). This can be achieved by controlling the diameter or depth of the well, and/or by controlling the shape of the well (e.g., if analytes or analyte particles have a particular shape, they will only fit into an appropriately shaped well). The use of decoy wells to preferentially capture small analytes can also be used to bias the number of overall analytes that can be loaded into target wells.

As above, the wells of a typical array can include greater than 30% of the target (or decoy) wells being loaded. The precise percentage that can be loaded can be greater than 37% (the approximate Poisson random loading limit to achieve single analyte molecule occupancy), and will typically be more than 38% loading, often with as much as 50% or more, and preferably as much as 60%, 70%, 80% or 90% or more of the relevant wells of the array being loaded with a single molecule in an analysis region of each well (in typical embodiments, one molecule will be loaded per well to achieve a single analyte molecule per analysis region).

It will be appreciated that these components can be arranged in arrays that comprise differently sized wells as noted above, and/or in wells that comprise particles delivered according to the invention.

Transferring Super-Poisson Loaded Analytes

In one aspect, an array that comprises a super-Poisson loaded set of analytes can be used as a source array for producing a secondary array of analyte materials. The source array can be produced by one or more method noted herein. The secondary array can be produced by any direct or indirect transfer procedure, e.g., blotting, capillary transfer, microfluidic flow of materials, or the like. This procedure is useful e.g., where a first method to produce the source array is simplified by the format of the source array, e.g., where the array is a simple planar array. In such embodiments, it is possible to deliver single molecules via the methods herein, or, e.g., through well-established print head technologies (e.g., using piezoelectric devices), microfluidic technologies, or typical array copying techniques. In addition to the methods herein, additional details can be found in *Nanotechnology* 10:225-231 (1999).

A duplicate or copy array duplicates some or all components of a parental array. For example, an array of reaction mixtures might include nucleic acids, polymerases, etc., at sites in the array, while a duplicate or copy array can also include the complete reaction mixtures, or, alternately, can include, e.g., the nucleic acids, or polymerases, without including the other reaction mixture components.

Arrays can be partially or completely duplicated in or by the methods and systems of the invention. For example, aliquots of reaction mixtures or products can be taken and copy arrays formed from the aliquots. Similarly, master arrays comprising, e.g., the nucleic acids or polymerases found in reaction mixtures can be produced. The precise manner of production of array copies varies according to the physical nature of the array, as discussed in detail herein. For example, where arrays are formed in microtiter trays, copy arrays are conveniently formed in microtiter trays, or, e.g., in ZMWs, e.g., by automated pipetting or microfluidic transfer of aliquots of material from an original array. However, arrays can also change form in the copying process, i.e., liquid phase copies can be formed from solid phase arrays, or vice versa, or a logical array can be converted to a simple spatial array in the process of forming the copy (e.g., by moving or creating an aliquot of material corresponding to a member of the logical array, and, subsequently, placing the aliquot with other array members in an accessible spatial relationship such as a gridded array), or vice versa (e.g., array member positions can be recorded and that information used as the basis for logical arrays that constitute members of multiple spatial arrays).

Examples of transferring material from one array to another can be performed in a variety of ways. For example, DNA (e.g., plasmid or PCR or other amplification product, e.g., a single copy or multiple identical copies per array position) encoding a protein (e.g., polymerase, or antibody, or antigen, or an unknown protein) in a first array, can be subjected to cell-free expression (in-vitro transcription/translation), with the protein product being transferred to the second array. Several advantages to this method exist: first, the DNA in the first array is an essentially unlimited source of material to make proteins for the second array; second, the location of each DNA in the first array is known and can be tracked; thus, if the protein produced from an array location is of interest, the individual source DNA is available for identification or further use; and third, the first array can be used to make fresh proteins just prior to use, which is an advantage when degradation of proteins is an issue.

In another example, the target to be analyzed (e.g., genomic DNA fragments, or a set of plasmids, or a set of PCR or other amplification products); provided as single copies or as multiple identical copies per array position, can be arrayed in a first array, and then single copies can be transferred to the second array. At least two advantages to this method exist: first, the DNA in the first array is an essentially unlimited source of material for analysis; and second the spatial separation of the different DNA fragments in the first array can be exploited for genomic assembly, similar to the way in which a Bacterial Artificial Chromosome (BAC) is used for mapping and contig assembly. As an example, a genome can be fragmented by restriction digestion, individual molecules can be ligated to adaptors such as SMRT-bells (see, e.g., 61/072,160, filed Mar. 28, 2008 and 61/099,696, filed Sep. 24, 2008 and filed in the PCT on Mar. 27, 2009 (Application numbers unassigned), entitled "Compositions and methods of Nucleic acid Sample Preparation" and "Compositions and Methods for Nucleic Acid Sequencing") to form circular molecules, the molecules can then be amplified by rolling circle replication or PCR, and the individual amplified units can be dispersed into individual positions of an array (the order of these events can be modified, such as by amplifying after dispersing single molecules). This arrayed material is logically equivalent for mapping purposes to a set of BACs. After the first array is made, portions of each array member can be transferred to a second array for single-molecule analysis, such as sequencing. Repeating the analysis, either on the same segment of the DNA analyzed the first time, or on a different segment, gives additional information or higher confidence in the original information; knowing that the analysis is being performed on the same starting (and, e.g., pure) DNA aids interpretation. For example, a set of 200 overlapping 1000-base reads from a 100,000 base-pair fragment is more useful during sequence assembly than the same reads from a 3-billion base-pair genome.

Other array copying and transferring protocols are also applicable. For example, an array of AFM tips, in which the gold tip is sharp enough that only one polymerase can fit at the tip, can exist as an original array, which can then be lowered into an array of ZMWs to transfer polymerases to the ZMW array. In another embodiment, an array of gold nanoparticles (optionally comprising any attached moieties) can be formed on flat glass, and then the flat glass array can be aligned face-to-face with a ZMW array. The gold particles can be pulled from the flat glass into the ZMW array, e.g., if a magnetic or charged particle were linked to the gold particles (optionally, the magnetic/charged particle can be removed afterwards).

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. For example, particle delivery can be practiced with array well sizing methods as described. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

What is claimed is:

1. A method of distributing a population of target molecules into a plurality of size confined reaction or observation regions, the method comprising:
   providing a structure comprising the plurality of size confined reaction or observation regions, wherein such regions comprise wells;
   providing the population of target molecules to be distributed;
   linking at least one nucleic acid sizing moiety to individual target molecules, wherein the sizing moieties are of sufficient size, relative to the size-confined reaction or observation regions, such that only a single sizing moiety will fit into each size confined region, thereby preventing the entry of an additional sizing moiety; and,
   loading the target molecules into the regions such that the size of the confined regions results in a single target molecule distributed into each region, thereby distributing the population of target molecules into the plurality of size confined regions.

2. The method of claim 1, wherein the size confined regions are optically confined.

3. The method of claim 1, wherein the sizing moieties expand upon binding to structures in the confined regions, thereby preventing additional sizing moieties from entering into the confined regions.

4. The method of claim 1, wherein individual sizing moieties are non-covalently linked to individual target molecules of the confined regions.

5. The method of claim 4, wherein the target molecules are polymerase enzyme molecules that comprise a reactive or binding moiety that permits attachment of the sizing moiety.

6. A method of distributing a population of target molecules into a plurality of wells in a small well array, the method comprising:
   providing the small well array, which array comprises the plurality of wells, which wells individually comprise a reaction or observation region;
   providing a population of nucleic acid particles that comprise, bind, or package a single target molecule, wherein the plurality of wells individually are configured to receive a single particle from the population of particles into the reaction or observation region of the well wherein the nucleic acid particles prevents the entry of additional nucleic acid particles; and;
   delivering the population of particles into the plurality of wells, thereby distributing a single target molecule into the plurality of wells of the small well array.

7. The method of claim 1 wherein the wells comprise zero-mode waveguides (ZMWs).

8. The method of claim 7 wherein the ZMWs have diameters of about 20 nm to about 200 nm.

9. The method of claim 1 wherein the nucleic acid sizing moiety comprises a cloned nucleic acid (DNA or RNA), an expressed nucleic acid, a genomic nucleic acid, an amplified nucleic acid or a cDNA.

10. The method of claim 1 wherein the nucleic acid sizing moiety has a single binding moiety.

11. The method of claim 1 wherein the nucleic acid sizing moiety comprises a self-assembled DNA structure.

12. The method of claim 1 wherein the single target molecules comprise polymerase enzymes.

13. A method of distributing a population of target molecules into a plurality of size confined reaction or observation regions, the method comprising:
   providing a structure comprising the plurality of size confined reaction or observation regions, wherein such regions comprise wells;
   providing the population of target molecules to be distributed;
   linking at least one nucleic acid sizing moiety to individual target molecules, wherein the sizing moieties are of sufficient size, relative to the size-confined reaction or observation regions, so that only a selected number of sizing moieties will fit into the size confined regions, wherein the nucleic acid sizing moiety comprises DNA origami; and,
   loading the target molecules into the regions such that the size of the confined regions results in a single target molecule distributed into each region, thereby distributing the population of target molecules into the plurality of size confined regions.

14. The method of claim 13 wherein the nucleic acid sizing moiety comprises a single polymerase binding site.

15. The method of claim 13 wherein the nucleic acid sizing moiety is made by the polymerase enzyme target molecule.

* * * * *